ns426B2" />

(12) United States Patent
Mattes et al.

(10) Patent No.: US 9,198,426 B2
(45) Date of Patent: Dec. 1, 2015

(54) USE OF 5 PYRIDIN-4-YL-1,3-THIAZOLES FOR CONTROLLING PHYTOPATHOGENIC FUNGI

(75) Inventors: Amos Mattes, Langenfeld (DE); Ruth Meissner, Leverkusen (DE); Klaus Tietjen, Langenfeld (DE); Christoph Andreas Braun, Düsseldorf (DE); Peter Dahmen, Neuss (DE); Martin Kaußmann, Köln (DE); Peter Schreier, Köln (DE); Arnd Voerste, Köln (DE); Ulrike Wachendorff-Neumann, Neuwied (DE); Hans-Georg Schwarz, Langenfeld (DE); Jürgen Benting, Leichlingen (DE)

(73) Assignee: Bayer Intellectual Property GmbH, Monheim (DE)

( * ) Notice: Subject to any disclaimer, the term of this patent is extended or adjusted under 35 U.S.C. 154(b) by 743 days.

(21) Appl. No.: 12/654,456

(22) Filed: Dec. 18, 2009

(65) Prior Publication Data

US 2010/0168185 A1 Jul. 1, 2010

(30) Foreign Application Priority Data

Dec. 19, 2008 (EP) .................................. 08172228

(51) Int. Cl.
*A01N 43/78* (2006.01)
*C07D 417/04* (2006.01)
*A01P 3/00* (2006.01)

(52) U.S. Cl.
CPC .............. *A01N 43/78* (2013.01); *C07D 417/04* (2013.01)

(58) Field of Classification Search
CPC .............................. A01N 43/78; C07D 417/04
USPC .......................................... 504/101; 514/342
See application file for complete search history.

(56) References Cited

U.S. PATENT DOCUMENTS

| | | | |
|---|---|---|---|
| 4,245,432 | A | 1/1981 | Dannelly |
| 4,272,417 | A | 6/1981 | Barke et al. |
| 4,482,712 | A | 11/1984 | Krumkalns |
| 4,808,430 | A | 2/1989 | Kouno |
| 5,876,739 | A | 3/1999 | Turnblad et al. |
| 5,945,380 | A | 8/1999 | Gallenkamp et al. |
| 6,962,933 | B1 | 11/2005 | Ohkawa et al. |
| 2003/0176428 | A1 | 9/2003 | Schneidersmann et al. |
| 2004/0063946 | A1 | 4/2004 | Ohkawa et al. |
| 2006/0135566 | A1 | 6/2006 | Ohkawa et al. |
| 2007/0105919 | A1 | 5/2007 | Nakajima et al. |
| 2008/0039633 | A1 | 2/2008 | Jung et al. |
| 2009/0030024 | A1 | 1/2009 | Greul et al. |

FOREIGN PATENT DOCUMENTS

| | | |
|---|---|---|
| EP | 1 402 900 A1 | 3/2004 |
| JP | 05-70446 A | 3/1993 |
| WO | WO 89/10396 A1 | 11/1989 |
| WO | WO 96/33270 A1 | 10/1996 |
| WO | WO 96/37493 A1 | 11/1996 |
| WO | WO 99/21555 A2 | 5/1999 |
| WO | WO 99/64418 A1 | 12/1999 |
| WO | WO 01/30778 A1 | 5/2001 |
| WO | WO 01/74811 A2 | 10/2001 |
| WO | WO 02/28186 A2 | 4/2002 |
| WO | WO 02/080675 A1 | 10/2002 |
| WO | WO 2004/089937 A1 | 10/2004 |
| WO | WO 2006/109084 A1 | 10/2006 |
| WO | WO 2006/137658 A1 | 12/2006 |
| WO | WO 2007/024782 A2 | 3/2007 |
| WO | WO 2007/027777 A2 | 3/2007 |
| WO | WO 2007/033780 A2 | 3/2007 |
| WO | WO 2007/039177 A2 | 4/2007 |
| WO | WO 2007/076348 A2 | 7/2007 |
| WO | WO 2007/077574 A2 | 7/2007 |
| WO | WO 2007/093542 A1 | 8/2007 |
| WO | WO 2007/137107 A2 | 11/2007 |
| WO | WO 2008/132434 A2 | 11/2008 |

OTHER PUBLICATIONS

Ashimori, A., et al., "Novel 1,4-Dihydropyridine Calcium Antagonists. I. Synthesis and Hypotensive Activity of 4-(Substituted Pyridyl)-1,4-dihydropyridine Derivatives," *Chem. Pharm. Bull.* 38:2446-2458, Pharmaceutical Society of Japan, Japan (1990).

Bakulev, V.A., et al., "Two Directions of Cyclization of α-Diazo-β-Dithioamides. New Rearrangements of 1,2,3-Triazole-4-Carbothiamides," *Tetrahedron* 45:7329-7340, Pergamon Press, PLC, United Kingdom (1989).

Barbachyn, M.R., "Identification of Phenylisoxazolines as Novel and Viable Antibacterial Agents Active against Gram-Positive Pathogens," *J. Med. Chem.* 46:284-302, American Chemical Society, United States (2003).

Bergmark, W.R., et al., "Photoenolization with α-Chloro Substituents," *J. Org. Chem.* 50:5612-5615, American Chemical Society, United States (1985).

Chavarot, M., "Synthesis of an Adenine-Pyridinaldoxime-Acridine Conjugate for Recognition of Abasic Site Lesions in DNA," *Tetrahedron* 53:13749-13756, Elseveir Science Ltd., Great Britain (1997).

Cherkasov, R.A., et al., "Tetrahedron Report No. 186: Organothiophosphorus Reagents in Organic Synthesis," *Tetrahedron* 41:25672624, Pergamon Press Ltd., Great Britain (1985).

(Continued)

*Primary Examiner* — Johann R Richter
*Assistant Examiner* — Andriae M Holt
(74) *Attorney, Agent, or Firm* — Sterne, Kessler, Goldstein & Fox P.L.L.C.

(57) ABSTRACT

The present invention relates to the use of known 5-pyridin-4-yl-1,3-thiazoles for controlling phytopathogenic fungi in plants and parts of plants, and also to methods for controlling phytopathogenic fungi in plants and parts of plants in crop protection, and also to crop protection compositions comprising these 5-pyridin-4-yl-1,3-thiazoles.

11 Claims, No Drawings

(56) References Cited

OTHER PUBLICATIONS

Doi, H., et al., "Palladium(0)-Mediated Rapid Methylation and Fluoromethylation on Carbon Frameworks by Reacting Methyl and Fluoromethyl Iodide with Aryl and Alkenyl Boronic Acid Esters: Useful for the Synthesis of [$^{11}$C]CH$_3$-C- and [$^{18}$F]FCH$_2$-C-Containing PET Tracers (PET=Positron Emission Tomography)," *Chem. Eur. J.* 15:4165-4171, Wiley-VCH Verlag GmbH & Co. KGaA, Germany (2009).

Draber, W. And R. Wegler, "Gibberelline" in *Chemie der Pflanzenschutz-und Schädlingsbekämpfungsmittel* 2:401-412, Springer Verlag, Gemany (1970).

Gellibert, F., et al., "Identification of 1,5-Naphthyridine Derivatives as a Novel Series of Potent and Selective TGF-β Type I Receptor Inhibitors," *J. Med. Chem.* 47:4494-4506, American Chemical Society, United States (2004).

Hämmerle, J., et al., "A Comparative Study on Stille Cross-Coupling Reactions of 2-Phenylthiazoles and 2-Phenyloxazoles," *Synthesis* 19:3099-3107, Georg Thieme Verlag Stuttgart, United States (2008).

Jiménez, M., et al., "Sugars and amino acids as factors affecting the synthesis of fumonisims in liquid cultures by isolates of the *Gibberella fujikuroi* complex," *Int. J. Food Microbiol.* 89:185-193, Elsevier Science B.V., Netherlands (2003).

Kumar, K., et al., "Biologically Active Compounds through Catalysis: Efficient Synthesis of N-(Heteroarylcarbonyl)-N'-(arylalkyl)piperazines," *Chem. Eur. J.* 10:746-757, Wiley-VCH Verlag GmbH & Co. KGaA, Germany (2004).

Larock, R., "9. Interconversion of Nitriles, Carboxylic Acids and Derivatives," in Comprehensive Organic Transformations, pp. 1929-1930, vol. 2, Wiley-VCH, Germany (1999).

Laufer, S.A., et al., "Regiospecific and Highly Flexible Synthesis of 1,4,5-Trisubstituted 2-Sulfanylimidazoles from Structurally Diverse Ethanone Precursors," *Synthesis* 2:253-266, Georg Thieme Verlag Stuttgart, United States (2008).

Li, W., et al., "An Improved Protocol for the Preparation of 3-Pyridyl- and Some Arylboronic Acids," *J. Org. Chem.* 67:5394-5397, American Chemical Society, United States (2002).

McCormick, S.P., et al., "Tri1 in *Fusarium graminearum* Encodes a P450 Oxygenase," *Appl. Environmental Microbiol.* 70:2044-2051, American Society for Microbiology, United States (2004).

Miwatashi, S., et al., "Novel Inhibitor of p38 MAP Kinase as an Anti-TNF-α Drug: Discovery of N-[4-[2-Ethyl-4-(3-methylphenyl)-1,3-thiazol-5-yl]-2-pyridyl]benzamide (TAK-715) as a Potent and Orally Active Anti-Rheumatoid Arthritis Agent," *J. Med. Chem.* 48:5966-5979, American Chemical Society, United States (2005).

Miwatashi, S., et al., "Synthesis and Biological Activities of 4-Phenyl-5-pyridyl-1,3-thiazole Derivatives as p38 MAP Kinase Inhibitors," *Chem. Pharm. Bull.* 53:410-418, Pharmaceutical Society of Japan, Japan (2005).

Montalbetti, C.A.G.N. and V. Falque, "Amide bond formation and peptide coupling," *Tetrahedron Lett.* 61:10827-10852, Elsevier Ltd., Netherlands (2005).

Moreno, I., et al., "A Simple Route to New Phenanthro- and Phenanthroid-Fused Thiazoles by a PIFA-Mediated (Hetero)biaryl Coupling Reaction," *Eur. J. Org. Chem.* 13:2126-2135, Wiley-VCH Verlag GmbH, Germany (2002).

Potts, K.T. And P.A. Winslow, "Synthesis of 4-, 5- and 6-Methyl-2,2'-bipyridinyls," *J. Org. Chem.* 50:5405-5409, American Chemical Society, United States (1985).

Profft, V.E. And H. Richter, "Über die Darstellung der 4-Halogenide des 2-Methylpyridins," *J. Prak. Chem.* 9:164-172, Germany (1959).

Revesz, L., et al., "Novel p38 inhibitors with potent oral efficacy in several models of rheumatoid arthritis," *Bioorg. Med. Chem. Lett.* 14:3595-3599, Elsevier Ltd., Netherlands (2004).

Revesz, L., et al., "SAR of 4-Hydroxypiperidine and Hydroxyalkyl Substituted Heterocycles as Novel p38 Map Kinase Inhibitors," *Bioorg. Med. Chem. Lett.* 10:1261-1264, Elsevier Science Ltd., Netherlands (2000).

Roger, J., et al., "Ligand-Free Palladium-Catalyzed Direct Arylation of Thiazoles at Low Catalyst Loadings," *J. Org. Chem.* 74:1179-1186, American Chemical Society, United States (2009).

Saitton, S., et al., "A synthetic approach to 2,3,4-substituted pyridines useful as scaffolds for tripeptidomimetics," *Tetrahedron. Lett.* 46:3883-3887, Elsevier Ltd., Netherlands (2004).

Sakthivel, K. and P. Dan Cook, "Direct $S_NAr$ amination of fluorinated imidazo[4,5-c]-pyridine nucleosides: efficient syntheses of 3-fluoro-3-deazaadenosine analogs," *Tetrahedron Lett.* 61:10827-10852, Elsevier Ltd., Netherlands (2005).

Schlosser, M. and F. Cottet, "Silyl-Mediated Halogen/Halogen Displacement in Pyridines and Other Heterocycles," *Eur. J. Org. Chem.* 24:4181-4184, Wiley-VCH GmbH & Co. KGaA, Germany (2002).

Seefeld, M.A., et al., "Discovery of 5-pyrroloypyridinyl-2-thiophenecarboxamides as potent AKT kinase inhibitors," *Bioorg. Med. Chem. Lett.* 19:2244-2248, Elsevier Ltd., Netherlands (2009).

Stanetty, P., et al., "Halogenated 2'-Chlorobithiazoles via Pd-Catalyzed Cross-Coupling Reactions," *J. Org. Chem.* 71:3754-3761, American Chemical Society, United States (2006).

Szczepankiewicz, B.G., at al., "Aminopyridine-Based c-Jun N-Terminal Kinase Inhibitors with Cellular Activity and Minimal Cross-Kinase Activity," *J. Med. Chem.* 49:3563-3580, American Chemical Society, United States (2006).

Wang, W.-L., et al., "Discovery of Inhibitors of *Escherichia coli* Methionine Aminopeptidase with the Fe(II)-Form Selectivity and Antibacterial Activity," *J. Med. Chem.* 51:6110-6120, American Chemical Society, United States (2008).

Wiles, J.A., et al., "Biological evaluation of isothiazoloquinolones containing aromatic heterocycles at the 7-position: In vitro activity of a series of potent antibacterial agents that are effective against methicillin-resistant *Staphylococcus aureus*," Bioorg. Med. Chem. Lett. 16:1277-1281, Elsevier Ltd., Netherlands (2006).

Patent Abstracts of Japan, Unverified English language abstract of JP 05-70466 A (Document FP2), Japanese Patent Office (1993).

Unverified English language abstract of WO 2004/089937 A1 (Document FP12) (2004).

International Search Report for International Appl. No. PCT/EP2009/008737, European Patent Office, Netherlands, mailed on Jan. 25, 2010.

USE OF 5 PYRIDIN-4-YL-1,3-THIAZOLES FOR CONTROLLING PHYTOPATHOGENIC FUNGI

The present invention relates to the use of known 5-pyridin-4-yl-1,3-thiazoles for controlling phytopathogenic fungi and for reducing mycotoxins in plants and parts of plants, and also to methods for controlling phytopathogenic fungi and for reducing mycotoxins in plants and parts of plants in crop protection, and also to crop protection compositions comprising these 5-pyridin-4-yl-1,3-thiazoles. It relates furthermore to novel 5-pyridin-4-yl-1,3-thiazoles for controlling phytopathogenic fungi and for reducing mycotoxins in plants and parts of plants, and also to methods for controlling phytopathogenic fungi and for reducing mycotoxins in plants and parts of plants in crop protection, and also to crop protection compositions comprising these novel 5-pyridin-4-yl-1,3-thiazoles, and also to preparation processes for producing the compounds.

Since the ecological and economic demands made on modern fungicides are increasing constantly, for example with respect to activity spectrum, toxicity, selectivity, application rate, formation of residues and favourable manufacture, and there can furthermore be problems, for example, with resistance, there is a constant need to develop novel fungicides which, at least in some areas, better meet the demands stated.

Surprisingly, it has now been found that the present 5-pyridin-4-yl-1,3-thiazoles achieve the objects mentioned at least in some aspects and are suitable as crop protection agents, in particular fungicides.

5-Pyridin-4-yl-1,3-thiazoles as such are already known as pharmaceutically active compounds (see, for example: WO99/21555, WO99/64418, JP05070446, WO01/30778, WO01/74811, WO02/062792, WO2000/64894 WO2001/10865, WO2007/077574, WO2006/137658, WO2004/089937, WO2005/063743, WO2007/076348, Chem. Pharm. Bull. 2005, 53, 410-418, J. Med. Chem. 2005, 48, 5966, J. Med. Chem. 2004, 47, 4494; Bioorg. Med. Chem. Lett. 2000, 10, 1261; Bioorg. Med. Chem. Lett. 2004, 14, 3595), but not their surprising fungicidal activity.

It has now been found that 5-pyridin-4-yl-1,3-thiazoles of the general formula (I)

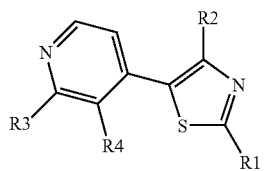
(I)

in which
R$^1$ represents hydrogen, represents an optionally hydroxyl-, amino-, cyano-, C$_1$-C$_4$-alkoxy-, R$^5$-, OR$^5$-, (C$_1$-C$_4$-alkyl)sulphanyl-, (C$_1$-C$_4$-alkyl)sulphinyl-, (C$_1$-C$_4$-alkyl)sulphonyl-, (C$_1$-C$_4$-alkyl)amino-, bis(C$_1$-C$_4$-alkyl)amino-, C$_1$-C$_4$-alkylcarbonyloxy-, C$_1$-C$_4$-alkylcarbonylamino-, NHCOR$^5$- or OCOR$^5$-substituted C$_1$-C$_8$-alkyl,
C$_1$-C$_6$-haloalkyl,
represents an optionally C$_1$-C$_4$-alkyl- or halogen-substituted C$_3$-C$_8$-cycloalkyl,
represents COR$^6$, COOR$^6$, CON(R$^6$)$_2$, (CH$_2$)$_m$OR$^6$, (CH$_2$)$_m$SR$^6$, (CH$_2$)$_m$SOR$^6$, (CH$_2$)$_m$SO$_2$R$^6$, (CH$_2$)$_m$SON(R$^6$)$_2$, (CH$_2$)$_m$SO$_2$N(R$^6$)$_2$, (CH$_2$)$_m$N(R$^6$)$_2$, (CH$_2$)$_m$NR$^6$COR$^6$, (CH$_2$)$_m$COOR$^6$, (CH$_2$)$_m$CON(R$^6$)$_2$, (CH$_2$)$_m$COR$^6$, (CH$_2$)$_m$C(NOR$^6$)R$^6$
represents N(R$^6$)$_2$, NR$^6$(CH$_2$)$_m$COOR$^6$, N=CR$^6$N(R$^6$)$_2$, NR$^6$COR$^6$, NR$^6$, NR$^6$CO(CH$_2$)$_m$OR$^6$, NR$^6$COCH(C$_1$-C$_4$-alkyl)OR$^6$, NR$^6$CO(CH$_2$)$_m$N(R$^6$)$_2$, NR$^6$CO(CH$_2$)$_m$COOR$^6$, NR$^6$COOR$^7$, NR$^6$CON(R$^6$)$_2$, NR$^6$CO(CH$_2$)$_m$R$^8$, NR$^6$(CH$_2$)$_m$R$^8$, NR$^6$SO$_2$R$^6$
or
R$^1$ represents a saturated or partially saturated, five- to seven-membered heterocycle which may contain up to four heteroatoms selected from the group consisting of N, O and S, where two oxygen atoms are not adjacent, and which is unsubstituted or optionally mono- or polysubstituted by oxo, hydroxyl, halogen, C$_1$-C$_6$-alkyl, C$_1$-C$_4$-haloalkyl, C$_1$-C$_4$-alkoxy, C$_1$-C$_6$-alkylcarbonyl C$_1$-C$_6$-haloalkylcarbonyl, C$_1$-C$_6$-alkoxycarbonyl or by optionally halogen- or C$_1$-C$_4$-alkyl-substituted phenyl
or
R$^1$ represents a phenyl radical which is optionally mono- or polysubstituted, preferably substituted up to three times, by identical or different radicals from the group consisting of C$_1$-C$_4$-alkyl, halogen, cyano, C$_1$-C$_4$-haloalkyl, OR$^6$, N(R$^6$)$_2$, SR$^6$, SOR$^6$, S(O)$_2$R$^6$, SO$_2$N(R$^6$)$_2$, COOR$^6$, COR$^6$, C(NOR$^6$)R$^6$, (CH$_2$)$_m$OR$^6$, CON(R$^6$)$_2$, CH=CR$^6$COOR$^6$
or
R$^1$ represents a five-membered heteroaromatic which may contain up to three heteroatoms selected from the group consisting of N, O and S, where two oxygen atoms or two nitrogen atoms are not adjacent, and which is optionally mono- or polysubstituted by identical or different radicals from the group consisting of halogen, hydroxyl, cyano, C$_1$-C$_4$-alkyl, C$_1$-C$_4$-haloalkyl, C$_1$-C$_4$-alkoxy, C$_1$-C$_4$-haloalkoxy, C$_1$-C$_4$-alkoxycarbonyl, C$_1$-C$_4$-alkylcarbonyl and phenyl
or
R$^1$ represents a six-membered heteroaromatic which may contain up to four heteroatoms selected from the group consisting of N, O and S, where two oxygen atoms are not adjacent, and which is optionally mono- or polysubstituted by halogen, hydroxyl, cyano, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylcarbonyl, C$_1$-C$_4$-alkoxycarbonyl or phenyl;
R$^2$ represents an aryl radical which is optionally mono- or polysubstituted by identical or different radicals from the group consisting of halogen, cyano, hydroxyl, SF$_6$, nitro, C$_1$-C$_6$-alkyl, C$_3$-C$_8$-cycloalkyl, C$_1$-C$_4$-haloalkyl, C$_2$-C$_6$-alkenyl, C$_2$-C$_6$-alkynyl, OR$^6$, (C$_1$-C$_4$)alkoxy(C$_1$-C$_4$)alkyl, (C$_1$-C$_2$)alkanediylbisoxy, (C$_1$-C$_2$)haloalkanediylbisoxy, C$_3$-C$_5$-alkanediyl, N(R$^6$)$_2$, SR$^6$, COOR$^6$, COR$^6$, C(R$^6$)NOR$^6$, CON(R$^6$)$_2$, CH=CR$^6$COOR$^6$, O(CH$_2$)$_m$COOR$^6$, NR$^6$COR$^6$, NR$^6$CON(R$^6$)$_2$ NR$^6$COO(R$^7$) or optionally halogen-, C$_1$-C$_4$-alkyl-, C$_1$-C$_4$-alkoxy-substituted phenyl
or
R$^2$ represents a five- or six-membered heteroaromatic which may contain up to four heteroatoms selected from the group consisting of N, O and S, where two oxygen atoms are not adjacent, and which is optionally mono- or polysubstituted by identical or different radicals from the group consisting of halogen, cyano, C$_1$-C$_4$-alkyl, C$_1$-C$_4$-alkoxy, C$_1$-C$_4$-haloalkyl, phenyl and C$_3$-C$_8$-cycloalkyl;
R$^3$ represents hydrogen, halogen, cyano, hydroxyl, OR$^6$, cyano, amino, C$_1$-C$_6$-alkyl, C$_1$-C$_8$-haloalkyl, (CH$_2$)$_m$OR$^6$, (CH$_2$)$_m$CN, (CH$_2$)$_m$N(R$^6$)$_2$, COOR$^6$, CON(R$^6$)$_2$, $SR^6$, $SOR^6$, $S(O)_2R^6$, $N(R^6)_2$, $NR^6COR^6$, $NR^6COOR^7$, $NR^6CON(R^6)_2$, $NR^6SO_2R^6$, $N=S(O)(R^6)_2$; $N=CR^6N(R^6)_2$, $NR^6CO(CH_2)_mR^9$ or $NR^6(CH_2)_mR^9$;

$R^4$ represents hydrogen or $C_1$-$C_4$-alkyl or together with $R^3$ forms, via the pyridine radical to which both are attached, a five- or six-membered mono- or polyunsaturated cycle which may contain a nitrogen atom;

$R^5$ represents a phenyl radical which is optionally substituted by halogen, hydroxyl, cyano, $C_1$-$C_4$-alkyl, $C_1$-$C_4$-alkoxy, $C_1$-$C_2$-haloalkoxy, $C_1$-$C_2$-haloalkyl, $C_1$-$C_4$-alkoxycarbonyl, carboxyl;

$R^6$ independently of one another represent hydrogen, $C_1$-$C_6$-alkyl, optionally $C_1$-$C_4$-alkyl- or halogen-substituted $C_3$-$C_6$-cycloalkyl, $C_1$-$C_6$-haloalkyl, $C_2$-$C_6$-alkenyl, $C_2$-$C_6$-alkynyl, $C_1$-$C_4$-alkoxy($C_1$-$C_4$)alkyl, hydroxy($C_1$-$C_4$)alkyl, represents aryl or aryl($C_1$-$C_4$)alkyl, each of which is optionally mono- or polysubstituted by identical or different radicals from the group consisting of halogen, cyano, hydroxyl, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylcarbonyl, carboxyl and $C_1$-$C_4$-alkoxycarbonyl, or represents a 3- to 7-membered saturated or unsaturated cycle which may contain no or up to four heteroatoms selected from the group consisting of N, O and S, where two oxygen atoms are not adjacent, and which is unsubstituted or optionally mono- or polysubstituted by identical or different radicals from the group consisting of halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylcarbonyl and $C_1$-$C_4$-alkoxycarbonyl, or, if two radicals $R^6$ are attached to a nitrogen atom, two radicals $R^6$ form a 3- to 7-membered saturated or unsaturated cycle which may contain up to four further heteroatoms selected from the group consisting of N, O and S, where two oxygen atoms are not adjacent, and which is unsubstituted or optionally mono- or polysubstituted by identical or different radicals from the group consisting of halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylcarbonyl and $C_1$-$C_4$-alkoxycarbonyl, or, if two radicals $R^6$ are present in adjacent positions in the grouping $NR^6COR^6$, two radicals $R^6$ form a 3- to 7-membered saturated or unsaturated cycle which may contain up to four further heteroatoms selected from the group consisting of N, O and S, where two oxygen atoms are not adjacent, and which is unsubstituted or optionally mono- or polysubstituted by identical or different radicals from the group consisting of halogen, hydroxyl, $C_1$-$C_4$-alkyl, $C_1$-$C_4$-haloalkyl, $C_1$-$C_4$-alkoxy, $C_1$-$C_4$-haloalkoxy and phenyl, or, if two radicals $R^6$ are attached to a sulphur atom, two radicals $R^6$ form a 5- to 7-membered cycle which may contain up to two further heteroatoms selected from the group consisting of N, O and S, where two oxygen atoms are not adjacent, and which is unsubstituted or optionally $C_1$-$C_4$-alkyl-substituted;

$R^7$ independently of one another represent $C_1$-$C_6$-alkyl, optionally $C_1$-$C_4$-alkyl- or halogen-substituted $C_3$-$C_6$-cycloalkyl, $C_1$-$C_6$-haloalkyl, $C_2$-$C_6$-alkenyl, $C_2$-$C_6$-alkynyl, $C_1$-$C_4$-alkoxy($C_1$-$C_4$)alkyl, hydroxy($C_1$-$C_4$)alkyl, represent aryl or aryl($C_1$-$C_4$)alkyl, each of which is optionally mono- or polysubstituted by identical or different radicals from the group consisting of halogen, cyano, hydroxyl, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylcarbonyl, carboxyl and $C_1$-$C_4$-alkoxycarbonyl, or represent a 3- to 7-membered saturated or unsaturated cycle which may contain no or up to four heteroatoms selected from the group consisting of N, O and S, where two oxygen atoms are not adjacent, and which is unsubstituted or optionally mono- or polysubstituted by identical or different radicals from the group consisting of halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylcarbonyl and $C_1$-$C_4$-alkoxycarbonyl, $R^8$ represents a 3- to 7-membered saturated, unsaturated or aromatic mono- or bicycle which may contain no or up to four heteroatoms selected from the group consisting of N, O and S, where two oxygen atoms are not adjacent, and which is optionally substituted by oxo, hydroxyl, halogen, cyano, $C_1$-$C_4$-alkyl, $C_1$-$C_4$-haloalkyl, $C_1$-$C_4$-alkoxy, $C_1$-$C_4$-haloalkoxy, phenyl, carboxyl, $C_1$-$C_6$-alkylcarbonyl or $C_1$-$C_6$-alkoxycarbonyl;

$R^9$ represents a 3- to 7-membered saturated, unsaturated or aromatic mono- or bicycle which may contain no or up to four heteroatoms selected from the group consisting of N, O and S, where two oxygen atoms are not adjacent, and which is unsubstituted or optionally mono- or polysubstituted by identical or different radicals from the group consisting of $C_1$-$C_4$-alkyl, halogen, cyano, $C_1$-$C_4$-haloalkyl or $C_1$-$C_4$-alkoxy;

m represents a number from 1 to 6, and also the agrochemically active salts thereof, are highly suitable for controlling phytopathogenic fungi and also for reducing mycotoxins in plants and parts of plants.

5-Pyridin-4-yl-1,3-thiazoles of the formula (I) according to the invention and, if appropriate, their salts are highly suitable for controlling phytopathogenic harmful fungi and also for reducing mycotoxins in plants and parts of plants. The compounds according to the invention mentioned above show in particular fungicidal and mycotoxin-reducing activity and can be employed both in crop protection, in the domestic and hygiene field and in the protection of materials.

The formula (I) provides a general definition of the 5-pyridin-4-yl-1,3-thiazoles which can be used according to the invention. Preference is given to using 5-pyridin-4-yl-1,3-thiazoles of the formula (I) in which the radicals have the meanings below.

$R^1$ preferably represents hydrogen, $C_1$-$C_6$-alkyl, $C_1$-$C_4$-haloalkyl, $C_3$-$C_8$-cycloalkyl, aryl($C_1$-$C_4$)alkyl, formyl, ($C_1$-$C_4$-alkyl)carbonyl, ($C_1$-$C_4$-haloalkyl)carbonyl, COOH, ($C_1$-$C_4$-alkoxy)carbonyl, ($C_3$-$C_6$-alkenyloxy)carbonyl, ($C_3$-$C_6$-alkynyloxy)carbonyl, ($C_1$-$C_4$-alkyl)carbamoyl, bis($C_1$-$C_4$-alkyl)carbamoyl, ($C_3$-$C_4$-alkenyl)carbamoyl, ($C_3$-$C_4$-alkynyl)carbamoyl, $CONHR^{10}$, $C_1$-$C_6$-hydroxyalkyl, $C_1$-$C_4$-alkoxy($C_1$-$C_4$)alkyl, phenyloxy($C_1$-$C_4$)alkyl, ($C_1$-$C_4$-alkyl)carbonyloxy($C_1$-$C_4$)alkyl, phenylcarbonyloxy($C_1$-$C_4$)alkyl, ($C_1$-$C_4$-alkyl)sulphanyl($C_1$-$C_4$)alkyl, amino($C_1$-$C_4$)alkyl, ($C_1$-$C_4$-alkyl)amino($C_1$-$C_4$)alkyl, bis($C_1$-$C_4$-alkyl)amino($C_1$-$C_4$)alkyl, piperidin-1-ylethyl, morpholin-1-ylethyl, phenylcarbon-ylamino($C_1$-$C_4$)alkyl, ($C_1$-$C_4$-alkyl)carbonylamino($C_1$-$C_4$)alkyl, $(CH_2)_mN(C_1$-$C_2$-alkyl)$CO(C_1$-$C_4$-alkyl), $(CH_2)_m$COOH, $(CH_2)_m$COO($C_1$-$C_4$)alkyl, $(CH_2)_m$COO($C_3$-$C_5$)alkenyl, $(CH_2)_m$COO($C_3$-$C_5$)alkynyl, $(CH_2)_m$CONH($C_1$-$C_4$)

alkyl, $(CH_2)_mCON((C_1\text{-}C_4\text{-alkyl})_2$, $(CH_2)_mNHCOR^{10}$, $(CH_2)_mOCOR^{10}$, $(CH_2)_mR^{10}$, amino, $NH(C_1\text{-}C_4\text{-alkyl})$, $N(C_1\text{-}C_4\text{-alkyl})_2$, $NH(C_3\text{-}C_5\text{-alkenyl})$, $NH(C_3\text{-}C_5\text{-alkynyl})$, $NH(C_3\text{-}C_6\text{-cycloalkyl})$, $NHR^{10}$, $NH(R^{11})$, $NH(CH_2)_mR^{10}$, $N\!=\!CHN(C_1\text{-}C_4\text{-alkyl})_2$ $N\!=\!C(C_1\text{-}C_2\text{-alkyl})N(C_1\text{-}C_4\text{-alkyl})_2$, $NH(CH_2)_mCOO(C_1\text{-}C_4\text{-alkyl})$, $NHCO(C_1\text{-}C_4\text{-alkyl})$, $NHCO(C_2\text{-}C_5\text{-alkenyl})$, $N(C_1\text{-}C_5\text{-alkyl})CO(C_1\text{-}C_4\text{-alkyl})$, $N(C_3\text{-}C_5\text{-alkenyl})CO(C_1\text{-}C_4\text{-alkyl})$, $N(C_3\text{-}C_5\text{-alkynyl})CO(C_1\text{-}C_4\text{-alkyl})$, $N(R^{10})CO(C_1\text{-}C_4\text{-alkyl})$, $N(Bn)CO(C_1\text{-}C_4\text{-alkyl})$, $NHCO(C_3\text{-}C_6\text{-cycloalkyl})$, $NHCOCH_2(C_3\text{-}C_6\text{-cycloalkyl})$, $NHCO(C_1\text{-}C_5\text{-haloalkyl})$, $NHCO(C_1\text{-}C_4\text{-alkoxy})$, $NHCO(C_1\text{-}C_4\text{-haloalkoxy})$, $NHCO(CH_2)_mCOO(C_1\text{-}C_4\text{-alkyl})$, $NHCOCH_2OH$, $NHCOCH_2OMe$, $NHCOCH(Me)OH$, $NHCOCH_2NMe_2$, $NHCO(CH_2)_mR^{10}$, $NHCOR^{10}$, $N(C_1\text{-}C_4\text{-alkyl})COR^{10}$, $N(C_3\text{-}C_5\text{-alkenyl})CO(R^{10})$, $N(C_3\text{-}C_5\text{-alkynyl})CO(R^{10})$, $NHCONH(C_1\text{-}C_4\text{alkyl})$, $NHCON(C_1\text{-}C_4\text{alkyl})_2$, $NHCONHR^{10}$, $NHCO(R^{11})$, $N(C_1\text{-}C_4\text{-alkyl})CO(R^{11})$;

or $R^1$ preferably represents a saturated or partially saturated heterocycle selected from the group consisting of: pyrrolidine, imidazolidine, oxazolidine, piperidine, piperazine, morpholine, diazepane, each of which is unsubstituted or optionally substituted by oxo, halogen, $C_1\text{-}C_4$-alkyl, $C_1\text{-}C_4$-alkoxy, phenyl, $C_1\text{-}C_4$-alkycarbonyl, $C_1\text{-}C_4$-alkoxycarbonyl or hydroxyl;

or $R^1$ preferably represents a phenyl radical which is optionally mono- or polysubstituted by identical or different radicals from the group consisting of halogen, cyano, hydroxyl, $C_1\text{-}C_4$-alkyl, $C_1\text{-}C_4$-alkoxy, $C_1\text{-}C_4$-haloalkoxy, $C_1\text{-}C_4$-haloalkyl, $C_1\text{-}C_4$-alkylsulphonyl, $C_1\text{-}C_4$-alkylsulphinyl, $C_1\text{-}C_4$-alkylsulphanyl, $C_1\text{-}C_4$-alkylcarbonyl, $C_1\text{-}C_4$-alkoxycarbonyl, carboxyl, carbamoyl, $C_1\text{-}C_4$-alkylcarbamoyl, bis($C_1\text{-}C_4$-alkyl)carbamoyl and $(C_3\text{-}C_4)$alkenylcarbamoyl;

or $R^1$ preferably represents a heteroaromatic selected from the group consisting of: furan, thiophene, thiazole, pyridine, each of which is unsubstituted or optionally substituted by fluorine, chlorine, cyano, $C_1\text{-}C_4$-alkyl, $C_1\text{-}C_4$-alkoxy, $C_1\text{-}C_4$-alkycarbonyl, $C_1\text{-}C_4$-alkoxycarbonyl or hydroxyl;

$R^2$ preferably represents a phenyl or naphthalenyl radical, each of which is optionally mono- or polysubstituted by identical or different radicals from the group consisting of halogen, cyano, hydroxyl, $C_1\text{-}C_6$-alkyl, $C_3\text{-}C_6$-cycloalkyl, $C_1\text{-}C_4$-alkoxy, $(C_1\text{-}C_4)$alkoxy$(C_1\text{-}C_4)$alkyl, benzyloxy, $C_1\text{-}C_4$-haloalkyl, $C_1\text{-}C_4$-haloalkoxy, methanediylbisoxy, difluoromethanediylbisoxy, propane-1,3-diyl, $NH(C_1\text{-}C_4\text{-alkyl})$, $N(C_1\text{-}C_4\text{-alkyl})_2$, $(C_1\text{-}C_4)$alkylsulphanyl, $(C_1\text{-}C_4)$alkoxycarbonyl, carboxyl, or a heteroaromatic selected from the group consisting of: furan, thiophene, pyridine, each of which is unsubstituted or optionally substituted by fluorine, chlorine, $C_1\text{-}C_4$-alkyl or $C_1\text{-}C_4$-alkoxy;

$R^3$ preferably represents hydrogen, fluorine, chlorine, hydroxyl, amino, cyano, $(C_1\text{-}C_4)$alkyl, $(C_1\text{-}C_4)$haloalkyl, $(C_1\text{-}C_4)$alkoxy, hydroxymethyl, cyanomethyl, pyrrolidin-1-ylmethyl, phenylsulphanyl, benzylsulphanyl, phenylsulphonyl, $(C_1\text{-}C_4)$alkoxycarbonyl, $(C_1\text{-}C_4)$alkylcarbamoyl, bis$(C_1\text{-}C_4)$alkylcarbamoyl, $NH(C_1\text{-}C_4\text{-alkyl})$, $N(C_1\text{-}C_4\text{-alkyl})_2$, $NH(C_1\text{-}C_4\text{-haloalkyl})$, $(C_1\text{-}C_2)$alkoxy$(C_1\text{-}C_4)$alkylamino, hydroxy$(C_1\text{-}C_4)$alkylamino, $NH(C_3\text{-}C_5\text{-alkenyl})$, $NH(C_3\text{-}C_5\text{-alkynyl})$, $NH(C_3\text{-}C_6\text{-cycloalkyl})$, $N(C_1\text{-}C_4\text{-alkyl})(C_3\text{-}C_6\text{-cycloalkyl})$, $NH(R^{12})$, $NHCO(C_1\text{-}C_6\text{-alkyl})$, $N(C_1\text{-}C_4\text{-alkyl})CO(C_1\text{-}C_6\text{-alkyl})$, $N(C_3\text{-}C_4\text{-alkenyl})CO(C_1\text{-}C_6\text{-alkyl})$, $N(C_3\text{-}C_4\text{-alkynyl})CO(C_1\text{-}C_6\text{-alkyl})$, $NHCO(C_1\text{-}C_6\text{-haloalkyl})$, $N(C_1\text{-}C_4\text{-alkyl})CO(C_1\text{-}C_6\text{-haloalkyl})$, $N(C_3\text{-}C_4\text{-alkenyl})CO(C_1\text{-}C_6\text{-haloalkyl})$, $N(C_3\text{-}C_4\text{-alkynyl})CO(C_1\text{-}C_6\text{-haloalkyl})$, $NHCO(C_3\text{-}C_6\text{-cycloalkyl})$, $N(C_1\text{-}C_4\text{-alkyl})CO(C_3\text{-}C_6\text{-cycloalkyl})$, $N(C_3\text{-}C_4\text{-alkenyl})CO(C_3\text{-}C_6\text{-cycloalkyl})$, $N(C_3\text{-}C_4\text{-alkynyl})CO(C_3\text{-}C_6\text{-cycloalkyl})$, (2-methylcyclopropyl)carbonylamino, (1-methylcyclohexyl)carbonylamino, $NHCO(C_2\text{-}C_4\text{-alkenyl})$, $NHCOR^{12}$, $N(C_1\text{-}C_4\text{-alkyl})CO(R^{12})$, $N(C_3\text{-}C_4\text{-alkenyl})CO(R^{12})$, $N(C_3\text{-}C_4\text{-alkynyl})CO(R^{12})$, $NHCO(CH_2)_mR^{12}$, $NMeCO(CH_2)_mR^{12}$, $NH(CH_2)_mR^{12}$, $NMe(CH_2)_mR^{12}$, $NHCO(CH_2)_m(C_3\text{-}C_6\text{-cycloalkyl})$, $NH(CH_2)_m(C_3\text{-}C_6\text{-cycloalkyl})$, $NHCOO(C_1\text{-}C_4\text{-alkyl})$, $NHCOO(C_1\text{-}C_4\text{-haloalkyl})$, $NHCONH(C_1\text{-}C_4\text{-alkyl})$, $NHCH(Me)R^{12}$, (thiophen-2-ylcarbonyl)amino, (thiophen-2-ylmethyl)amino, $(C_1\text{-}C_4\text{-alkyl})$sulphonylamino, $(C_3\text{-}C_6\text{-cycloalkyl})$sulphonylamino, or $R^3$ preferably represents a heterocycle selected from the group consisting of: pyrrolidine, piperidine, piperazine, morpholine, each of which is unsubstituted or optionally substituted by oxo, halogen, $(C_1\text{-}C_4)$alkyl;

$R^4$ preferably represents hydrogen, methyl or together with $R^3$ and the pyridine ring to which both are attached forms a bicycle selected from the group consisting of quinolin-4-yl, 1,8-naphthyridin-4-yl, 1H-pyrrolo[2,3-b]pyridin-4-yl, $R^{10}$ preferably represents a phenyl radical which is optionally substituted by halogen, hydroxyl, cyano, $C_1\text{-}C_4$-alkyl, $C_1\text{-}C_4$-alkoxy, $C_1\text{-}C_2$-haloalkoxy, $C_1\text{-}C_2$-haloalkyl, $C_1\text{-}C_4$-alkoxycarbonyl, carboxyl;

$R^{11}$ preferably represents a heteroaromatic selected from the group consisting of furan, thiophene, pyridine, pyrazine which is optionally substituted by fluorine, chlorine, cyano, $C_1\text{-}C_4$-alkyl, $C_1\text{-}C_4$-alkoxy, $C_1\text{-}C_2$-haloalkyl, $C_1\text{-}C_4$-alkoxycarbonyl;

$R^{12}$ preferably represents a phenyl- or naphthalenyl radical which is optionally substituted by halogen, $(C_1\text{-}C_4)$alkyl, $(C_1\text{-}C_4)$alkoxy, $(C_1\text{-}C_4)$haloalkyl;

m preferably represents a number from 1 to 6.

Particular preference is given to compounds of the formula (I) in which one or more symbols have one of the following meanings:

$R^1$ particularly preferably represents hydrogen, $C_1\text{-}C_6$-alkyl, $C_1\text{-}C_2$-haloalkyl, $C_3\text{-}C_6$-cycloalkyl, aryl$(C_1\text{-}C_4)$alkyl, formyl, $(C_1\text{-}C_4\text{-alkyl})$carbonyl, $(C_1\text{-}C_2\text{-haloalkyl})$carbonyl, COOH, $(C_1\text{-}C_4\text{-alkoxy})$carbonyl, $(C_3\text{-}C_4\text{-alkenyloxy})$carbonyl, $(C_3\text{-}C_4\text{-alkynyloxy})$carbonyl, $C_1\text{-}C_6$-hydroxyalkyl, $C_1\text{-}C_4$-alkoxy$(C_1\text{-}C_4)$alkyl, phenoxy$(C_1\text{-}C_4)$alkyl, $(C_1\text{-}C_4\text{-alkyl})$carbonyloxy$(C_1\text{-}C_2)$alkyl, phenylcarbonyloxy$(C_1\text{-}C_2)$alkyl, $(C_1\text{-}C_2\text{-alkyl})$sulphanyl$(C_1\text{-}C_2)$alkyl, amino$(C_1\text{-}C_2)$alkyl, $(C_1\text{-}C_4\text{-alkyl})$amino$(C_1\text{-}C_2)$alkyl, bis$(C_1\text{-}C_4\text{-alkyl})$amino$(C_1\text{-}C_2)$alkyl, piperidin-1-ylethyl, morpholin-1-ylethyl, phenyl carbonyl amino$(C_1\text{-}C_2\text{-})$alkyl, $(C_1\text{-}C_4\text{-alkyl})$carbonylamino$(C_1\text{-}C_2)$alkyl, $(CH_2)_mNMeCO(C_1\text{-}C_4\text{-alkyl})$, $(CH_2)_mCOOH$, $(CH_2)_mCOO(C_1\text{-}C_4\text{-alkyl})$, $(CH_2)_mCOO(C_3\text{-}C_4\text{-alkenyl})$, $(CH_2)_mCOO(C_3\text{-}C_4\text{-alkynyl})$, $(CH_2)_mCONH(C_1\text{-}C_4\text{-alkyl})$, $(CH_2)_mCON((C_1\text{-}C_4)\text{alkyl})_2$, amino, $NH(C_1\text{-}C_4\text{-alkyl})$, $N(C_1\text{-}C_4\text{-alkyl})_2$, $NH(C_3\text{-}C_4\text{-alkenyl})$, $NH(C_3\text{-}C_4\text{-alkynyl})$, $NH(C_3\text{-}C_6\text{-cy-}$ cloalkyl), NHR¹⁰, NH(CH₂)ₘR¹⁰, NH(R¹¹), N=CHN(C₁-C₄-alkyl)₂, N=C(C₁-C₂-alkyl)N(C₁-C₄-alkyl)₂, NH(CH₂)ₘCOO(C₁-C₄-alkyl), NHCO(C₁-C₅-alkyl), NHCO(C₂-C₄-alkenyl), N(C₁-C₅-alkyl)CO(C₁-C₄-alkyl), N(Ph)CO(C₁-C₄-alkyl), N(Bn)CO(C₁-C₄-alkyl), NHCO(C₃-C₆-cycloalkyl), NHCOCH₂(C₃-C₆-cycloalkyl), NHCO(C₁-C₅-haloalkyl), NHCO(C₁-C₄-alkoxy), NHCO(C₁-C₄-haloalkoxy), NHCO(CH₂)ₘCOO(C₁-C₄-alkyl), NHCOCH₂OH, NHCOCH₂OMe, NHCOCH(Me)OH, NHCOCH₂NMe₂, NHCO(CH₂)ₘR¹⁰, NHCOR¹⁰, N(C₁-C₄-alkyl)COR¹⁰, NHCONH(C₁-C₄-alkyl), NHCON(C₁-C₄-alkyl)₂, NHCONHR¹⁰, NHCO(R¹¹);

or

R¹ particularly preferably represents a saturated or partially saturated heterocycle selected from the group consisting of pyrrolidine, imidazolidine, oxazolidine, piperidine, piperazine, morpholine, diazepane, each of which is unsubstituted or optionally substituted by oxo, fluorine, chlorine, C₁-C₄-alkyl, C₁-C₄-alkoxy, phenyl, C₁-C₄-alkylcarbonyl, C₁-C₄-alkoxycarbonyl or hydroxyl;

or

R¹ particularly preferably represents a phenyl radical which is optionally mono- or polysubstituted by identical or different radicals from the group consisting of fluorine, chlorine, bromine, hydroxyl, C₁-C₄-alkyl, C₁-C₄-alkoxy, C₁-C₂-haloalkoxy, C₁-C₂-haloalkyl, C₁-C₂-alkylsulphonyl, C₁-C₂-alkylsulphinyl, C₁-C₂-alkylsulphanyl, C₁-C₄-alkoxycarbonyl, carboxyl, carbamoyl, C₁-C₄-alkylcarbamoyl, bis(C₁-C₄-alkyl)carbamoyl and (C₃-C₄)alkenylcarbamoyl;

or

R¹ particularly preferably represents a heteroaromatic selected from the group consisting of: furan, thiophene, pyridine, each of which is unsubstituted or optionally substituted by fluorine, chlorine, C₁-C₄-alkyl, C₁-C₄-alkoxy, C₁-C₄-alkycarbonyl, C₁-C₄-alkoxycarbonyl or hydroxyl;

R² particularly preferably represents a phenyl or naphthalenyl radical, each of which is optionally mono- or polysubstituted by identical or different radicals from the group consisting of halogen, cyano, hydroxyl, C₁-C₆-alkyl, C₃-C₆-cycloalkyl, C₁-C₄-alkoxy, benzyloxy, C₁-C₄-haloalkyl, C₁-C₄-haloalkoxy, methanediylbisoxy, difluoromethanediylbisoxy, propane-1,3-diyl, NH(C₁-C₄-alkyl), N(C₁-C₄-alkyl)₂, (C₁-C₄)alkylsulphanyl, (C₁-C₄)alkoxycarbonyl, carboxyl, or R² particularly preferably represents a heteroaromatic selected from the group consisting of: furan, thiophene, pyridine, each of which is unsubstituted or optionally substituted by fluorine, chlorine, C₁-C₄-alkyl;

R³ particularly preferably represents hydrogen, fluorine, chlorine, hydroxyl, amino, cyano, (C₁-C₂)alkyl, (C₁-C₂)haloalkyl, (C₁-C₂)alkoxy, hydroxymethyl, cyanomethyl, pyrrolidin-1-ylmethyl, phenylsulphanyl, benzylsulphanyl, phenylsulphonyl, (C₁-C₄)alkoxycarbonyl, NH(C₁-C₄-alkyl), N(C₁-C₄-alkyl)₂, (C₁-C₂)alkoxy(C₁-C₄)alkylamino, NH(C₃-C₄-alkenyl), NH(C₃-C₄-alkynyl), NH(C₃-C₆-cycloalkyl), N(Me)(C₃-C₆-cycloalkyl), NHCO(C₁-C₆-alkyl), NHCO(C₃-C₆-cycloalkyl), (1-methylcyclohexyl)carbonylamino, NHCOR¹², NMeCOR¹², NHCO(CH₂)ₘR¹⁵, NMeCO(CH₂)ₘR¹², NH(CH₂)ₘR¹², NMe(CH₂)ₘR¹², NHCO(CH₂)ₘ(C₃-C₆-cycloalkyl), NH(CH₂)ₘ(C₃-C₆-cycloalkyl), NHCOO(C₁-C₄-alkyl), NHCONH(C₁-C₄-alkyl), NHCH(Me)R¹², (thiophen-2-ylcarbonyl)amino, (thiophen-2-ylmethyl)amino;

or

R³ particularly preferably represents a heterocycle selected from the group consisting of pyrrolidine, piperidine, piperazine, morpholine, each of which is unsubstituted or optionally substituted by methyl;

R⁴ particularly preferably represents hydrogen, methyl or together with R³ and the pyridine ring to which both are attached forms a bicycle selected from the group consisting of quinolin-4-yl, 1,8-naphthyridin-4-yl, 1H-pyrrolo[2,3-b]pyridin-4-yl, R¹⁰ particularly preferably represents a phenyl radical which is optionally substituted by fluorine, chlorine, hydroxyl, cyano, C₁-C₄-alkyl, C₁-C₄-alkoxy, C₁-C₂-haloalkoxy, C₁-C₂-haloalkyl, C₁-C₄alkoxycarbonyl, carboxyl;

R¹¹ particularly preferably represents a heteroaromatic selected from the group consisting of furan, thiophene, pyridine, pyrazine, each of which is optionally substituted by chlorine, methyl, methoxy;

R¹² particularly preferably represents a phenyl- or naphthalenyl radical which is optionally substituted by fluorine, chlorine, methyl, methoxy, trifluoromethyl, m represents a number from 1 to 4.

Very particular preference is given to compounds of the formula (I) in which one or more symbols have one of the following meanings:

R¹ very particularly preferably represents hydrogen,
methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, cyclopropyl, cyclobutyl, cyclopentyl, cyclohexyl, CF₃, CHF₂, CH₂CF₃, CF₂CH₃, benzyl, 2-phenylethyl, 1-phenylethyl, 3-phenylpropyl, formyl, acetyl, propanoyl, 2-methylpropanoyl, trifluoroacetyl, COOH, COOMe, COOEt, COOiPr, COOPr, COOCH₂CH=CH₂, COOCH₂CCH, CHMeOH, CMe₂OH CH₂OH, CH₂OMe, CH₂OEt, CH₂OPh, CH₂CH₂OH, CH₂CH₂OMe, (CH₂)₄OH, (CH₂)₆OH, CH₂OCOCH₃, CH₂OCOC(CH₃)₃, CH₂OCOPh, CHMeOCOPh, CH₂SMe, CH₂CH₂SMe, CH₂NH₂, CH₂NHMe, CH₂NHEt, CH₂NMe₂, CH₂NHiPr, CH₂CH₂NHMe, CH₂CH₂NMe₂, CH₂CH₂NEt₂, piperidin-1-ylethyl, morpholin-1-ylethyl, CH₂NHCOPh, CH₂NHCOMe, CH₂N(Me)COMe, CH₂NHCOEt, CH₂NHCOCH(CH₃)₂, CH₂CH₂NHCOMe, CH₂COOH, CH₂COOMe, CH₂COOEt, CH₂COOiPr, CH₂COOBu, CH₂COOtBu, CH₂COOCH₂CH=CH₂, CH₂COOCH₂CCH, (CH₂)₃COOH, (CH₂)₃COOMe, CH₂CONHMe, CH₂CONMe₂, CH₂CONHtBu, pyrrolidin-1-yl, 2-oxopyrrolidin-1-yl, 2-oxoifnidazolidin-1-yl, 2-oxo-3-phenylimidazolidin-1-yl, 2-oxo-1,3-oxazolidin-3-yl, piperidin-4-yl, 1-methylpiperidin-4-yl, 1-acetylpiperidin-4-yl, 1-t-butyloxycarbonylpiperidin-4-yl, 4-hydroxy-1-methylpiperidin-4-yl, 4-hydroxypiperidin-1-yl, 1-ethoxycarbonylpiperidin-4-yl, 1-methoxycarbonylpiperidin-4-yl, piperidin-1-yl, 4-methylpiperidin-1-yl, 3,5-dimethylpiperidin-1-yl, 2-oxopiperidin-1-yl, 4-methylpiperazin-1-yl, 4-acetylpiperazin-1-yl, 4-phenylpiperazin-1-yl, 4-methoxycarbonylpiperazin-1-yl, morpholin-1-yl, 4-methyl-1,4-diazepan-1-yl, 4-methyl-7-oxo-1,4-diazepan-1-yl, 4,2-dimethyl-7-oxo-1,4-diazepan-1-yl, 4,6,6-trimethyl-7-oxo-1,4-diazepan-1-yl, 4-t-butyloxycarbonyl-6,6-dimethyl-7-oxo-1,4-diazepan-1-yl, 4-t-butyloxycarbonyl-7-oxo-1,4-diazepan-1-yl, phenyl, 4-methylphenyl, 3-methylphenyl, 2-methylphenyl, 3,5-dimethylphenyl, 2,4-dimethylphenyl, 3,4-dimethylphenyl, 4-ethylphenyl, 4-ipropylphenyl, 4-tbutylphenyl, 4-methoxyphenyl, 2-methoxyphenyl, 3-methoxyphenyl, 3,4-dimethoxyphenyl, 3,5-dimethoxyphenyl, 3,4,5-trimethoxyphenyl, 4-ethoxyphenyl, 4-ipropoxyphenyl, 4-trifluoromethoxyphenyl, 4-hydroxyphenyl, 4-fluorophenyl, 2,4-difluorophenyl, 2,6-difluorophenyl, 2-fluorophenyl, 3-fluorophenyl, 2-chlorophenyl, 3-chlorophenyl, 4-chlorophenyl, 3,5-chlorophenyl, 4-bromophenyl, 4-chloro-2-fluorophenyl, 4-trifluoromethylphenyl, 3-trifluoromethylphenyl, 2-fluoro-4-trifluoromethylphenyl, 2-chloro-4-trifluoromethylphenyl, 4-chloro-2-methylphenyl, 2-chloro-6-methylphenyl, 3-fluoro-4-methylphenyl, 3,5-difluoro-4-methylphenyl, 4-methylsulphanylphenyl, 4-methylsulphinylphenyl, 4-methylsulphonylphenyl, 4-carboxyphenyl, 4-methoxycarbonylphenyl, 3-methoxycarbonylphenyl, 4-ethoxycarbonylphenyl, 4-carbamoylphenyl, 4-methylcarbamoylphenyl, 4-ethylcarbamoylphenyl, 4-dimethylcarbamoylphenyl, 4-(prop-2-en-1-ylcarbamoyl)phenyl, furan-2-yl, furan-3-yl, thiophen-2-yl, 5-methylthiophen-2-yl, 5-chlorothiophen-2-yl, thiophen-3-yl, pyridin-2-yl, 6-methoxypyridin-2-yl, 6-methylpyridin-2-yl, pyridin-4-yl, 2-methylpyridin-4-yl, 2-methoxypyridin-4-yl, 2-chloropyridin-4-yl, pyridin-3-yl, 6-methylpyridin-3-yl, 6-chloropyridin-3-yl, $NH_2$, NHMe, NHEt, NHPr, NHiPr, NHBu, NHtBu, $NHCH_2CH=CH_2$, $NHCH_2CCH$, cyclopentylamino, cyclohexylamino, NHBn, 4-chlorobenzylamino, 4-methoxybenzylamino, NHPh, 4-fluorophenylamino, 2-fluorophenylamino, 3,5-dichlorophenylamino, 2-methyl-phenylamino, 4-methylphenylamino, 3-cyanophenylamino, 3-trifluoromethylphenylamino, 4-methoxyphenylamino, 4-trifluoromethoxyphenylamino, pyridin-3-ylamino, pyridin-2-ylamino, $NMe_2$, N(Me)Et, $NEt_2$, $NHCH_2COOEt$, $NHCH_2COOMe$, $NH(CH_2)_2COOEt$, $N=CHNMe_2$, $N=C(Me)NMe_2$, NHCOMe, NHCOEt, NHCOPr, NHCOBu, NHCOtBu, $NHCOCHMe_2$, $NHCOCH_2CHMe_2$, $NHCOCH=CH_2$, acetyl(methyl)amino, acetyl(ethyl)amino, acetyl(propyl)amino, acetyl(ipropyl)amino, acetyl(butyl)amino, acetyl(phenyl)amino, acetyl(pentyl)amino, acetyl(benzyl)amino, cyclopropylcarbonylamino, cyclobutylcarbonylamino, cyclopentylcarbonylamino, cyclohexylcarbonylamino, cyclopentylacetylamino, phenylacetylamino, 3-phenylpropanoylamino, phenylcarbonylamino, methyl(phenylcarbonyl)amino, ethyl(phenylcarbonyl)amino, propyl(phenylcarbonyl)amino, (4-ethylphenylcarbonyl)amino, (2-chlorophenylcarbonyl)amino, (3-chlorophenylcarbonyl)-amino, (4-chlorophenylcarbonyl)amino, (3-methoxycarbonylphenylcarbonyl)amino, (3-carboxyphenylcarbonyl)amino, (2-hydroxyphenylcarbonyl)amino, (4-methoxyphenylcarbonyl)amino, (2,6-dimethylphenylcarbonyl)amino, (4-cyanophenylcarbonyl)amino, (4-methoxycarbonylphenylcarbonyl)amino, (4-methoxycarbonylphenyl)carbonyl(methyl)amino, (4-carboxyphenylcarbonyl)amino, (pyridin-2-ylcarbonyl)amino, (pyridin-3-ylcarbonyl)amino, (pyridin-4-ylcarbonyl)amino, (thiophen-2-ylcarbonyl)amino, (furan-2-ylcarbonyl)amino, (6-chloropyridin-3-ylcarbonyl)amino, (6-methylpyridin-3-ylcarbonyl)amino, (6-methoxypyridin-3-ylcarbonyl)amino, (2-methoxypyridin-3-ylcarbonyl)amino, (pyrazin-2-ylcarbonyl)amino, $NHCOCF_3$, $NHCOCH_2Cl$, $NHCO(CH_2)_3Cl$, $NHCO(CH_2)_4Cl$, $NHCO(CH_2)_5Cl$, $NHCOCH_2OH$, $NHCOCH_2OMe$, NHCOCH(Me)OH, $NHCOCH_2NMe_2$, $NHCOCH_2COOEt$, $NHCOCH_2COOMe$, $NHCO(CH_2)_2COOEt$; $NH(CH_2)_2Ph$, NHCOOMe, NHCOOEt, $NHCOOCH_2CH_2Cl$, $NHCONMe_2$, NHCONHEt, NHCONHPr, NHCONHPh, (2-chlorophenyl)carbamoylamino, (3-chlorophenyl)carbamoylamino, (4-chlorophenyl)carbamoylamino, (2-fluorophenyl)carbamoylamino, (3-fluorophenyl)carbamoylamino, (4-fluorophenyl)carbamoylamino, (2-methylphenyl)carbamoylamino, (3-methylphenyl)carbamoylamino, (4-methylphenyl)carbamoylamino, (3-methoxyphenyl)carbamoylamino, (4-methoxyphenyl)carbamoylamino;

$R^2$ very particularly preferably represents phenyl, naphthalen-1-yl, naphthalen-2-yl, 2,3-dihydro-1H-inden-5-yl 4-chlorophenyl, 3-chlorophenyl, 2-chlorophenyl, 4-fluorophenyl, 3-fluorophenyl, 2-fluorophenyl, 4-bromophenyl, 3-bromophenyl, 3,5-dichlorophenyl, 2,4-difluorophenyl, 2,6-difluorophenyl, 2,4,6-trifluorophenyl, 3,4-dichlorophenyl, 2-chloro-4-fluorophenyl, 3-cyanophenyl, 4-cyanophenyl, 4-hydroxyphenyl, 4-methylphenyl, 3-methylphenyl, 2-methylphenyl, 3,5-dimethylphenyl, 3,4-dimethylphenyl, 4-ethylphenyl, 3-ethylphenyl, 4-propylphenyl, 3-propylphenyl, 4-isopropylphenyl, 4-butylphenyl, 4-t-butylphenyl, 4-hexylphenyl, 4-fluoro-3-methylphenyl, 4-cyclohexylphenyl, 4-methoxyphenyl, 3-methoxyphenyl, 2-methoxyphenyl, 3,4-dimethoxyphenyl, 3,4,5-trimethoxyphenyl, 4-ethoxyphenyl, 4-butoxyphenyl, 4-benzyloxyphenyl, 4-(trifluoromethyl)phenyl, 3-(trifluoromethyl)phenyl, 4-(trifluoromethoxy)phenyl, 1,3-benzodioxol-5-yl, 2,2-difluoro-1,3-benzodioxol-5-yl, 4-(dimethylamino)phenyl, 3-bromo-4-dimethylaminophenyl, 4-(methylsulphanyl)phenyl, 4-methoxycarbonylphenyl, 4-ethoxycarbonylphenyl, 3-methoxycarbonylphenyl, 3-carboxyphenyl, furan-2-yl, 5-methylfuran-2-yl, 3-methylfuran-2-yl, furan-3-yl, thiophen-2-yl, pyridin-2-yl, 5-methylpyridin-2-yl, 6-methylpyridin-2-yl, 5-chloropyridin-2-yl, pyridin-3-yl, pyridin-4-yl;

$R^3$ very particularly preferably represents hydrogen, fluorine, chlorine, hydroxyl, methoxy, cyano, methyl, chloromethyl, hydroxymethyl, cyanomethyl, pyrrolidin-1-ylmethyl, COOMe, COOEt, phenylsulphanyl, benzylsulphanyl, phenylsulphonyl, amino, NHMe, NHEt, NHPr, NHBu, $NHCH_2CH=CH_2$, $NHCH_2CCH$, cyclopropylamino, cyclobutylamino, cyclohexylamino, cyclopentylamino, cyclohexyl(methyl)amino, 4-methylpiperazin-1-yl, piperidin-1-yl, pyrrolidin-1-yl, morpholin-1-yl, $NMe_2$, $NEt_2$, $NHCH_2CH_2OCH_3$, $NHCH(Me)CH_2OCH_3$, NHCOPh, (thiophen-2-ylcarbonyl)amino, (naphthalen-1-ylcarbonyl)amino, NHCOMe, NHCOEt, NHCOtBu, cyclopentylcarbonylamino, cyclohexylcarbonylamino, $NHCO(CH_2)_2CH_3$, $NHCO(CH_2)_3CH_3$, $NHCO(CH_2)_4CH_3$, (1-methylcyclohexyl)carbonylamino, NHCOOtBu, $NHCONHCH_2CH_3$, phenylacetylamino, 3-phenylpropanoylamino, 4-phenylbutanoylamino, 5-phenylpentanoylamino, methyl(phenylacetyl)amino, methyl(3-phenylpropanoyl)amino, (3-(4-fluorophenyl)propanoyl)amino, (3-(4-methoxyphenyl)propanoyl)amino, cyclopentylacetylamino, (cyclohexylmethyl)amino, (cyclopentylmethyl)amino, benzylamino, 2-phenylethylamino, 3-phenylpropylamino, benzyl(methyl)amino, methyl(2-phenylethyl)amino, (R)—NHCH(Me)Ph, (S)—NHCH(Me)Ph, (thiophen-2-ylmethyl)amino, 4-fluorobenzylamino, 4-chlorobenzylamino, 3-chlorobenzylamino, 2-chlorobenzylamino, 4-methoxybenzylamino, 3-methoxybenzylamino, 2-methoxybenzylamino, (naphthalen-2-ylmethyl)amino;

$R^4$ very particularly preferably represents hydrogen or methyl or together with $R^3$ and the pyridine ring to which both are attached forms a bicycle selected from the group consisting of quinolin-4-yl, 1,8-naphthyridin-4-yl, 1H-pyrrolo[2,3-b]pyridin-4-yl.

Very special preference is given to compounds of the formula (I) in which one or more symbols have one of the following meanings:

$R^1$ very especially preferably represents hydrogen, methyl, ethyl, propyl, 1-methylethyl, butyl, 1,1-dimethylethyl, pentyl, cyclohexyl, $CH_2CF_3$, $CF_2CH_3$, benzyl, 2-phenylethyl, 3-phenylpropyl, acetyl, COOH, COOEt, CHMeOH, $(CH_2)_4OH$, $(CH_2)_6OH$, CHMeOCOPh, $CH_2SMe$, $CH_2CH_2SMe$, $CH_2NH_2$, $CH_2NHMe$, $CH_2NHCOPh$, $CH_2COOH$, $CH_2COOEt$, $(CH_2)_3COOH$, $CH_2CONHMe$, 2-oxopyrrolidin-1-yl, 2-oxoimidazolidin-1-yl, 2-oxo-3-phenylimidazolidin-1-yl, 2-oxo-1,3-oxazolidin-3-yl, piperidin-4-yl, 1-methylpiperidin-4-yl, 1-acetylpiperidin-4-yl, 1-t-butyloxycarbonylpiperidin-4-yl, 4-hydroxy-1-methylpiperidin-4-yl, 1-ethoxycarbonylpiperidin-4-yl, 1-methoxy-carbonylpiperidin-4-yl, piperidin-1-yl, 2-oxopiperidin-1-yl, 4-methylpiperazin-1-yl, 4-phenylpiperazin-1-yl, 4-methoxycarbonylpiperazin-1-yl, morpholin-1-yl, phenyl, 4-methylphenyl, 3-methylphenyl, 2-methylphenyl, 4-methoxyphenyl, 2-methoxyphenyl, 4-hydroxyphenyl, 4-fluorophenyl, 2,4-difluorophenyl, 2,6-difluorophenyl, 2-fluorophenyl, 3-fluorophenyl, 2-chlorophenyl, 3-chlorophenyl, 4-chlorophenyl, 4-methylsulphanylphenyl, 4-methylsulphinylphenyl, 4-methylsulphonylphenyl, 4-carboxyphenyl, 4-methoxy-carbonylphenyl, 4-carbamoylphenyl, furan-2-yl, thiophen-2-yl, pyridin-4-yl, pyridin-3-yl, $NH_2$, NHMe, NHEt, NHPr, NHiPr, NHBu, NHBn, NHPh, pyridin-3-ylamino, pyridin-2-ylamino, $NMe_2$, $NEt_2$, $NHCH_2COOEt$, $NH(CH_2)_2COOEt$, N=CHNMe$_2$, N=C(Me)NMe$_2$, NHCOMe, NHCOEt, NHCOPr, NHCOBu, NHCOtBu, NHCOCHMe$_2$, NHCOCH$_2$CHMe$_2$, NHCOCH=CH$_2$, acetyl(methyl)amino, acetyl(ethyl)amino, acetyl(propyl)amino, acetyl(i-propyl)amino, acetyl(butyl)amino, acetyl(phenyl)amino, acetyl(pentyl)amino, acetyl(benzyl)amino, cyclopentylcarbonylamino, cyclohexylcarbonylamino, cyclopentylacetylamino, phenylacetylamino, 3-phenylpropanoylamino, phenylcarbonylamino, methyl(phenylcarbonyl)amino, ethyl(phenylcarbonyl)amino, propyl(phenylcarbonyl)amino, (4-ethylphenylcarbonyl)amino, (2-chlorophenylcarbonyl)amino, (3-chlorophenylcarbonyl)amino, (4-chlorophenylcarbonyl)amino, (3-methoxycarbonyl-phenylcarbonyl)amino, (3-carboxyphenylcarbonyl)amino, (2-hydroxyphenylcarbonyl)amino, (4-methoxyphenylcarbonyl)amino, (2,6-dimethylphenylcarbonyl)amino, (4-cyano-phenylcarbonyl)amino, (4-methoxycarbonylphenylcarbonyl)amino, (4-methoxycarbonyl-phenyl)carbonyl(methyl)amino, (4-carboxyphenylcarbonyl)amino, (pyridin-2-ylcarbonyl)amino, (pyridin-3-ylcarbonyl)amino, (pyridin-4-ylcarbonyl)amino, (thiophen-2-ylcarbonyl)amino, (furan-2-ylcarbonyl)amino, (6-chloropyridin-3-ylcarbonyl)amino, (6-methylpyridin-3-ylcarbonyl)amino, (6-methoxypyridin-3-ylcarbonyl)amino, (2-methoxypyridin-3-ylcarbonyl)amino, (pyrazin-2-ylcarbonyl)amino, NHCOCF$_3$, NHCOCH$_2$Cl, NHCO(CH$_2$)$_3$Cl, NHCO(CH$_2$)$_4$Cl, NHCO(CH$_2$)$_5$Cl, NHCOCH$_2$OH, NHCOCH$_2$OMe, NHCOCH(Me)OH, NHCOCH$_2$NMe$_2$, NHCOCH$_2$COOEt, NHCOCH$_2$COOMe, NHCO(CH$_2$)$_2$COOEt, NHCOOCH$_2$CH$_2$Cl, NH(CH$_2$)$_2$Ph;

$R^2$ very especially preferably represents phenyl, naphthalen-1-yl, 4-chlorophenyl, 3-chlorophenyl, 2-chlorophenyl, 4-fluorophenyl, 3-fluorophenyl, 4-bromophenyl, 3-bromophenyl, 3,5-dichlorophenyl, 3,4-dichlorophenyl, 3-cyanophenyl, 4-hydroxyphenyl, 4-methylphenyl, 3-methylphenyl, 2-methylphenyl, 3,5-dimethylphenyl, 3,4-dimethylphenyl, 4-ethylphenyl, 3-ethylphenyl, 4-propylphenyl, 3-propylphenyl, 4-isopropylphenyl, 4-butylphenyl, 4-t-butylphenyl, 4-hexylphenyl, 4-fluoro-3-methylphenyl, 4-methoxyphenyl, 3-methoxyphenyl, 2-methoxyphenyl, 3,4-dimethoxyphenyl, 3,4,5-trimethoxyphenyl, 4-ethoxyphenyl, 4-butoxyphenyl, 4-benzyloxyphenyl, 4-(trifluoromethyl)phenyl, 3-(trifluoromethyl)phenyl, 4-(trifluoromethoxy)phenyl, 1,3-benzodioxol-5-yl, 4-(dimethylamino)phenyl, 4-(methylsulphanyl)phenyl, furan-2-yl, thiophen-2-yl;

$R^3$ very especially preferably represents hydrogen, fluorine, chlorine, hydroxyl, methyl, chloromethyl, hydroxymethyl, cyanomethyl, pyrrolidin-1-ylmethyl, COOMe, phenylsulphanyl, benzylsulphanyl, phenylsulphonyl, amino, cyclohexylamino, cyclopentylamino, cyclohexyl(methyl)amino, 4-methylpiperazin-1-yl, piperidin-1-yl, pyrrolidin-1-yl, morpholin-1-yl, NHCOPh, (thiophen-2-ylcarbonyl)amino, (naphthalen-1-ylcarbonyl)amino, NHCOMe, NHCOEt, NHCOtBu, cyclopentylcarbonylamino, cyclohexylcarbonylamino, NHCOPr, NHCOBu, NHCO(CH$_2$)$_4$CH$_3$, (1-methylcyclohexyl)carbonylamino, NHCOOtBu, NHCON—HEt, phenylacetylamino, 3-phenylpropanoylamino, 4-phenylbutanoylamino, 5-phenyl-pentanoylamino, methyl(phenylacetyl)amino, methyl(3-phenylpropanoyl)amino, (3-(4-fluorophenyl)propanoyl)amino, (3-(4-methoxyphenyl)propanoyl)amino, cyclopentylacetylamino, (cyclohexylmethyl)amino, (cyclopentylmethyl)amino, benzylamino, 2-phenylethylamino, 3-phenylpropylamino, benzyl(methyl)amino, methyl(2-phenylethyl)amino, (R)—NHCH(Me)Ph, (S)—NHCH(Me)Ph, (thiophen-2-ylmethyl)amino, 4-fluorobenzylamino, 4-chlorobenzylamino, 3-chlorobenzylamino, 2-chlorobenzylamino, 4-methoxybenzylamino, 3-methoxybenzylamino, 2-methoxybenzylamino, (naphthalen-2-ylmethyl)amino;

$R^4$ very especially preferably represents hydrogen, and also to the agrochemically active salts thereof.

The radical definitions mentioned above can be combined with one another as desired. Moreover, individual definitions may not apply.

Particular preference is given to compounds of the formula (I) in which $R^3$ and $R^4$ represent hydrogen.

Particular preference is given to compounds of the formula (I) in which $R^2$ represents halogen- or $C_1$-$C_4$-alkyl-substituted phenyl.

Particular preference is given to compounds of the formula (I) in which $R^2$ represents a thiophene or furan radical which is optionally mono- or polysubstituted by identical or different radicals from the group consisting of halogen, cyano, $C_1$-$C_2$-alkyl, $C_1$-$C_2$-alkoxy, $C_1$-$C_2$-haloalkyl.

Particular preference is given to compounds of the formula (I) in which $R^1$ represents amino.

Particular preference is given to compounds of the formula (I) in which $R^1$ represents substituted phenyl.

Particular preference is given to compounds of the formula (I) in which $R^1$ represents $C_1$-$C_6$-alkyl, $C_1$-$C_4$-haloalkyl or $C_3$-$C_8$-cyclalkyl.

Particular preference is given to compounds of the formula (I) in which $R^3$ represents $N(R^6)_2$, $NR^6COR^6$, $NR^6CO(CH_2)_mR^9$.

The following abbreviations were used:
Me methyl, Et ethyl, Pr n-propyl, iPr methylethyl, Bu n-butyl, iBu 2-methylpropyl, tBu 1,1-dimethylethyl, Ph phenyl, Bn phenylmethyl In the definitions of the symbols given in the formulae above, collective terms were used which are generally representative for the following substituents:

halogen: fluorine, chlorine, bromine and iodine;

aryl: an unsubstituted or optionally substituted 5- to 15-membered partially or fully unsaturated mono-, bi- or tricyclic ring system, where at least one of the rings of the ring system is fully unsaturated, such as, for example (but not limited to), benzene, naphthalene, tetrahydronaphthalene, anthracene, indane, phenanthrene, azulene;

alkyl: saturated, straight-chain or branched hydrocarbon radicals having 1 to 10 carbon atoms, such as, for example (but not limited to), methyl, ethyl, propyl, 1-methylethyl, butyl, 1-methyl-propyl, 2-methylpropyl, 1,1-dimethylethyl, pentyl, 1-methylbutyl, 2-methylbutyl, 3-methyl-butyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, heptyl, 1-methylhexyl, octyl, 1,1-dimethylhexyl, 2-ethylhexyl, 1-ethylhexyl, nonyl, 1,2,2-trimethylhexyl, decyl;

haloalkyl: straight-chain or branched alkyl groups having 1 to 6 carbon atoms (as mentioned abovet), where in these groups some or all of the hydrogen atoms may be replaced by halogen atoms as mentioned above, such as, for example (but not limited to), $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl;

alkenyl: unsaturated, straight-chain or branched hydrocarbon radicals having 2 to 16 carbon atoms and at least one double bond in any position, such as, for example (but not limited to), $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched hydrocarbon groups having 2 to 16 carbon atoms and at least one triple bond in any position, such as, for example (but not limited to), $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

hydroxyalkyl: straight-chain or branched alkyl groups (as mentioned above), where in these groups a hydrogen atom may be replaced by a hydroxyl group, such as, for example (but not limited to), $C_1$-$C_2$-hydroxyalkyl, such as hydroxymethyl, 1-hydroxyethyl or 2-hydroxyethyl;

alkoxy: saturated, straight-chain or branched alkoxy radicals having 1 to 4 carbon atoms, such as, for example (but not limited to), $C_1$-$C_4$-alkoxy, such as methoxy, ethoxy, propoxy, 1-methylethoxy, butoxy, 1-methylpropoxy, 2-methylpropoxy, 1,1-dimethylethoxy;

alkoxyalkyl: an alkoxy group (as mentioned above), which is attached to the skeleton via an alkyl group (as mentioned above), such as, for example (but not limited to), methoxymethyl, methoxyethyl or ethoxyethyl;

haloalkoxy: straight-chain or branched alkoxy groups having 1 to 4 carbon atoms (as mentioned above), where in these groups some or all of the hydrogen atoms may be replaced by halogen atoms as mentioned above, such as, for example (but not limited to), $C_1$-$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorfluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2- fluoroethoxy, 2,2,2-trichloroethoxy, pentafluoroethoxy and 1,1,1-trifluoroprop-2-oxy;

thioalkyl: saturated straight-chain or branched alkylthio radicals having 1 to 6 carbon atoms, such as, for example (but not limited to), $C_1$-$C_6$-alkylthio, such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methyl-pentylthio, 2-methylpentylthio, 3-methylpentylthio, 4-methylpentylthio, 1,1-dimethyl-butylthio, 1,2-dimethylbutylthio, 1,3-dimethylbutylthio, 2,2-dimethylbutylthio, 2,3-dimethyl-butylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

thiohaloalkyl: straight-chain or branched alkylthio groups having 1 to 6 carbon atoms (as mentioned above), where in these groups some or all of the hydrogen atoms may be replaced by halogen atoms as mentioned above, such as, for example (but not limited to), $C_1$-$C_2$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio and 1,1,1-trifluoroprop-2-ylthio;

cycloalkyl: mono-, bi- or tricyclic saturated hydrocarbon groups having 3 to 12 carbon ring members, such as, for example (but not limited to), cyclopropyl, cyclobutyl, cyclopentyl and cyclohexyl, bicyclo[1.0.1]butane, decalinyl, norbornyl;

cycloalkenyl: mono-, bi- or tricyclic non-aromatic hydrocarbon groups having 5 to 15 carbon ring members and at least one double bond, such as, for example (but not limited to), cyclopenten-1-yl, cyclohexen-1-yl, cyclohepta-1,3-dien-1-yl, norbornen-1-yl;

alkylcarbonyl: an alkyl group having 1 to 4 carbon atoms (as mentioned above) which is attached to the skeleton via a carbonyl group (—CO—);

(alkoxy)carbonyl: an alkoxy group having 1 to 4 carbon atoms (as mentioned above) which is attached to the skeleton via a carbonyl group (—CO—);

haloalkylcarbonyl: a haloalkyl group having 1 to 4 carbon atoms (as mentioned above) which is attached to the skeleton via a carbonyl group (—CO—);

arylalkyl: an aryl group (as mentioned above) which is attached to the skeleton via an alkyl group (as mentioned above), such as, for example (but not limited to), benzyl, 1-phenylethyl, 2-phenylethyl;

aryloxy: an aryl group (as mentioned above) which is attached to the skeleton via an oxygen atom;

alkylcarbonyloxy: an alkyl group (as mentioned above) which is attached to the skeleton via a carbonyloxy group (—(C=O)O—), such as, for example (but not limited to), acetyloxy, propanoyloxy, butanoyloxy, (2-methylpropanoyl)oxy;

arylcarbonyloxy: an aryl group (as mentioned above) which is attached to the skeleton via a carbonyloxy group (—(C=O)O—);

heterocycle: a three- to fifteen-membered saturated or partially unsaturated heterocycle which contains one to four heteroatoms from the group consisting of oxygen, nitrogen and sulphur: mono-, bi- or tricyclic heterocycles which, in addition to carbon ring members, contain one to three nitrogen atoms and/or one oxygen or sulphur atom or one or two oxygen and/or sulphur atoms; if the ring contains a plurality of oxygen atoms, these are not directly adjacent; such as, for example (but not limited to), oxiranyl, aziridinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-hydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl;

hetaryl: an unsubstituted or optionally substituted 5- to 15-membered partially or fully unsaturated mono-, bi- or tricyclic ring system where at least one of the rings of the ring system is fully unsaturated and which contains one to four heteroatoms from the group consisting of oxygen, nitrogen and sulphur, if the ring contains a plurality of oxygen atoms, these are not directly adjacent; such as, for example (but not limited to), 5-membered hetaryl which contains one to four nitrogen atoms or one to three nitrogen atoms and one sulphur or oxygen atom: 5-membered heteroaryl groups which, in addition to carbon atoms, may contain one to four nitrogen atoms or one to three nitrogen atoms and one sulphur or oxygen atom as ring members, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

benzo-fused 5-membered hetaryl which contains one to three nitrogen atoms or one nitrogen atom and one oxygen or sulphur atom: 5-membered heteroaryl groups which, in addition to carbon atoms, may contain one to four nitrogen atoms or one to three nitrogen atoms and one sulphur or oxygen atom as ring members and in which two adjacent carbon ring members or one nitrogen and one adjacent carbon ring member may be bridged by a buta-1,3-diene-1,4-diyl group in which one or two carbon atoms may be replaced by nitrogen atoms; for example benzindolyl, benzimidazolyl, benzothiazolyl, benzopyrazolyl, benzofuryl;

5-membered hetaryl which contains one to four nitrogen atoms and is attached via nitrogen or benzo-fused 5-membered hetaryl which contains one to three nitrogen atoms and is attached via nitrogen: 5-membered heteroaryl groups which, in addition to carbon atoms, may contain one to four nitrogen atoms or one to three nitrogen atoms as ring members and in which two adjacent carbon ring members or one nitrogen and one adjacent carbon ring member may be bridged by a buta-1,3-diene-1,4-diyl group in which one or two carbon atoms may be replaced by nitrogen atoms, where these rings are attached to the skeleton via one of the nitrogen ring members, for example 1-pyrrolyl, 1-pyrazolyl, 1,2,4-triazol-1-yl, 1-imidazolyl, 1,2,3-triazol-1-yl, 1,3,4-triazol-1-yl;

6-membered hetaryl which contains one to three or one to four nitrogen atoms: 6-membered heteroaryl groups which, in addition to carbon atoms, may contain, respectively, one to three and one to four nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Not included are combinations which are against natural laws and which the person skilled in the art would therefore exclude based on his/her expert knowledge. Ring structures having three or more adjacent oxygen atoms, for example, are excluded.

Depending on the nature of the substituents defined above, the compounds of the formula (I) may have acidic or basic properties and may form salts, if appropriate also inner salts or adducts, with inorganic or organic acids or with bases or with metal ions.

Suitable metal ions are, in particular, the ions of the elements of the second main group in particular calcium and magnesium, the third and fourth main group, in particular aluminium, tin and lead, ans also of the first to eighth transition group, in particular chromium, manganese, iron, cobalt, nickel, copper, zinc and others. Particular preference is given to the metal ions of the elements of the fourth period. Here, the metals can be present in the various valencies that they can assume.

If the compounds of the formula (I) carry hydroxyl or carboxyl groups or other groups which induce acidic properties, these compounds can be reacted with bases to give salts.

Suitable bases are, for example, hydroxides, carbonates, bicarbonates of the alkali and alkaline earth metals, in particular those of sodium, potassium, magnesium and calcium, furthermore ammonia, primary, secondary and tertiary amines having ($C_1$-$C_4$)alkyl radicals, mono-, di- and trialkanolamines of ($C_1$-$C_4$)alkanols, choline and also chlorocholine.

If the compounds of the formula (I) carry amino or alkylamino groups or other groups which induce basic properties, these compounds can be reacted with acids to give salts.

Examples of inorganic acids are hydrohalic acids, such as hydrogen fluoride, hydrogen chloride, hydrogen bromide and hydrogen iodide, sulphuric acid, phosphoric acid and nitric acid, and also acidic salts, such as $NaHSO_4$ and $KHSO_4$.

Suitable organic acids are, for example, formic acid, carbonic acid and alkanoic acids, such as acetic acid, trifluoroacetic acid, trichloroacetic acid and propionic acid, and also glycolic acid, thiocyanuric acid, lactic acid, succinic acid, citric acid, benzoic acid, cinnamic acid, oxalic acid, alkylsulphonic acids (sulphonic acids having straight-chain or branched alkyl radicals having 1 to 20 carbon atoms), arylsulphonic acids or -disulphonic acids (aromatic radicals such as phenyl and naphthyl which carry one or two sulphonic acid groups), alkylphosphonic acids (phosphonic acids having straight-chain or branched alkyl radicals having 1 to 20 carbon atoms), arylphosphonic acids or -diphosphonic acids (aromatic radicals such as phenyl and naphthyl which carry one or two phosphonic acid radicals), where the alkyl or aryl radicals may carry further substituents, for example p-toluenesulphonic acid, salicylic acid, p-aminosalicylic acid, 2-phenoxybenzoic acid, 2-acetoxybenzoic acid etc.

The salts obtainable in this manner likewise have fungicidal and mycotoxin-reducing properties.

The 5-pyridin-4-yl-1,3-thiazoles which can be used according to the invention can be prepared in a known manner (cf. WO99/21555, WO99/64418, JP05070446, WO01/30778, WO01/74811, WO02/062792, WO2000/64894 WO2001/10865, WO2007/077574, WO2006/137658, WO2004/089937, WO2005/063743, WO2007/076348, Chem. Pharm. Bull. 2005, 53, 410-418, J. Med. Chem. 2005, 48, 5966, J. Med. Chem. 2004, 47, 4494; Bioorg. Med. Chem. Lett. 2000, 10, 1261; Bioorg. Med. Chem. Lett. 2004, 14, 3595).

The invention also provides compounds of the formula (Ia)

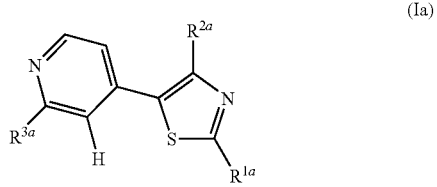

(Ia)

in which $R^{1a}$ represents optionally hydroxyl-, amino-, cyano-, halogen-, $OR^{6a}$-, $SR^{6a}$-, $C_1$-$C_4$-haloalkoxy-, $R^{5a}$-, $R^{9a}$-, $C_1$-$C_4$-alkylsulphinyl-, $C_1$-$C_4$-alkylsulphonyl-substituted $C_1$-$C_6$-alkyl, or represents optionally $C_1$-$C_4$alkyl-, cyano- or halogen-substituted $C_3$-$C_5$-cycloalkyl, $R^{2a}$ represents naphthyl, phenyl, phenyl which is mono- or polysubstituted by fluorine, $CF_3$ or cyano, and also 4-methylphenyl, 3,4-dimethylphenyl, 4-cyanophenyl, 3-cyanophenyl, 4-chlorophenyl, 3,4-dichlorophenyl, 3,5-dichlorophenyl, 3-methyl-4-fluorophenyl, 3-cyano-4-fluorophenyl or represents a thiophene radical which is optionally mono- or polysubstituted by identical or different radicals from the group consisting of halogen, cyano, $C_1$-$C_1$-alkyl, $C_1$-$C_4$alkoxy, $C_1$-$C_4$haloalkyl;

$R^{3a}$ represents hydrogen, halogen, cyano, $C_1$-$C_6$-alkyl, $C_1$-$C_4$-haloalkyl, $(CH_2)_m CN$, $(CH_2)_m N(R^{6a})_2$, $(CH_2)_m N(R^{6a})COR^{6a}$, $COOR^{6a}$, $CON(R^{6a})_2$, $N(R^{6a})_2$, $NR^{5a}R^{6a}$, $NR^{6a}COR^{5a}$, $NR^{6a}COR^{6a}$, $N(COR^{6a})_2$, $NR^{6a}COR^{9a}$, $NR^{6a}COR^{11a}$, $NR^{6a}CSR^{5a}$, $NR^{6a}CSR^{6a}$, $NR^{6a}CSR^{9a}$, $NR^{6a}COOR^{7a}$, $N(COOR^{7a})_2$, $NR^{6a}CON(R^{6a})_2$, $NR^{6a}SO_2R^{5a}$, $NR^{6a}SO_2R^{6a}$, $N=CR^{6a}N(R^{6a})_2$, $NR^{6a}CO(CH_2)_m R^{9a}$, or $NR^{6a}(CH_2)_m R^{9a}$, $R^{5a}$ represents a phenyl radical which is optionally substituted by halogen, hydroxyl, cyano, $C_1$-$C_4$-alkyl, $C_1$-$C_4$-alkoxy, $C_1$-$C_2$-haloalkoxy, $C_1$-$C_2$-haloalkyl, $C_1$-$C_4$-alkoxycarbonyl or carboxyl;

$R^{6a}$ independently of one another represent hydrogen, $C_1$-$C_6$-alkyl, optionally $C_1$-$C_4$-alkyl- or halogen-substituted $C_3$-$C_6$-cycloalkyl, $C_1$-$C_6$-haloalkyl, $C_2$-$C_6$-alkenyl, $C_2$-$C_6$-alkynyl, $C_1$-$C_4$-alkoxy($C_1$-$C_4$)alkyl, hydroxy($C_1$-$C_4$)alkyl, amino($C_1$-$C_4$)alkyl, represent aryl($C_1$-$C_4$)alkyl which is optionally mono- or polysubstituted by identical or different radicals from the group consisting of halogen, cyano, hydroxyl, $C_1$-$C_4$-alkyl, $C_1$-$C_4$-haloalkyl, $C_1$-$C_4$-alkoxy, $C_1$-$C_4$-haloalkoxy, if two radicals $R^{6a}$ are attached to a nitrogen atom, two radicals $R^{6a}$ form a 3- to 7-membered saturated or unsaturated cycle which may contain up to four further heteroatoms selected from the group consisting of N, O and S, where two oxygen atoms are not adjacent, and which is unsubstituted or optionally mono- or polysubstituted, preferably up to trisubstituted, by identical or different radicals from the group consisting of halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylcarbonyl and $C_1$-$C_4$-alkoxycarbonyl, or if two radicals $R^{6a}$ are present in adjacent positions in the grouping $NR^{6a}COR^{6a}$, two radicals $R^{6a}$ form a 3- to 7-membered saturated or unsaturated cycle which may contain up to four further heteroatoms selected from the group consisting of N, O and S, where two oxygen atoms are not adjacent, and which is unsubstituted or optionally mono- or polysubstituted, preferably up to trisubstituted, by identical or different radicals from the group consisting of halogen, hydroxyl, $C_1$-$C_4$-alkyl, $C_1$-$C_4$-haloalkyl, $C_1$-$C_4$-alkoxy and $C_1$-$C_4$-haloalkoxy, $R^{7a}$ independently of one another represent $C_1$-$C_6$-alkyl, optionally $C_1$-$C_4$-alkyl- or halogen-substituted $C_3$-$C_6$-cycloalkyl, $C_1$-$C_6$-haloalkyl, $C_2$-$C_6$-alkenyl, $C_2$-$C_6$-alkynyl, $C_1$-$C_4$-alkoxy($C_1$-$C_4$)alkyl, hydroxy($C_1$-$C_4$) alkyl, $R^{9a}$ represents a 3- to 7-membered saturated or partially unsaturated carbocycle which is unsubstituted or optionally mono- or polysubstituted by identical or different radicals from the group consisting of $C_1$-$C_4$-alkyl, halogen, cyano, $C_1$-$C_4$-haloalkyl and $C_1$-$C_4$-alkoxy, $R^{11a}$ represents a five- or six-membered heteroaromatic which may contain up to three heteroatoms selected from the group consisting of N, O and S, where two oxygen atoms are not adjacent, and which is optionally substituted by halogen, cyano, $C_1$-$C_4$-alkyl, $C_1$-$C_4$-alkoxy, $C_1$-$C_2$-haloalkyl, $C_1$-$C_4$-alkoxycarbonyl, m represents a number from 1 to 6, and also the agrochemically active salts thereof, except for compounds of the formula (Ia) in which $R^{1a}$ represents ethyl, $R^{2a}$ represents 3-trifluoromethylphenyl, thiophen-2-yl or 4-fluoro-3-methylphenyl and $R^{3a}$ represents $NH_2$, NHAc, NHCOEt, NHCOPh;

and also compounds in which $R^{1a}$ represents ethyl, $R^{2a}$ represents phenyl or 4-chlorophenyl and $R^{3a}$ represents hydrogen, $NH_2$, NHAc, NHCOEt, NHCOPh, NHCOCH$_2$Ph, NHCOCH$_2$cPen or NHCOOtBu;

and also compounds in which $R^{1a}$ represents ethyl, $R^{2a}$ a represents 3-fluorophenyl and $R^{3a}$ represents amino, NHAc, NHCOEt, NHCOCH$_2$Ph;

and also compounds in which $R^{1a}$ represents ethyl, $R^{2a}$ represents 4-methylphenyl or 3-cyanophenyl and $R^{3a}$ represents hydrogen, amino, NHCOPh or NHCOCH$_2$Ph;

and also compounds in which $R^{1a}$ represents ethyl, $R^{2a}$ represents 4-fluorophenyl and $R^{3a}$ represents amino, NHAc, NHCOEt, NHCOPh, NHCOCH$_2$Ph, NHcHex or fluorine.

The formula (Ia) provides a general definition of the compounds according to the invention. Preferred radical definitions of the formulae mentioned above and below are given below. These definitions apply to the end products of the formula (Ia) and likewise to all intermediates.

Preference is given to compounds of the formula (Ia) in which $R^{1a}$ represents $C_1$-$C_6$-alkyl, represents cyano- or $R^{9a}$-substituted $C_1$-$C_4$-alkyl, optionally $C_1$-$C_2$-alkyl- or halogen-substituted $C_3$-$C_5$-cycloalkyl, $C_1$-$C_4$-haloalkyl, $C_1$-$C_4$-alkyloxy($C_1$-$C_4$)alkyl, hydroxy($C_1$-$C_4$)alkyl, optionally halogen-, methyl- or cyano-substituted aryl ($C_1$-$C_4$)alkyl, $(CH_2)_m S(C_1$-$C_4$)alkyl, $R^{2a}$ represents naphthyl, phenyl, 2-fluorophenyl, 3-fluorophenyl, 4-fluorophenyl, 2,5-difluorophenyl, 2,4-difluorophenyl, 2,6-difluorophenyl, 3,5-difluorophenyl, 2,4,6-trifluorophenyl, 3,4-difluorophenyl, 3,4,5-trifluorophenyl, 3-trifluoromethylphenyl, 4-trifluoromethylphenyl, 4-methylphenyl, 3,4-dimethylphenyl, 4-cyanophenyl, 3-cyanophenyl, 4-chlorophenyl, 3,4-dichlorophenyl, 3,5-dichlorophenyl, 3-methyl-4-fluorophenyl, 3-cyano-4-fluorophenyl or represents a thiophene radical which is optionally mono- or polysubstituted by identical or different radicals from the group consisting of halogen, cyano, $C_1$-$C_2$-alkyl, $C_1$-$C_2$-alkoxy, $C_2$-haloalkyl;

$R^{1a}$ represents hydrogen, halogen, cyano, $C_1$-$C_4$-alkyl, $COO(C_1$-$C_4$-alkyl), $CON(C_1$-$C_4$-alkyl)$_2$, $CONH(C_1$-$C_4$-alkyl), $CONH(C_3$-$C_6$-cycloalkyl), $CONH(C_3$-$C_6$-alkenyl), $CONH(C_3$-$C_6$-alkynyl), $(CH_2)_m CN$, $(CH_2)_m NHCO(C_1$-$C_4$-alkyl), $(CH_2)_m N(C_1$-$C_4$-alkyl)CO(C_1$-$C_4$-alkyl), $(CH_2)_m N(C_3$-$C_6$-cycloalkyl)CO(C_1$-$C_4$-alkyl), $(CH_2)_m N(C_3$-$C_6$-alkenyl)CO(C_1$-$C_4$-alkyl), $(CH_2)_m N(C_1$-$C_4$-alkynyl)CO(C_1$-$C_4$-alkyl), $NH_2$, $NH(C_1$-$C_4$-alkyl), $NHR^{5a}$, NHCH(Me)R$^{5a}$, $NH(CH_2)_m R^{5a}$, pyrrolidin-1-yl, $NH(C_3$-$C_6$-cycloalkyl), $NH(C_1$-$C_4$-haloalkyl), $NH(C_3$-$C_6$-alkenyl), $NH(C_3$-$C_6$-alkynyl), NHCH(Me)CH$_2$OMe, NHCH(Me)CH$_2$OH, NHCH$_2$CH(Me)OMe, NHCH$_2$CH(Me)OH, NHCOH, NHCO($C_1$-$C_6$-alkyl), NHCO(CH$_2$)$_m$O($C_1$-$C_4$-alkyl), NHCOCHMeOMe, NHCO($C_1$-$C_4$-haloalkyl), NHCOCHMeOH, NHCOCHMeNH$_2$, NHCOCH$_2$NH$_2$, $N(C_1$-$C_4$-alkyl)CO($C_1$-$C_4$-alkyl), $N(C_3$-$C_6$-cycloalkyl) CO($C_1$-$C_4$-alkyl), $N(C_3$-$C_6$-alkenyl)CO($C_1$-$C_4$-alkyl), $N(C_3$-$C_6$-alkynyl)CO($C_1$-$C_4$-alkyl), NHCOR$^{9a}$, NHCO(CH$_2$)$_m$R$^{9a}$, N($C_1$-$C_4$-alkyl)COR$^{9a}$, N($C_3$-$C_6$-cycloalkyl)COR$^{9a}$, N($C_3$-$C_6$-alkenyl)COR$^{9a}$, N($C_1$-$C_4$-alkynyl)COR$^{9a}$, N(CO($C_1$-$C_4$-alkyl))$_2$ NHCOC($C_2$-$C_6$-alkenyl), N($C_1$-$C_4$-alkyl)CO($C_2$-$C_6$-alkenyl), N($C_3$-$C_6$-cycloalkyl)CO($C_2$-$C_6$-alkenyl), N($C_3$-$C_6$-alkenyl)CO($C_2$-$C_6$-alkenyl), N($C_3$-$C_6$-alkynyl)CO($C_2$-$C_6$-alkenyl), NHCOR$^{5a}$, NHCO(CH$_2$)$_m$R$^{5a}$, NHCOR$^{11a}$, N($C_1$-$C_4$-alkyl)COR$^{5a}$, N($C_3$-$C_6$-alkenyl)COR$^{5a}$, N($C_3$-$C_6$-alkynyl)COR$^{5a}$, NHCOO($C_1$-$C_4$-alkyl), NCOO($C_1$-$C_4$-alkyl)$_2$, N($C_1$-$C_4$-alkyl)COO($C_1$-$C_4$-alkyl), N($C_3$-$C_6$-alkenyl)COO($C_1$-$C_4$-alkyl), N($C_3$-$C_6$-alkynyl)COO($C_1$-$C_4$-alkyl), N($C_3$-$C_6$-cycloalkyl)COO($C_1$-$C_4$-alkyl), NHCS($C_1$-$C_4$-alkyl), NHCSR$^{9a}$, NHCSR$^{5a}$, NHSO$_2$($C_1$-$C_4$-alkyl), NSO$_2$($C_1$-$C_4$-alkyl)$_2$, NHSO$_2$($C_3$-$C_6$-cycloalkyl), R$^{5a}$ represents a phenyl radical which is optionally mono- or polysubstituted by identical or different radicals from the group consisting of methyl, fluorine, chlorine, methoxy and cyano, R$^{9a}$ represents a 3- to 6-membered saturated carbocycle which is unsubstituted or mono- or poly-substituted by identical or different radicals from the group consisting of methyl, fluorine, chlorine, cyano, R$^{11a}$ represents a heteroaromatic which is selected from the group consisting of furan, thiophene, pyridine and pyrazine and which is optionally substituted by fluorine, chlorine, cyano, methyl, OMe;

m represents a number from 1 to 4, and also the agrochemically active salts thereof, except for compounds of the formula (Ia) in which R$^{1a}$ represents ethyl, R$^{2a}$ represents 3-trifluoromethylphenyl, thiophen-2-yl or 4-fluoro-3-methylphenyl and R$^{3a}$ represents NH$_2$, NHAc, NHCOEt, NHCOPh;

and also compounds in which

R$^{1a}$ represents ethyl,

R$^{2a}$ represents phenyl or 4-chlorophenyl and

R$^{3a}$ represents hydrogen, NH$_2$, NHAc, NHCOEt, NHCOPh, NHCOCH$_2$Ph, NHCOCH$_2$cPen or NHCOOtBu;

and also compounds in which

R$^{1a}$ represents ethyl,

R$^{2a}$ represents 3-fluorophenyl and

R$^{3a}$ represents amino, NHAc, NHCOEt, NHCOCH$_2$Ph;

and also compounds in which

R$^{1a}$ represents ethyl,

R$^{2a}$ represents 4-methylphenyl or 3-cyanophenyl and

R$^{3a}$ represents hydrogen, amino, NHCOPh or NHCOCH$_2$Ph;

and also compounds in which,

R$^{1a}$ represents ethyl,

R$^{2a}$ represents 4-fluorophenyl and

R$^{3a}$ a represents amino, NHAc, NHCOEt, NHCOPh, NHCOCH$_2$Ph, NHcHex or fluorine.

Particular preference is given to compounds of the formula (Ia) in which

R$^{1a}$ represents methyl, ethyl, 1-methylethyl, propyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, cyclopropyl, 1-methylcyclopropyl, 2-methylcyclopropyl, 1-chlorocyclopropyl, 2-chlorocyclopropyl, cyclobutyl, cyclopentyl, (cyclopropyl)methyl, difluoromethyl, 2-fluoroethyl, 2,2-difluoroethyl, 1,1-difluoroethyl, 2,2,2-trifluoroethyl, methoxymethyl, 2-methoxyethyl, 1-methoxyethyl, 1-hydroxyethyl, benzyl, 2-fluorobenzyl, 2-cyanobenzyl, 2-phenylethyl, 1-phenylethyl, 1-(2-fluorophenyl)ethyl, cyanomethyl, 2-cyanoethyl, CH$_2$SMe, CH$_2$CH$_2$SMe, R$^{2a}$ represents phenyl, 2-fluorophenyl, 3-fluorophenyl, 4-fluorophenyl, 2,5-difluorophenyl, 2,4-difluorophenyl, 2,6-difluorophenyl, 2,4,6-trifluorophenyl, 3-trifluoromethylphenyl, 4-trifluoromethylphenyl, 4-methylphenyl, 3,4-dimethylphenyl, 4-cyanophenyl, 3-cyanophenyl, 4-chlorophenyl, 4-fluoro-3-methylphenyl, 3-cyano-4-fluorophenyl, thiophen-2-yl, 5-chlorothiophen-2-yl, thiophen-3-yl, 5-methylthiophen-3-yl, R$^{3a}$ represents hydrogen, fluorine, chlorine, cyano, methyl, CON(Me)Et, CONHMe, CONHcPr, CONHCH$_2$CH=CH$_2$, CONHCH$_2$CCH, CH$_2$CN, CH$_2$NHAc, CH$_2$N(Me)Ac, CH$_2$N(cPr)Ac, CH$_2$N(CH$_2$CH=CH$_2$)Ac, CH$_2$N(CH$_2$CCH)Ac, NH$_2$, NHMe, NHEt, NHiPr, NHPh, NHBn, NHCH(Me)Ph, NHCH$_2$CH$_2$Ph, pyrrolidin-1-yl, NHcPr, NHcPen, NHCH$_2$CHF$_2$, NHCH$_2$CH=CH$_2$, NHCH$_2$CCH, NHCH(Me)CH$_2$OMe, NHCOCH$_2$Cl, NHCH(Me)CH$_2$OH, NHCH$_2$CH(Me)OMe, NHCH$_2$CH(Me)OH, NHCOH, NHAc, NHCOEt, NHCOPr, NHCOiPr, NHCOtBu, NHCOsecBu, NHCOiBu, NHCOCH$_2$OMe, NHCOCHMeOMe, NHCOCF$_3$, NHCOCH$_2$CF$_3$, NHCOCH$_2$Cl, NHCOCHMeOH, NHCOCHMeNH$_2$, NHCOCH$_2$NH$_2$, N(Me)Ac, N(cPr)Ac, N(CH$_2$CH=CH$_2$)Ac, N(CH$_2$CCH)Ac, N(Ac)$_2$ NHCOcPr, (1-methylcyclopropylcarbonyl)amino, (2-methylcyclopropylcarbonyl)amino, (1-chlorocyclopropylcarbonyl)amino, (2-fluorocyclopropylcarbonyl)amino, (2-chlorocyclopropylcarbonyl)amino, NHCOcBu, NHCOcHex, (cyclopropylmethylcarbonyl)amino, N(Me)COcPr, N(cPr)COcPr, N(CH$_2$CH=CH$_2$)COcPr, N(CH$_2$CCH)COcPr, NHCOC(Me)=CH$_2$, NHCOPh, NHCOCH$_2$Ph, NHCOCH$_2$CH$_2$Ph, (4-methylbenzoyl)amino, (4-fluorobenzoyl)amino, (4-methoxybenzoyl)amino, (thiophen-2-ylcarbonyl)amino, (thiophen-3-ylcarbonyl)amino, N(Me)COPh, N(CH$_2$CH=CH$_2$)COPh, N(CH$_2$CCH)COPh, NHCOOMe, NHCOOEt, NHCOOiPr, N(COOiPr)$_2$, NHCOOtBu, N(Me)COOMe, N(CH$_2$CH=CH$_2$)COOMe, N(CH$_2$CCH)COOMe, N(cPr)COOMe, NHCSMe, NHCSEt, NHCSiPr, NHCScPr, NHCSPh, NHSO$_2$Me, N(SO$_2$Me)$_2$, NHSO$_2$cPr, and also the agrochemically active salts thereof, except for compounds of the formula (Ia) in which R$^{1a}$ represents ethyl, R$^{2a}$ represents 3-trifluoromethylphenyl, thiophen-2-yl or 4-fluoro-3-methylphenyl and R$^{3a}$ represents NH$_2$, NHAc, NHCOEt, NHCOPh;

and also compounds in which

R$^{1a}$ represents ethyl,

R$^{2a}$ represents phenyl or 4-chlorophenyl and

R$^{3a}$ represents hydrogen, NH$_2$, NHAc, NHCOEt, NHCOPh, NHCOCH$_2$Ph or NHCOOtBu;

and also compounds in which

R$^{1a}$ represents ethyl,

R$^{2a}$ represents 3-fluorophenyl and

R$^{3a}$ represents amino, NHAc, NHCOEt, NHCOCH$_2$Ph;

and also compounds in which

R$^{1a}$ represents ethyl,

R$^{2a}$ represents 4-methylphenyl or 3-cyanophenyl and

R$^{3a}$ represents hydrogen, amino, NHCOPh or NHCOCH$_2$Ph;

and also compounds in which
$R^{1a}$ represents ethyl,
$R^{2a}$ represents 4-fluorophenyl and
$R^{1a}$ represents amino, NHAc, NHCOEt, NHCOPh, $NHCOCH_2Ph$ or fluorine.

Very particular preference is given to compounds of the formula (Ia) in which
$R^{1a}$ represents methyl, ethyl, 1-methylethyl, butyl, 1,1-dimethylethyl, cyclopropyl, difluoromethyl, benzyl,
$R^{2a}$ represents phenyl, 4-fluorophenyl, 3-trifluoromethylphenyl, 3,4-dimethylphenyl, thiophen-2-yl, 5-chlorothiophen-2-yl,
$R^{3a}$ represents hydrogen, fluorine, chlorine, methyl, CON(Me)Et, CONHcPr,
$NH_2$, NHEt, NHiPr, NHPh, NHBn, NHCH(Me)Ph, $NHCH_2CH_2Ph$, pyrrolidin-1-yl, NHcPr, NHcPen, $NHCH_2CHF_2$, $NHCH_2CH=CH_2$, NHCH(Me)$CH_2OMe$, $NHCH(Me)CH_2OH$, $NHCH_2CH(Me)$OMe, $NHCH_2CH(Me)OH$,
NHAc, NHCOEt, NHCOPr, NHCOiPr, NHCOtBu, NHCOsecBu, NHCOiBu, $NHCOCH_2OMe$, $NHCOCH_2Cl$,
NHCOcPr, (1-methylcyclopropylcarbonyl)amino, (2-methylcyclopropylcarbonyl)amino, NHCOcBu, NHCOcHex, $NHCOC(Me)=CH_2$,
N(Me)Ac, N(cPr)Ac, $N(Ac)CH_2CCH$, $N(Ac)_2$
NHCOPh, $NHCOCH_2Ph$, $NHCOCH_2CH_2Ph$, (4-methylbenzoyl)amino, (4-fluorobenzoyl)amino, (4-methoxybenzoyl)amino, (thiophen-2-ylcarbonyl)amino, (thiophen-3-ylcarbonyl)amino, N(Me)COPh
NHCOOMe, NHCOOEt, NHCOOiPr, $N(COOiPr)_2$, NHCOOtBu,
$NHSO_2Me$, $N(SC_2Me)_2$,
and also the agrochemically active salts thereof, except for compounds of the formula (Ia) in which
$R^{1a}$ represents ethyl,
$R^{2a}$ represents 3-trifluoromethylphenyl, thiophen-2-yl and
$R^{3a}$ represents $NH_2$, NHAc, NHCOEt, NHCOPh;
and also compounds in which
$R^{1a}$ represents ethyl,
$R^{2a}$ represents phenyl and
$R^{3a}$ represents hydrogen, $NH_2$, NHAc, NHCOEt, NHCOPh, $NHCOCH_2Ph$, or NHCOOtBu;
and also compounds in which
$R^{1a}$ represents ethyl,
$R^{2a}$ represents 4-fluorophenyl and
$R^{3a}$ represents amino, NHAc, NHCOEt, NHCOPh, $NHCOCH_2Ph$ or fluorine.

The radical definitions given above can be combined with one another as desired. Moreover, individual definitions may not apply.

Particular preference is given to compounds of the formula (Ia) in which $R^{3a}$ represents hydrogen, where the other substituents have one or more of the meanings mentioned above, and to the agrochemically active salts thereof.

Particular preference is given to compounds of the formula (Ia) in which $R^{2a}$ represents phenyl, 4-methylphenyl, 4-fluorophenyl and 4-chlorophenyl, where the other substituents have one or more of the meanings mentioned above, and to the agrochemically active salts thereof.

Particular preference is given to compounds of the formula (Ia) in which $R^{2a}$ represents a thiophene radical which is optionally mono- or polysubstituted by identical or different radicals from the group consisting of halogen, cyano, $C_1$-$C_2$-alkyl, $C_1$-$C_2$-alkoxy, $C_1$-$C_2$-haloalkyl; very particular preference is given to thiophen-2-yl, 5-chlorothiophen-2-yl, thiophen-3-yl, 5-methylthiophen-3-yl; where the other substituents have one or more of the meanings mentioned above, and to the agrochemically active salts thereof.

Particular preference is given to compounds of the formula (Ia) in which $R^{1a}$ represents $C_1$-$C_4$-alkyl, $C_1$-$C_4$-haloalkyl or $C_3$-$C_5$-cycloalkyl, where the other substituents have one or more of the meanings mentioned above, and to the agrochemically active salts thereof.

Particular preference is given to compounds of the formula (Ia) in which $R^{3a}$ represents $NR^{6a}COR^{5a}$ or $NR^{6a}COR^{11a}$, where the other substituents have one or more of the meanings mentioned above, and to the agrochemically active salts thereof.

Particular preference is given to compounds of the formula (Ia) in which $R^{3a}$ represents $NR^{6a}COR^{6a}$, $NR^{6a}COR^{9a}$ or $NR^{6a}CO(CH_2)_m R^{9a}$, where the other substituents have one or more of the meanings mentioned above, and to the agrochemically active salts thereof.

The pyridinylthiazoles of the general formula (Ia) according to the invention can be prepared by various routes, as shown schematically below. Unless indicated otherwise, the radicals mentioned have the meanings given above.

The pyridinylthiazoles of the general formula (Ia) according to the invention can be prepared by Process A according to the scheme below (Scheme A):

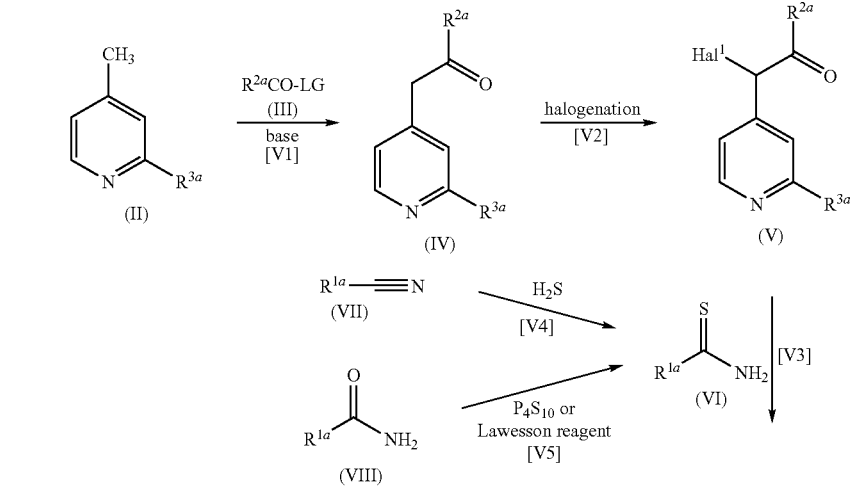

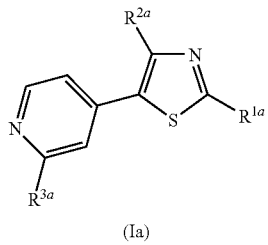

(Ia)

What is described is a process for preparing compounds according to formula (Ia) where. in a first step [V1], a compound of the formula (II)

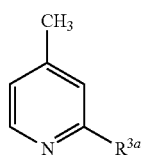

(II)

is reacted with $R^{2a}$CO-LG in the presence of a base to give a compound of the formula (IV)

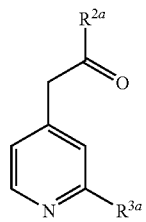

(IV)

which, in a second step [V2], is reacted in the presence of a halogenating agent to give a compound according to formula (V)

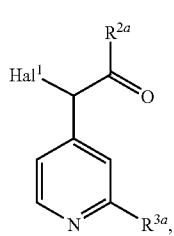

(V)

whereupon the compound of the formula (V) formed is, in a third step [V3], reacted with a compound of the formula (VI),

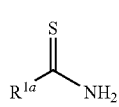

(VI)

formed by reacting the compounds of the formula (VII)

(VII)

with compounds of the formula (VIII)

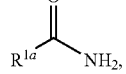

(VIII)

either in a step [V4] in the presence of hydrogen sulphide or alternatively in a step [V5] in the presence of $P_4S_{10}$ or Lawesson reagent, to give the compounds of the formula (Ia) according to the invention.

LG is selected from the group consisting of alkoxy, cyano, dialkylamino, N(alkyl)-Oalkyl; preferably, LG represents methoxy, ethoxy and N(Me)OMe; $Hal^1$ is selected from the group consisting of chlorine, bromine, iodine. In the formulae (II), (III), (IV), (V), (VI), (VII), (VIII), $R^{1a}$, $R^{2a}$ and $R^{3a}$ generally, preferably, particularly preferably and very particularly preferably have those meanings which have already been mentioned in connection with the description of the compounds of the formula (Ia) according to the invention as being preferred, particularly preferred and very particularly preferred, respectively, for these radicals.

Compounds of the general formula (IV) are either commercially available or can be prepared by condensation of 4-methylpyridines of the general formula (II) with compounds of the general formula $R^{2a}$CO-LG (III) in the presence of a base. 4-Methylpyridines of the general formula (II) are either commercially available or can be obtained, for example, from the corresponding 4-halopyridines (for example analogously to Chemistry-Eur. J. 2009, 15, 4165-4171; Tetrahedron 1997, 53, 13749-13756; J. Org. Chem. 1985, 50, 5405-9). Carboxylic acid derivatives of the general formula (III) are commercially available or can be prepared by customary methods of organic synthesis from the analogous carboxylic acids. By halogenation, it is possible to obtain the compounds of the general formula (V) from compound (IV). The subsequent reaction of compounds of the formula (V) with thiamides of the general formula (VI) affords the pyridinylthiazoles of the formula (Ia) according to the invention. The thiamides of the general formula (VI) used are either commercially available or can be prepared by methods known from the literature from the nitriles of the formula (VII) or from the carboxamides of the formula (VIII).

Process Step [V1] from Scheme A:

Compounds of the general formula (IV) are either commercially available or can be prepared by processes known from the literature (for example Chem. Pharm. Bull. 2005, 53, 410-418) by condensation of compounds of the general formula (II) with a carboxylic ester, a carbonitrile, a dialkylcarboxamide or N,O-dialkylamide of the general formula $R^{2a}$CO-LG (III) in the presence of suitable bases, if appropriate in the presence of a solvent.

Suitable bases for carrying out the Process step V1 according to the invention from Scheme A are alkali metal alkaloxides (for example KOtBu, NaOtBu), alkali metal amides (for example sodium amides, lithium diisopropylamide, lithium bis(trimethylsilyl)amide) or metal hydrides (for example KH, NaH).

Suitable for use as solvents for carrying out the Process step VI according to the invention from Scheme A are all solvents which are inert under the reaction conditions, and also mixtures thereof. Preference is given to cyclic and acyclic ethers (for example diethyl ether, tetrahydrofuran, dimethoxyethane) and also amides (for example dimethylformamide, dimethylacetamide).

The reaction temperature for carrying out the Process step V1 according to the invention from Scheme A is between −78° C. and the boiling point of the solvent, preferably between −78° C. and room temperature.

The reaction time for carrying out the Process step V1 according to the invention from Scheme A is, depending on the scale of the reaction, between 5 min and 24 h, preferably between 30 min and 3 h. Carboxylic acid derivatives of the general formula (III) are commercially available or can be prepared by customary methods of organic synthesis from the analogous carboxylic acids.

Process Step [V2] from Scheme A:

As described in an exemplary manner for bromine in acetic acid in *Chem. Pharm. Bull.* 2005, 53, 410-418, by using suitable halogenating agents such as, for example, elemental chlorine, bromine, iodine or N-halosuccinimides (NCS, NBS, NIS) or else sulphuryl chloride and pyridinium tribromide, it is possible to obtain the compounds of the general formula (V, Hal$^1$=chlorine, bromine, iodine) from compound (IV).

The halogenation for carrying out the Process step V2 according to the invention from Scheme A can be carried out in the presence of a solvent which is inert under the reaction conditions. Preference is given to alcohols (for example methanol, ethanol), cyclic and acyclic ethers (for example diethyl ether, tetrahydrofuran, dioxane), amides (for example dimethylformamide, dimethylacetamide), sulphoxides (for example dimethyl sulphoxide), aromatic hydrocarbons (for example benzene, toluene), halogenated hydrocarbons (for example dichloromethane, chloroform) and also carboxylic acids (for example acetic acid).

The reaction temperature for carrying out the Process step V2 according to the invention is between 0° C. and the boiling point of the solvent, preferably between room temperature and 80° C. The reaction time for carrying out the Process step V2 according to the invention is, depending on the scale of the reaction, between 5 min and 24 h, preferably between 30 min and 6 h.

Process Step [V3] from Scheme A:

The reaction of the halocarbonyls (V) with thiamides of the general formula (VI), if appropriate in the presence of a base and a solvent, affords the pyridinylthiazoles (Ia) according to the invention.

Suitable bases for carrying out the Process step V3 according to the invention from Scheme A can be alkali metal carbonates (for example sodium carbonate, potassium carbonate, caesium carbonate, sodium bicarbonate), alkali metal phosphates (for example disodium hydrogenphosphate), aromatic amines (for example pyridine, lutidine) or tertiary amines (triethylamine, ethyldiisopropylamine, N-methylpiperidine, N-methylmorpholine).

Suitable solvents for carrying out the Process step V3 according to the invention from Scheme A are all solvents which are inert under the reaction conditions, and also mixtures thereof. Preference is given to alcohols (for example methanol, ethanol), cyclic and acyclic ethers (for example diethyl ether, tetrahydrofuran, dimethoxyethane), amides (for example dimethylformamide, dimethylacetamide), sulphoxides (for example dimethyl sulphoxide) and nitriles (for example acetonitrile).

The reaction temperature for carrying out the Process step V3 according to the invention from Scheme A is between 0° C. and the boiling point of the solvent, preferably between room temperature and 100° C. The reaction time for carrying out the Process step V3 according to the invention from Scheme A is, depending on the scale of the reaction, between 5 min and 72 h, preferably between 30 min and 24 h.

Process Steps [V4] and [V5] from Scheme A:

The thiamides of the general formula (VI) used are either commercially available or can be prepared by methods known from the literature, for example by reacting a nitrile (VII) with hydrogen sulphide, if appropriate in the presence of a suitable base (for example triethylamine, described in *Tetrahedron*, 1989, 45, 7329-40.) and a suitable solvent (for example chloroform, dimethylformamide, pyridine, methanol, ethanol) or by thionation of a carboxamide (VIII) using phosphorus pentasulphide (cf. WO2007/039177) or Lawesson reagent (cf. *Tetrahedron*, 1985, 41, 2567-624) in the presence of a suitable solvent such as, for example, benzene, toluene, pyridine, tetrahydrofuran or dioxane.

Alternatively, the pyridinylthiazoles of the general formula (Ia) according to the invention can also be prepared by Process B (Schema B):

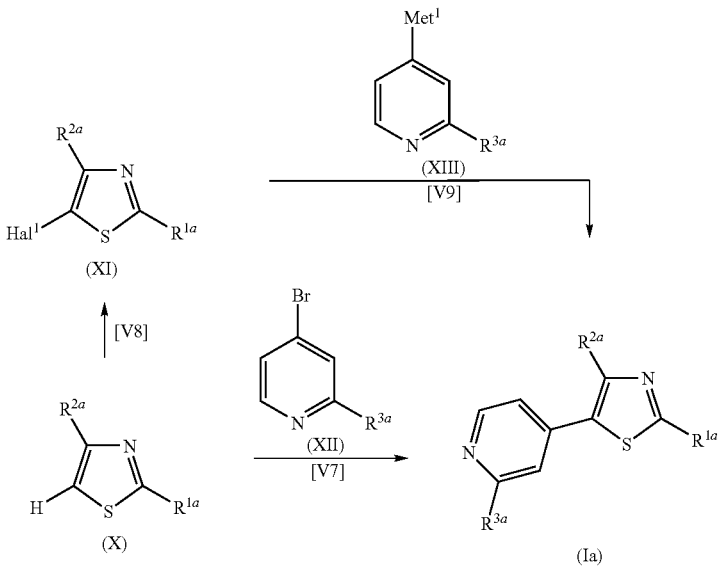

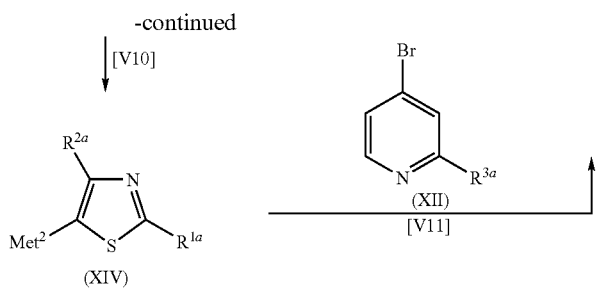

In Scheme B, Met¹ represents B(OR*)₂, Sn(alkyl)₃ and Met²=B(OR*)₂, where OR* represents hydroxyl or OiPr or (OR*)₂ represents pinacol. Preferably, Met¹=B(OH)₂ or 4,4,5,5-tetramethyl-1,3,2-dioxaborolan-2-yl. Hal¹ represents Cl, Br, I.

In the formulae (IX), (X), (XI), (XII), (VI), (XIV) and (XIII), $R^{1a}$, $R^{2a}$ and $R^{3a}$ generally, preferably, particularly preferably and very particularly preferably have those meanings which have already been mentioned in connection with the description of the compounds of the formula (Ia) according to the invention as being preferred, particularly preferred and very particularly preferred, respectively, for these radicals.

5-H-Thiazoles of the general formula (X) can be obtained by reacting thiamides of the general formula (VI) with halomethylcarbonyls of the general formula (IX). They can be reacted directly with 4-bromopyridines of the general formula (XII) in a Heck reaction to give the pyridinylthiazoles (Ia) according to the invention. Alternatively, these 5-H-thiazoles (X) can initially be reacted selectively at the 5-position to give the compounds of the formula (XI) and furthermore be reacted in a Suzuki or Stille reaction with pyridines of the general formula (XIII) to give the desired pyridinylthiazoles of the formula (Ia). It is also possible to prepare from compounds of the formula (X) the boronic acids or boronic esters of the formula (XIV) and to convert these in a Suzuki reaction with 4-bromopyridines of the formula (XII) into compounds of the formula (Ia).

Process Step [V6] from Scheme B:

5-H-Thiazoles of the general formula (X) can be obtained by reacting thiamides of the general formula (VI) with halomethylcarbonyls of the general formula (IX) analogously to Process step [V3] from Process A (described, for example, in *J. Med. Chem.* 2008, 51, 6110-6120). The halomethylcarbonyls (IX) are either commercially available or can be obtained using suitable halogenating agents (for example bromine, NBS, NCS) from corresponding acetophenones (cf. *Synthesis*, 2008, 253-266) or by Friedel-Crafts acylation using, for example, chloroacetyl chloride (cf. *J. Org. Chem.* 1985, 50, 5612-15) from the corresponding (hetero)aromatics.

Process Step [V7] from Scheme B:

The 5-H-thiazoles of the general formula (X) can be reacted Pd-catalyzed in the presence of a suitable base with 4-bromopyridines of the general formula (XII) to give the pyridinylthiazoles (Ia) according to *J. Org. Chem.*, 2009, 74, 1179-86.

Preference is given to palladium catalysts in which the palladium is present in oxidation state (0) or (II), such as, for example, tetrakis(triphenylphosphine)palladium, bis(dibenzylideneacetone)-palladium, palladium(II) acetate, palladium(II) chloride.

The catalyst for carrying out the Process step V7 according to the invention from Scheme B may contain phosphorus-containing ligands, or phosphorus-containing ligands may be added separately to the reaction mixture. Suitable phosphorus-containing ligands are, preferably, tri-n-alkylphosphanes, triarylphosphanes, dialkylarylphosphanes, alkyldiarylphosphanes and/or heteroarylphosphanes, such as tripyridylphosphane and trifurylphosphane, where the three substituents at phosphorus may be identical or different and where one or more substituents may link the phosphorus groups of a plurality of phosphanes. Particular preference is given to phosphanes such as triphenylphosphane, tri-tert-butylphosphane, tricyclohexylphosphane.

Suitable bases for carrying out the Process step V7 according to the invention from Scheme B are alkali metal carbonates (for example K₂CO₃), alkali metal acetates (for example KOAc), and also tertiary amines (for example triethylamine).

Suitable solvents for carrying out the Process step V7 according to the invention from Scheme B for the Heck reaction are all customary solvents which are inert under the reaction conditions, such as cyclic and acyclic ethers (dimethoxymethane, tetrahydrofuran, dioxane), aromatic hydrocarbons (for example toluene), nitriles (for example acetonitrile, propionitrile) and amides (for example dimethylformamide, dimethylacetamide, N-methylpyrrolidone), or the reaction can be carried out in mixtures of two or more of these solvents.

The reaction temperature for carrying out the Process step V7 according to the invention from Scheme B is between 50-150° C. and the reaction time between 3 h and 24 h.

Process Step [V8] from Scheme B:

Analogously to Process step [V2], 5-H-thiazoles of the general formula (X) can be halogenated at the 5-position to give XI (Hal¹=Cl, Br, I; described for example in *Eur. J. Org. Chem.*, 2002, 13, 2126-2135).

Process Step [V9] from Scheme B:

A further alternative for synthesizing the pyridinylthiazoles (Ia) according to the invention is provided by Process step [V9]. In a Suzuki reaction (for example analogously to WO2006/109084), the 5-halothiazoles (XI) obtained in Process step [V8] are reacted with pyridines of the general formula (XIII). The 4-pyridinylboronic acids and esters (XIII, Met¹=B(OR*)₂) employed for the Suzuki reaction are commercially available or can be prepared from the corresponding 4-bromopyridines (XII) by Pd-catalyzed reaction with bispinacolatodiborane (for example *Bioorg. Med. Chem. Lett.* 2006, 16, 1277-1281) or by metallation/boration (for example *Synthesis*, 2004, 4, 469-483).

Suitable solvents for the Suzuki reaction are all customary solvents which are inert under the reaction conditions, such as alcohols (for example ethanol, ethylene glycol), cyclic and acyclic ethers (dimethoxymethane, tetrahydrofuran, dioxane), aromatic hydrocarbons (for example toluene), ketones (for example acetone, ethyl methyl ketone), nitriles (for example acetonitrile, propionitrile) and amides (for example dimethylformamide, dimethylacetamide, N-methylpyrrolidone) and water, or the reaction can be carried out in mixtures of two or more of these solvents. The preferred solvents are dioxane or tetrahydrofuran.

Suitable bases for carrying out the Process step V9 according to the invention from Scheme B are alkali metal hydroxides, alkali metal carbonates, alkali metal bicarbonates, alkali metal acetates, alkali metal alkoxides, and also tertiary amines. Preferred bases are caesium carbonate, sodium carbonate, potassium carbonate or potassium acetate.

Preferred for carrying out the Process step V9 according to the invention are palladium catalysts in which the palladium is present in oxidation state (0) or (II), such as, for example, tetrakis(triphenylphosphine)palladium, bis(triphenylphosphine)palladium dichloride and bis(diphenylphosphino)ferrocenepalladium dichloride or else palladium(II) acetate and palladium(I) chloride.

The catalyst for carrying out the Process step V9 according to the invention may contain phosphorus-containing ligands, or phosphorus-containing ligands may be added separately to the reaction mixture. Suitable phosphorus-containing ligands are, preferably, tri-n-alkylphosphanes, triarylphosphanes, dialkylarylphosphanes, alkyldiarylphosphanes and/or heteroarylphosphanes, such as tripyridylphosphane and trifurylphosphane, where the three substituents at phosphorus may be identical or different and where one or more substituents may link the phosphorus groups of a plurality of phosphanes, where a metal atom may also be part of this linkage. Particular preference is given to phosphanes such as triphenylphosphane, tri-tert-butylphosphane, tricyclohexylphosphane.

The Suzuki coupling in the practice of the Process step V9 according to the invention is carried out in a temperature range of from 25° to 200° C., particularly preferably at from 80° to 150° C. The reaction time for carrying out the Process step V9 according to the invention varies depending on the scale of the reaction and the reaction temperature, but is generally between a few minutes and 48 hours.

In an alternative C—C coupling method for Process step [V9], the halothiazoles (XI) can also be converted in a Stille reaction (for example analogously to *Synthesis,* 2008, 3099-3107) with pyridinyl-stannanes (XIII, Met$^1$=Sn(alkyl)$_3$) into the pyridinylthiazoles (Ia). The preparation of 4-pyridinylstannanes (XIII) is likewise known from the literature (for example *J. Med. Chem.* 2003, 46, 284-302; *Tetrahedron* 2004, 60, 6113-6120). For the Stille coupling, the choice of a catalyst, if appropriate an inorganic or organic halide salt, if appropriate a ligand and a suitable solvent at suitable temperatures may vary depending on the tin alkyl substrate used.

Suitable solvents for the Stille coupling are all customary solvents which are inert under the reaction conditions, such as cyclic and acyclic ethers (for example dimethoxymethane, tetrahydrofuran, dioxane), aromatic hydrocarbons (for example toluene), amides (for example dimethylformamide, di-methylacetamide, N-methylpyrrolidone) and sulphoxides (for example dimethyl sulphoxide), or the reaction can be carried out in mixtures of two or more of these solvents.

Halide salts used with preference are, for example, copper halides (for example CuBr or CuI), caesium halides (for example CsF) and tetraalkylammonium halides (for example TBAF).

Preference is given to palladium catalysts in which the palladium is present in oxidation state (0) or (II), such as, for example, tetrakis(triphenylphosphine)palladium, bis(triphenylphosphine)palladium dichloride and bis(diphenylphosphino)ferrocenepalladium dichloride, or else palladium(II) acetate and palladium(II) chloride.

The catalyst may contain phosphorus-containing ligands, or phosphorus-containing ligands may be added separately to the reaction mixture. Suitable phosphorus-containing ligands are, preferably, tri-n-alkylphosphanes, triarylphosphanes, dialkylarylphosphanes, alkyldiarylphosphanes and/or heteroarylphosphanes, such as tripyridylphosphane and trifurylphosphane, where the three substituents at phosphorus may be identical or different and where one or more substituents may link the phosphorus groups of a plurality of phosphanes, where a metal atom may also be part of this linkage. Particular preference is given to phosphanes such as triphenylphosphane, tri-tert-butylphosphane, tricyclohexylphosphane.

The Stille coupling is carried out in a temperature range of 25°-200° C., particularly preferably at 60°-150° C. The reaction time varies depending on the scale of the reaction and the reaction temperature, but is generally between a few minutes and 48 hours.

Process Steps [V10] and [V11] from Scheme B:

Alternatively, it is possible to prepare the thiazoleboronic acids or esters (XIV) from the compound (X) under Ir-catalysis (cf. WO2007/1371074) or via a metallation/boronation step (cf. *J. Org. Chem.,* 2006, 71, 3754-3761), and to convert the product in a Suzuki reaction analogously to Process step [V9] with 4-bromopyridines (XII) into compounds (Ia). The 4-bromopyridines (XII) required for this purpose are either commercially available or can be obtained, for example, by methods known from the literature from the corresponding N-oxides (*Bioorg. Med. Chem. Lett.* 2009, 19, 2244-2248), 4-nitropyridines (*Chem. Pharm. Bull.* 1990, 38, 2446-58), 4-aminopyridines (*J. Prak. Chem.,* 1959, 9, 164-72) or 4-chloropyridines (*Eur. J. Org. Chem.,* 2002, 24, 4181-4184).

Alternatively to Processes A and B from Scheme A and Scheme B, starting with pyridinylthiazoles of the general formula (Ib) ($R^{3a}$=H), it is possible, by Process C, to prepare further pyridinylthiazoles of the general formulae (Ic to Ij) according to the invention (Scheme C):

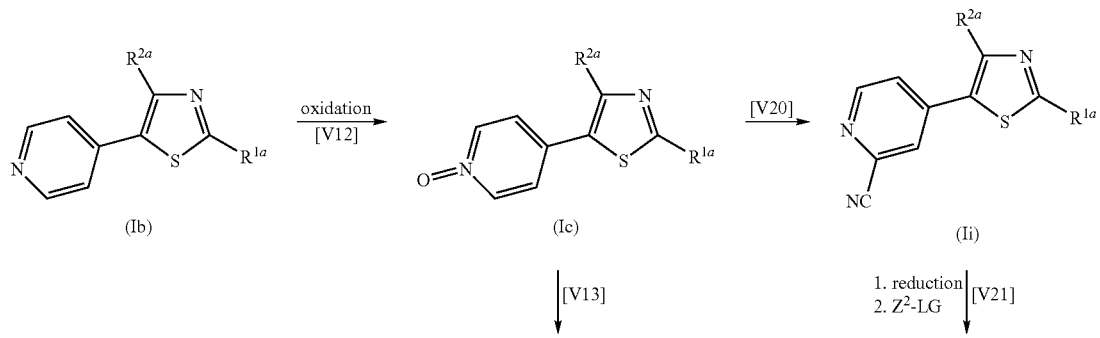

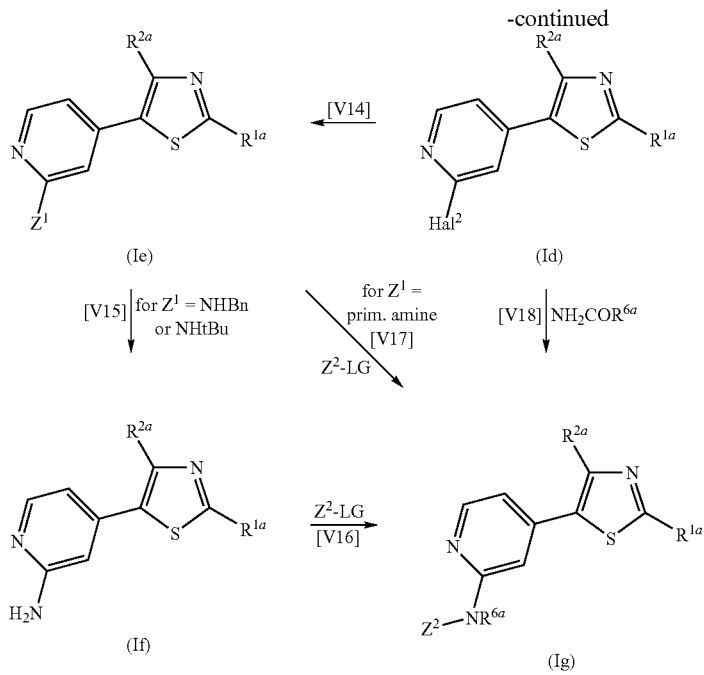
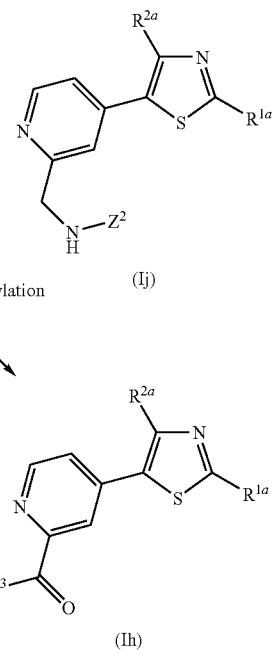

Z¹ represents N(R$^{6a}$)$_2$, preferably represents NHBn, NHtBn or a primary amine. Z² represents R'CO, R''COO and R'''SO$_2$, where R' represents R$^{5a}$, R$^{6a}$, R$^{9a}$ and R$^{11a}$, R'' represents R$^{7a}$, R''' represents R$^{5a}$ and R$^{6a}$. Z³ represents N(R$^{6a}$)$_2$ and OR$^{6a}$. Hal² represents chlorine a bromine, LG represents halogen, hydroxyl and OZ². In the formulae (Ib), (Ic), (Id), (Ie), (If), (Ig), (Ih), (Ii) and (Ij), R$^{1a}$, R$^{2a}$, R$^{5a}$, R$^{6a}$, R$^{9a}$ and R$^{11a}$ generally, preferably, particularly preferably and very particularly preferably have those meanings which have already been mentioned in connection with the description of the compounds of the formula (Ia) according to the invention as being preferred, particularly preferred and very particularly preferred, respectively, for these radicals.

To this end, the pyridinylthiazoles of the general formula (Ib) (R$^{3a}$=H) can be oxidized to the corresponding N-oxides (Ic) and then be halogenated to (Id). The halogen atom can furthermore be exchanged for N-nucleophiles, which gives compounds of the general formula (Ie). For Z¹=NHBn or NHtBu, the benzyl or tBu radical can be removed selectively in acidic media, giving (2-aminopyridin-4-yl)thiazoles (If). Alternatively, compounds of the general formula (If) can also be prepared by a method known from the literature (*J. Med. Chem*, 2005, 48, 5966-5979) according to Process A from tert-butyl (4-methylpyridin-2-yl)carbamate.

Starting with (If), using suitable carboxylic acid derivatives, it is possible to prepare the corresponding amides (Ig, where Z²=R'CO), using chloroformates, it is possible to prepare the corresponding carbamates (Ig, where Z²=R''COO) and using sulphonyl chlorides or sulphonic anhydrides, it is possible to prepare the corresponding sulphonamides (Ig, where Z²=R'''SO$_2$). As described, for example, in DE102006037399 an amide radical can also be introduced directly under Pd catalysis from the 2-halopyridines (Id).

Pd-catalyzed carbonylations of (Id) in the presence of alcohols afford the corresponding esters of the general formula (Ih, where Z³=OR$^{6a}$), whereas in the presence of amines the corresponding amides (Ih, where Z³=N(R$^{6a}$)$_2$) are formed.

2-Cyanopyridines (Ii) can be obtained from the N-oxides. Subsequent catalytic hydrogenation of the cyano function allows acylation of the amino function with Z²-LG, giving compounds of the general formula (b).

Process Step [V12] from Scheme C:

Using suitable oxidizing agents, the pyridinylthiazoles of the general formula (Ib) (R$^{3a}$=H) can be oxidized to the corresponding N-oxides (Ic), as described, for example, in *Chem. Pharm. Bull.* 2005, 53, 410-418.

Suitable oxidizing agents for carrying out the Process step V12 according to the invention from Scheme C are hydrogen peroxide, hydrogen peroxide with catalytic amounts of methyltrioxorhenium, peracids (for example m-chloroperoxybenzoic acid) or dimethyldioxirane. The oxidations are, if appropriate, carried out in halogenated hydrocarbons (for example dichloromethane), amides (for example dimethylformamide), ketones (for example acetone), nitriles (for example acetonitrile) or acids (acetic acid) as solvent.

The N-oxide formation for carrying out the Process step V12 according to the invention from Scheme C is carried out in a temperature range of from 0° to 110° C. The reaction time varies depending on the scale of the reaction and the reaction temperature, but is generally between a few minutes and 24 hours.

Process Step [V13] from Scheme C:

One way of converting the N-oxides of the general formula (Ic) into the corresponding 2-halopyridines (Id, Hal²=Cl, Br) is provided by Process step [V13]. Suitable for use as halogenating agents are sulphuryl chloride, phosphoryl chloride, phosphoryl bromide or a mixture of phosphoryl chloride and phosphorus pentachloride, if appropriate in the presence of a base (for example triethylamine). Suitable for use as solvents for Process step [V13] are the halogenating agents themselves or also, for example, halogenated hydrocarbons (for example 1,2-dichloroethane) or aromatic hydrocarbons (for example toluene).

The halogenation for carrying out the Process step V13 according to the invention from Scheme C is carried out in a temperature range of from 25° to 150° C. The reaction time for carrying out the Process step V13 according to the invention from Scheme C varies depending on the scale of the reaction and the reaction temperature, but is generally between a few minutes and 24 hours.

Process Step [V14] from Scheme C:

One way of preparing compounds of the general formula (Ie) is described by Process step [V14]. To this end, the halogen atoms of (Id) are substituted by corresponding primary or secondary amines $HN(R^{6a})_2$, if appropriate in the presence of a base and, if appropriate, in the presence of a solvent.

Suitable solvents for carrying out the Process step V14 according to the invention from Scheme C may be the amines themselves or all customary solvents which are inert under the reaction conditions, such as cyclic and acyclic ethers (dimethoxymethane, tetrahydrofuran, dioxane), aromatic hydrocarbons (for example toluene), nitriles (for example acetonitrile, propionitrile) and amides (for example dimethylformamide, dimethylacetamide, N-methylpyrrolidone), or the reaction can be carried out in mixtures of two or more of these solvents. The preferred solvents are dimethylformamide and acetonitrile.

Suitable bases for carrying out the Process step V14 according to the invention from Scheme C are alkali metal hydroxides, alkali metal hydrides, alkali metal carbonates, alkali metal acetates, alkali metal alkoxides, and also tertiary amines. Preferred bases are sodium hydride, sodium carbonate, potassium carbonate or caesium carbonate.

The reaction temperature for carrying out the Process step V14 according to the invention from Scheme C is between 0° C. and 180° C., preferably between room temperature and 100° C. The reaction can be carried out under atmospheric pressure or under superatmospheric pressure. The reaction time is, depending on the scale of the reaction, between 5 min and 24 h, preferably between 30 min and 6 h.

Process Step [V15] from Scheme C:

One way of preparing compounds of the general formula (If) is described by Process step [V15]. Suitable acid-labile amines (for example $Z^1$=NHBn (cf. WO2008/132434) or NHtBu (cf. *Tetrahedron Lett.* 2005, 46, 3883-3887)) can be cleavaed in acidic media to give (2-aminopyridin-4-yl)thiazoles (If). Acids suitable for this purpose are mineral acids (for example $H_2SO_4$, HCl,) Lewis acids (for example $BBr_3$, $AlCl_3$) or organic acids (for example $F_3COOH$, $CF_3SO_3H$). Suitable for use as solvents are the acids themselves or all customary solvents which are inert under the reaction conditions, such as halogenated hydrocarbons (for example dichloromethane) or aromatic hydrocarbons (for example toluene). The reaction temperature is between 0° C. and 100° C. The reaction time is, depending on the scale of the reaction, between 5 min and 24 h, preferably between 30 min and 12 h.

Process Steps [V16] and [V17] from Scheme C:

Via Process step [V16] and [V17], starting with the amines (If) and (Ie for $Z^1$=primary amine) and using carbonyl chlorides or carboxylic anhydrides, it is possible to obtain the corresponding amides (Ig, where $Z^2$=R'CO), using chloroformates, it is possible to obtain the corresponding carbamates (Ig, where $Z^2$=R"COO) and using sulphonyl chlorides or sulphonic anhydrides, it is possible to obtain the corresponding sulphonamides (Ig, where $Z^2$=R'''SO$_2$). The compounds of the general formula $Z^2$-LG are either commercially available or can be prepared by customary methods of organic synthesis (R. C. Larock, *Comprehensive Organic Transformations,* 2nd edition, 1999, Wiley-VCH, page 1929 ff. and the literature cited therein).

Suitable for use as solvents for carrying out the Process steps V16 and V17 according to the invention from Scheme C are all customary solvents which are inert under the reaction conditions, such as, for example, cyclic and acyclic ethers (for example tetrahydrofuran, dioxane), aromatic hydrocarbons (for example toluene), halogenated hydrocarbons (for example dichloromethane), ketones (for example acetone), amides (for example dimethylformaide) and nitriles (for example acetonitrile), or the reaction can be carried out in mixtures of two or more of these solvents. The preferred solvents are tetrahydrofuran, dichloromethane and acetonitrile.

Suitable for use as acid scavengers for carrying out the Process steps V16 and V17 according to the invention from Scheme C are suitable bases. Preference is given to tertiary amines (for example triethylamine, ethyldiisopropylamine), alkali metal carbonates (for example sodium carbonate) or alkali metal hydroxides (sodium hydroxide).

The reaction for carrying out the Process steps V16 and V17 according to the invention from Scheme C is usually carried out at temperatures of from 0° C.-100° C. and preferably at room temperature, but it can also be carried out at up to the reflux temperature of the reaction mixture. The reaction time varies depending on the scale of the reaction and the reaction temperature, but is generally between a few minutes and 48 hours.

Alternatively, carboxamides and sulphonamides of the general formula (Ig where $Z^2$=R'CO, R"SO$_2$) can also be synthesized from the corresponding acids $Z^2$—OH in the presence of a coupling agent, analogously to the procedures described in the literature (for example *Tetrahedron* 2005, 61, 10827-10852, and the references cited therein).

Suitable coupling agents for carrying out the Process steps V16 and V17 according to the invention from Scheme C are, for example, carbodiimides (for example N-(3-dimethylaminopropyl)-N'-ethyl-carbodiimide, if appropriate with 4-dimethylaminopyridine or 1-hydroxybenzotriazole), phosphonium ions (for example bromotripyrrolidinophosphonium hexafluorophosphate) or uronium ions (for example O-(7-azabenzotriazol-1-yl)-N,N,N',N'-tetramethyluronium hexafluorophosphate).

If appropriate, a base for carrying out the Process steps V16 and V17 according to the invention from Scheme C, such as, for example, triethylamine or ethyldiisopropylamine can be used in the reaction. Suitable for use as solvents for carrying out the Process steps V16 and V17 according to the invention from Scheme C are all customary solvents which are inert under the reaction conditions, as described for the reaction with acid chlorides.

Process Step [V18] from Scheme C:

As described, for example, in DE102006037399 an amide radical can also be introduced directly under Pd catalysis, starting with the 2-halopyridines (Id).

Process Step [V19] from Scheme C:

One way of converting halopyridines of the general formula (Id) into the corresponding esters and amides is provided by Process step [V19]. Pd-catalyzed carbonylations of (Id) in the presence of alcohols afford the corresponding esters of the general formula (Ih, where $Z^3$=OR$^{6a}$, cf. *J. Med. Chem.* 2006, 49, 3563-3580), whereas in the presence of amines the corresponding amides (Ih, where $Z^3$=N(R$^{6a}$)$_2$ cf. *Chemistry Euro. J.* 2004, 10, 746-757) are formed. Suitable CO sources are carbon monoxide itself or metal carbonyls (for example Mo(CO)$_6$).

Suitable for use as solvents for carrying out the Process step V19 according to the invention from Scheme C are the alcohols or the amines themselves, and in addition all customary solvents which are inert under the reaction conditions, such as cyclic and acyclic ethers (for example dioxane), aromatic hydrocarbons (for example toluene), sulphoxides (for example DMSO) and amides (for example dimethylformamide, dimethylacetamide, N-methylpyrrolidone), or the reaction can be carried out in mixtures of two or more of these solvents. The preferred solvents are the alcohols or the amines themselves, and also dimethylformamide.

Suitable bases for carrying out the Process step V19 according to the invention from Scheme C are alkali metal carbonates (for example potassium carbonate), cyclic amidines (for example DBU) and also tertiary amines (for example triethylamine).

Preferred for carrying out the Process step V19 according to the invention from Scheme C are palladium catalysts in which the palladium is present in oxidation state (0) or (II), such as, for example, tetrakis(triphenylphosphine)palladium, bis(triphenylphosphine)palladium dichloride, bis(diphenylphosphino)ferrocenepalladium dichloride and also palladium(II) acetate. The catalyst may contain phosphorus-containing ligands, or phosphorus-containing ligands may be added separately to the reaction mixture. Suitable phosphorus-containing ligands are, preferably, tri-n-alkylphosphanes, triarylphosphanes, dialkylarylphosphanes, alkyldiarylphosphanes, where the three substituents at phosphorus may be identical or different and where one or more substituents may link the phosphorus groups of a plurality of phosphanes, where a metal atom may also be part of this linkage. Particular preference is given to phosphanes such as triphenylphosphane and 1,4-bis(diphenylphosphino)propane and 1,1'-bis(diphenylphosphino)ferrocenes.

The reaction for carrying out the Process step V19 according to the invention from Scheme C is carried out in a temperature range of from 25° to 150° C., particularly preferably at from 80° to 120° C. The reaction can be carried out under atmospheric pressure or under superatmospheric pressure. The reaction time varies depending on the scale of the reaction and the reaction temperature, but is generally between a few minutes and 20 hours.

Process Step [V20] from Scheme C:

One way of preparing compounds of the general formula (Ii) is described by Process step [V20]. To this end, N-oxides of the general formula (Ic) are reacted with suitable cyanide sources (for example TMS—CN, NaCN), as described in an exemplary manner in WO2007/093542, if appropriate in the presence of an activator (for example dimethylcarbaminic chloride, benzoyl chloride, dimethyl sulphate) in an inert solvent such as, for example, dichloromethane, acetonitrile or dimethylformamide in a temperature range between 0° C. and the boiling point of the solvent, preferably between 0 to 40° C.

Process Step [V21] from Scheme C:

One way of preparing compounds of the general formula (Ii) is described by Process step [V21]. To this end, a catalytic hydrogenation of the cyano function to the amino function allows acylation with $Z^2$-LG analogously to Process step [V16], giving compounds of the general formula (Ij). Suitable for use as hydrogenation catalysts are palladium (for example Pd/C) or nickel (for example Raney-Ni).

Suitable solvents for carrying out the Process step V21 according to the invention from Scheme C are alcohols (for example methanol, ethanol) or carboxylic acids (for example acetic acid). The reaction can be carried out under atmospheric pressure or under superatmospheric pressure. Alternatively, the reduction of the cyano function also succeeds with metal hydrides (for example $LiAlH_4$ in inert solvents such as tetrahydrofuran) at temperatures between 0° and 40° C.

Novel and likewise part of the invention are compounds of the general formula (Ic)

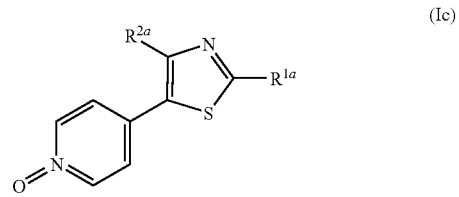

in which the symbols have the following meaning:
$R^{1a}$ and $R^{2a}$ have the general, preferred, particularly preferred and very particularly preferred meanings given above.

Novel and likewise part of the invention are compounds of the general formula (XI)

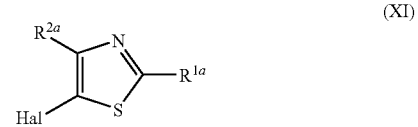

in which the symbols have the following meaning:
$R^{1a}$ has the general, preferred, particularly preferred and very particularly preferred meanings given above,
and
$R^{2a}$ represents phenyl, 2-fluorophenyl, 3-fluorophenyl, 4-fluorophenyl, 2,5-difluorophenyl, 2,4-difluorophenyl, 2,6-difluorophenyl, 2,4,6-trifluorophenyl, 3-trifluoromethylphenyl, 4-trifluoromethylphenyl, 4-methylphenyl, 3,4-dimethylphenyl, 4-cyanophenyl, 3-cyanophenyl, 4-chlorophenyl, 3-methyl-4-fluorophenyl, 3-cyano-4-fluorophenyl or
represents a thiophene radical which is optionally mono- or polysubstituted by identical or different radicals from the group consisting of halogen, cyano, $C_1$-$C_4$-alkyl, $C_1$-$C_4$-alkoxy, $C_1$-$C_4$-haloalkyl; Hal represents chlorine, bromine, iodine, preferably bromine, with the proviso that, if
$R^{2a}$ represents phenyl, 4-chlorophenyl or 4-cyanophenyl,
$R^{1a}$ does not represent methyl or bromomethyl.

The present invention furthermore relates to a crop protection composition for controlling unwanted fungi and for reducing mycotoxins in plants and parts of plants, comprising at least one 5-pyridin-4-yl-1,3-thiazole of the formula (I) and of the formula (Ia). Preferably, these are fungicidal and mycotoxin-reducing compositions comprising auxiliaries, solvents, carriers, surfactants or extenders suitable for use in agriculture.

Moreover, the invention relates to a method for controlling unwanted microorganisms, characterized in that in accordance with the invention 5-pyridin-4-yl-1,3-thiazoles of the formula (I) and also of the formula (Ia) are applied to the phytopathogenic and mycotoxin-producing fungi and/or their habitat.

According to the invention, carrier is to be understood as meaning a natural or synthetic, organic or inorganic substance which is mixed or combined with the active compounds for better applicability, in particular for application to plants or plant parts or seeds. The carrier, which may be solid or liquid, is generally inert and should be suitable for use in agriculture.

Suitable solid or liquid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral and vegetable oils and derivatives of these. Mixtures of such carriers may also be used. Suitable solid carriers for granules are: for example crushed and fractionated natural minerals, such as calcite, marble, pumice, sepiolite, dolomite, and also synthetic granules of inorganic and organic meals and also granules of organic material, such as sawdust, coconut shells, maize cobs and tobacco stalks.

Suitable liquefied gaseous extenders or carriers are liquids which are gaseous at ambient temperature and under atmospheric pressure, for example aerosol propellants, such as halocarbons, and also butane, propane, nitrogen and carbon dioxide.

Tackifiers, such as carboxymethylcellulose and natural and synthetic polymers in the form of powders, granules or lattices, such as gum arabic, polyvinyl alcohol, polyvinyl acetate, or else natural phospholipids, such as cephalins and lecithins and synthetic phospholipids can be used in the formulations. Other possible additives are mineral and vegetable oils.

If the extender used is water, it is also possible, for example, to use organic solvents as auxiliary solvents. Suitable liquid solvents are essentially: aromatic compounds, such as xylene, toluene or alkylnaphthalenes, chlorinated aromatic compounds or chlorinated aliphatic hydrocarbons, such as chlorobenzenes, chloroethylenes or dichloromethane, aliphatic hydrocarbons, such as cyclohexane or paraffins, for example mineral oil fractions, mineral and vegetable oils, alcohols, such as butanol or glycol, and also ethers and esters thereof, ketones, such as acetone, methyl ethyl ketone, methyl isobutyl ketone or cyclohexanone, strongly polar solvents, such as dimethylformamide and dimethyl sulphoxide, and also water.

The compositions according to the invention may comprise additional further components, such as, for example, surfactants. Suitable surfactants are emulsifiers and/or foam formers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example, alkylaryl polyglycol ethers, alkylsulphonates, alkyl sulphates, arylsulphonates, protein hydrolysates, ligno-sulphite waste liquors and methylcellulose. The presence of a surfactant is required if one of the active compounds and/or one of the inert carriers is insoluble in water and when the application takes place in water. The proportion of surfactants is between 5 and 40 percent by weight of the composition according to the invention.

It is possible to use colorants such as inorganic pigments, for example iron oxide, titanium oxide, Prussian blue, and organic dyes, such as alizarin dyes, azo dyes and metal phthalocyanine dyes, and trace nutrients, such as salts of iron, manganese, boron, copper, cobalt, molybdenum and zinc.

If appropriate, other additional components may also be present, for example protective colloids, binders, adhesives, thickeners, thixotropic substances, penetrants, stabilizers, sequestering agents, complex formers. In general, the active compounds can be combined with any solid or liquid additive customarily used for formulation purposes.

In general, the formulations contain between 0.05 and 99% by weight, 0.01 and 98% by weight, preferably between 0.1 and 95% by weight, especially preferably between 0.5 and 90% by weight of active compound, very especially preferably between 10 and 70 percent by weight.

The active compounds or compositions according to the invention can be used as such or, depending on their respective physical and/or chemical properties, in the form of their formulations or the use forms prepared therefrom, such as aerosols, capsule suspensions, cold-fogging concentrates, warmfogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV cold-fogging and warm-fogging formulations.

The formulations mentioned can be prepared in a manner known per se, for example by mixing the active compounds with at least one customary extender, solvent or diluent, emulsifier, dispersant and/or binder or fixing agent, wetting agent, water repellant, if appropriate siccatives and UV stabilizers and, if appropriate, dyes and pigments, defoamers, preservatives, secondary thickeners, adhesives, gibberellins and also further processing auxiliaries.

The compositions according to the invention do not only comprise ready-to-use formulations which can be applied with a suitable apparatus to the plant or the seed, but also commercial concentrates which have to be diluted with water prior to use.

The active compounds according to the invention, per se or in their (commercially available) formulations and in the use forms prepared from these formulations, may be present in a mixture with other (known) active compounds such as insecticides, attractants, sterilants, bactericides, acaricides, nematicides, fungicides, growth regulators, herbicides, fertilizers, safeners or semiochemicals.

The treatment according to the invention of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, drenching, drip irrigating and, in the case of propagation material, in particular in the case of seeds, furthermore by dry seed treatment, by wet seed treatment, by slurry treatment, by incrusting, by coating with one or more coats, etc. It is furthermore possible to apply the active compounds by the ultra-low-volume method, or to inject the active compound preparation, or the active compound itself, into the soil.

The invention furthermore comprises a method for the treatment of seed.

The invention furthermore relates to seed which has been treated in accordance with one of the methods described in the previous paragraph. The seeds according to the invention are used in methods for the protection of seed from undesirable fungi. Here, a seed treated with at least one active compound according to the invention is used.

The active compounds or compositions according to the invention are also suitable for treating seed. A large part of the damage to crop plants caused by harmful organisms is triggered by the infection of the seed during storage or after sowing as well as during and after germination of the plant. This phase is particularly critical since the roots and shoots of the growing plant are particularly sensitive, and even just small damage may result in the death of the plant. Accordingly, there is great interest in protecting the seed and the germinating plant by using appropriate compositions.

The control of phytopathogenic fungi by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection compositions after sowing or after the emergence of the plants or which at least considerably reduce additional application. It is furthermore desirable to optimize the amount of active compound employed in such a way as to provide maximum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection compositions being employed.

Accordingly, the present invention also relates to a method for protecting seed and germinating plants against attack by phytopathogenic fungi by treating the seed with a composition according to the invention. The invention also relates to the use of the compositions according to the invention for treating seed for protecting the seed and the germinating plant against phytopathogenic fungi. Furthermore, the invention relates to seed treated with a composition according to the invention for protection against phytopathogenic fungi.

The control of phytopathogenic fungi which damage plants post-emergence is carried out primarily by treating the soil and the above-ground parts of plants with crop protection compositions. Owing to the concerns regarding a possible impact of the crop protection compositions on the environment and the health of humans and animals, there are efforts to reduce the amount of active compounds applied.

One of the advantages of the present invention is that, because of the particular systemic properties of the active compounds or compositions according to the invention, treatment of the seed with these active compounds or compositions not only protects the seed itself, but also the resulting plants after emergence, from phytopathogenic fungi. In this manner, the immediate treatment of the crop at the time of sowing or shortly thereafter can be dispensed with.

It is also considered to be advantageous that the active compounds or compositions according to the invention can be used in particular also for transgenic seed where the plant growing from this seed is capable of expressing a protein which acts against pests. By treating such seed with the active compounds or compositions according to the invention, even by the expression of the, for example, insecticidal protein, certain pests may be controlled. Surprisingly, a further synergistic effect may be observed here, which additionally increases the effectiveness of the protection against attack by pests.

The compositions according to the invention are suitable for protecting seed of any plant variety employed in agriculture, in the greenhouse, in forests or in horticulture and viticulture. In particular, this takes the form of seed of cereals (such as wheat, barley, rye, triticale, sorghum/millet and oats), maize, cotton, soya beans, rice, potatoes, sunflower, bean, coffee, beet (for example sugar beet and fodder beet), peanut, oilseed rape, poppy, olive, coconut, cacao, sugar cane, tobacco, vegetables (such as tomato, cucumbers, onions and lettuce), turf and ornamentals (see also hereinbelow). Of particular importance is the treatment of the seed of cereals (such as wheat, barley, rye, triticale and oats), maize and rice.

As also described hereinbelow, the treatment of transgenic seed with the active compounds or compositions according to the invention is of particular importance. This refers to the seed of plants containing at least one heterologous gene which allows the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. Preferably, this heterologous gene is from *Bacillus* sp., the gene product having activity against the European corn borer and/or the Western corn rootworm. Particularly preferably, the heterologous gene originates from *Bacillus thuringiensis*.

In the context of the present invention, the composition according to the invention is applied on its own or in a suitable formulation to the seed. Preferably, the seed is treated in a state in which it is sufficiently stable so that the treatment does not cause any damage. In general, treatment of the seed may take place at any point in time between harvesting and sowing. Usually, the seed used has been separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The compositions according to the invention can be applied directly, that is to say without comprising further components and without having been diluted. In general, it is preferable to apply the compositions to the seed in the form of a suitable formulation. Suitable formulations and methods for the treatment of seed are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compounds which can be used according to the invention can be converted into the customary seed-dressing product formulations such as solutions, emulsions, suspensions, powders, foams, slurries and other coating compositions for seed, and ULV formulations.

These formulations are prepared in the known manner by mixing the active compounds with customary additives such as, for example, customary extenders and also solvents or diluents, colorants, wetters, dispersants, emulsifiers, antifoams, preservatives, secondary thickeners, adhesives, gibberellins, and also water.

Colorants which may be present in the seed-dressing product formulations which can be used according to the invention are all colorants which are customary for such purposes. Both pigments, which are sparingly soluble in water, and dyes, which are soluble in water, may be used. Examples of colorants which may be mentioned are those known by the names Rhodamin B, C.I. Pigment Red 112 and C.I. Solvent Red 1.

Wetters which may be present in the seed-dressing product formulations which can be used according to the invention are all substances which are conventionally used for the formulation of agrochemical active compounds and for promoting wetting. Alkylnaphthalenesulphonates, such as diisopropyl- or diisobutylnaphthalenesulphonates, can preferably be used.

Suitable dispersants and/or emulsifiers which may be present in the seed-dressing product formulations which can be used in accordance with the invention are all non-ionic, anionic and cationic dispersants which are conventionally used for the formulation of agrochemical active compounds. Non-ionic or anionic dispersants or mixtures of non-ionic or anionic dispersants can preferably be used. Suitable non-ionic dispersants which may be mentioned are, in particular, ethylene oxide/propylene oxide block polymers, alkylphenol polyglycol ethers and tristryrylphenol polyglycol ethers, and their phosphated or sulphated derivatives. Suitable anionic dispersants are, in particular, lignosulphonates, polyacrylic acid salts and arylsulphonate/formaldehyde condensates.

Antifoams which may be present in the seed-dressing product formulations which can be used according to the invention are all foam-suppressing substances conventionally used for the formulation of agrochemical active compounds. Silicone antifoams and magnesium stearate can preferably be used.

Preservatives which may be present in the seed-dressing product formulations which can be used according to the invention are all substances which can be employed in agrochemical compositions for such purposes. Examples which may be mentioned are dichlorophene and benzyl alcohol hemiformal.

Secondary thickeners which may be present in the seed-dressing product formulations which can be used according to the invention are all substances which can be employed in agrochemical compositions for such purposes. Cellulose derivatives, acrylic acid derivatives, xanthan, modified clays and highly disperse silica are preferably suitable.

Adhesives which may be present in the seed-dressing product formulations which can be used according to the invention are all customary binders which can be employed in seed-dressing products. Polyvinylpyrrolidone, polyvinyl acetate, polyvinyl alcohol and tylose may be mentioned by preference.

Gibberellins which may be present in the seed-dressing product formulations which can be used according to the invention are preferably the gibberellins A1, A3 (=gibberellic acid), A4 and A7, with gibberellic acid being particularly preferably used. The gibberellins are known (cf. R. Wegler "Chemie der Pflanzenschutz- and Schädlingsbekämpfungsmittel" [Chemistry of Plant Protectants and Pesticides], Vol. 2, Springer Verlag, 1970, pp. 401-412).

The seed-dressing product formulations which can be used in accordance with the invention can be employed either directly or after previous dilution with water for the treatment of a wide range of seeds, including the seed of transgenic plants. In this context, additional synergistic effects may also occur as a consequence of the interaction with the substances formed by expression.

Suitable apparatuses which can be employed for treating seed with the seed-dressing product formulations which can be used in accordance with the invention, or with the preparations prepared therefrom by addition of water, are all mixing apparatuses which can usually be employed for dressing seed. Specifically, a seed-dressing procedure is followed in which the seed is placed in a mixer, the amount of seed-dressing product formulation desired in each case is added, either as such or after previously diluting it with water, and the contents of the mixer are mixed until the formulation has been distributed uniformly on the seed. If appropriate, this is followed by a drying process.

The active compounds or compositions according to the invention have a potent fungicidal and mycotoxin-reducing action and can be employed for controlling unwanted and mycotoxin-producing fungi in crop protection and in the protection of materials.

The 5-pyridin-4-yl-1,3-thiazoles according to the invention can be used in crop protection for controlling Plasmodiophoromycetes, Oomycetes, Chytridiomycetes, Zygomycetes, Ascomycetes, Basidiomycetes and Deuteromycetes.

The fungicidal compositions according to the invention can be employed curatively or protectively for controlling phytopathogenic fungi and mycotoxin-producing fungi. The invention therefore also relates to curative and protective methods of controlling phytopathogenic fungi and of reducing mycotoxins in plants and plant parts by using the active compounds or compositions according to the invention, which are applied to the seed, the plant or plant parts, the fruits or the soil in which the plants grow.

In a preferred embodiment, the plant or the plant material treated with the compounds of the formula (I) or (Ia) according to the invention has at least 10%, preferably at least 20%, particularly preferably at least 40% less mycotoxin than an untreated plant or untreated plant material.

The compositions according to the invention for controlling phytopathogenic fungi and mycotoxin-producing fungi in plant protection comprise an effective, but nonphytotoxic amount of the active compounds according to the invention. "Effective, but nonphytotoxic amount" means such an amount of the composition according to the invention which suffices for sufficiently controlling or fully eradicating the fungal disease of the plant while simultaneously not entailing substantial phytotoxicity symptoms. In general, this application rate can vary within a substantial range. It depends on a plurality of factors, for example on the fungus to be controlled, the plant, the climatic conditions and the constituents of the compositions according to the invention.

The good plant tolerance of the active compounds at the concentrations required for controlling plant diseases permits the treatment of aerial plant parts, of vegetative propagation material and of seed, and of the soil.

All plants and plant parts can be treated in accordance with the invention. In the present context, plants are understood as meaning all plants and plant populations, such as desired and undesired wild plants or crop plants (including naturally occurring crop plants). Crop plants can be plants which can be obtained by traditional breeding and optimization methods or by biotechnological and recombinant methods, or combinations of these methods, including the transgenic plants and including the plant varieties capable or not of being protected by Plant Breeders' Rights. Plant parts are understood as meaning all aerial and subterranean parts and organs of the plants, such as shoot, leaf, flower and root, examples which may be mentioned being leaves, needles, stalks, stems, flowers, fruiting bodies, fruits and seeds, and also roots, tubers and rhizomes. The plant parts also include crop material and vegetative and generative propagation material, for example cuttings, tubers, rhizomes, slips and seeds.

The active compounds according to the invention are suitable for the protection of plants and plant organs, for increasing the yields, for improving the quality of the harvested crop, while being well tolerated by plants, having favourable toxicity to warm-blooded species and being environmentally friendly. They can preferably be employed as crop protection compositions. They are active against normally sensitive and resistant species and against all or individual developmental stages.

Plants which can be treated in accordance with the invention and which may be mentioned are the following: cotton, flax, grapevine, fruit, vegetables, such as Rosaceae sp. (for example pome fruits such as apples and pears, but also stone fruits such as apricots, cherries, almonds and peaches, and soft fruits such as strawberries), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for example banana plants and banana plantations), Rubiaceae sp. (for example coffee), Theaceae sp., Sterculiceae sp., Rutaceae sp. (for example lemons, oranges and grapefruit); Solanaceae sp. (for example tomatoes), Liliaceae sp., Asteraceae sp. (for example lettuce), Umbelliferae sp., Cruciferae sp., Chenopodiaceae sp., Cucurbitaceae sp. (for example cucumbers), Alliaceae sp. (for example leeks, onions), Papilionaceae sp. (for example peas); major crop plants such as Gramineae sp. (for example maize, turf, cereals such as wheat, rye, rice, barley, oats, sorghum, millet and triticale), Asteraceae sp. (for example sunflower), Brassicaceae sp. (for example white cabbage, red cabbage, broccoli, cauliflower, Brussels sprouts, pak Choi, kohlrabi, small radishes, and also oilseed rape, mustard, horseradish and cress), Fabacae sp. (for example beans, peanuts), Papilionaceae sp. (for example soya beans), Solanaceae sp. (for example potatoes), Chenopodiaceae sp. (for example sugar beet, fodder beet, Swiss chard, beetroot); useful plants and ornamental plants in gardens and forests; and in each case genetically modified types of these plants.

As has already been mentioned above, all plants and their parts may be treated in accordance with the invention. In a preferred embodiment, plant species and plant varieties, and their parts, which grow wild or which are obtained by traditional biological breeding methods such as hybridization or protoplast fusion are treated. In a further preferred embodiment, transgenic plants and plant varieties which have been obtained by recombinant methods, if appropriate in combination with traditional methods (genetically modified organisms), and their parts are treated. The term "parts" or "parts of plants" or "plant parts" has been explained hereinabove. Plants of the plant varieties which are in each case commercially available or in use are especially preferably treated in accordance with the invention. Plant varieties are understood as meaning plants with novel traits which have been bred both by traditional breeding, by mutagenesis or by recombinant DNA techniques. They may take the form of varieties, races, biotypes and genotypes.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNA interference—RNAi technology). A heterologous gene that is located in the genome is also called a transgene. A transgene that is defined by its particular location in the plant genome is called a transformation or transgenic event.

Depending on the plant species or plant varieties, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are suitable for mobilizing the defense system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are to be understood as meaning, in the present context, also those substances or combinations of substances which are capable of stimulating the defense system of plants in such a way that, when subsequently inoculated with unwanted phytopathogenic fungi, the treated plants display a substantial degree of resistance to these unwanted phytopathogenic fungi. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant varieties which are preferably to be treated according to the invention include all plants which have genetic material which imparts particularly advantageous, useful traits to these plants (whether obtained by breeding and/or biotechnological means).

Plants and plant varieties which are also preferably to be treated according to the invention are resistant against one or more biotic stresses, i.e. said plants have a better defence against animal and microbial pests, such as against nematodes, insects, mites, phytopathogenic fungi, bacteria, viruses and/or viroids.

Plants and plant varieties which may also be treated according to the invention are those plants which are resistant to one or more abiotic stresses. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant varieties which may also be treated according to the invention are those plants characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis, or hybrid vigour, which results in generally higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in the hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male sterile plants can also be obtained by plant biotechnology methods such as genetic engineering. A particularly useful means of obtaining male sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an Eleusine EPSPS. It can also be a mutated EPSPS. Glyphosatetolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally occurring mutations of the abovementioned genes.

Other herbicide-resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species). Plants expressing an exogenous phosphinothricin acetyltransferase are described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD inhibitors can be transformed with a gene encoding a naturally occurring resistant HPPD enzyme, or a gene encoding a mutated HPPD enzyme. Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding an enzyme of prephenate dehydrogenase in addition to a gene encoding an HPPD-tolerant enzyme.

Further herbicide-resistant plants are plants that are made tolerant to acetolactate synthase (ALS) inhibitors. Known ALS inhibitors include, for example, sulphonylurea, imidazolinone, triazolopyrimidines, pyrimidinyloxy(thio)benzoates, and/or sulphonylaminocarbonyltriazolinone herbicides. Different mutations in the ALS enzyme (also known as acetohydroxyacid synthase, AHAS) are known to confer tolerance to different herbicides and groups of herbicides. The production of sulphonylurea-tolerant plants and imidazolinone-tolerant plants has been described in the international publication WO 1996/033270. Further sulphonylurea- and imidazolinone-tolerant plants have also been described, for example in WO 2007/024782.

Other plants tolerant to imidazolinone and/or sulphonylurea can be obtained by induced mutagenesis, selection in cell cultures in the presence of the herbicide or mutation breeding.

Plants or plant varieties (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

The term "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed online at:
http://www.lifesci.sussex.ac.uk/Home/Neil_Crickmore/ Bt/, or insecticidal portions thereof, e.g. proteins of the Cry protein classes Cry1Ab, Cry1Ac, Cry1F, Cry2Ab, Cry3Ae, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins; or 3) a hybrid insecticidal protein comprising parts of two different insecticidal crystal proteins from *Bacillus thuringiensis*, such as a hybrid of the proteins of 1) above or a hybrid of the proteins of 2) above, e.g. the Cry1A.105 protein produced by corn event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced into the encoding DNA during cloning or transformation, such as the Cry3Bb1 protein in corn events MON863 or MON88017, or the Cry3A protein in corn event MIR 604;

5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/Home/Neil_Cricicmore/Bt/vip.html, e.g. proteins from the VIP3Aa protein class;

6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins; or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced into the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant varieties (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of the poly(ADP-ribose) polymerase (PARP) gene in the plant cells or plants.

b. plants which contain a stress tolerance-enhancing transgene capable of reducing the expression and/or the activity of the PARG-encoding genes of the plants or plant cells.

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant varieties (obtained by plant biotechnology methods such as genetic engineering) which may also be treated according to the invention show altered quantity, quality and/or storage stability of the crop product and/or altered properties of specific ingredients of the crop product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesized starch in wild type plant cells or plants, so that this modified starch is better suited for special applications.

2) transgenic plants which synthesize non-starch carbohydrate polymers or which synthesize non-starch carbohydrate polymers with altered properties in comparison to wild type plants without genetic modification. Examples are plants which produce polyfructose, especially of the inulin and levan type, plants which produce alpha-1,4-glucans, plants which produce alpha-1,6 branched alpha-1,4-glucans, and plants producing alternan.

3) transgenic plants which produce hyaluronan.

Plants or plant varieties (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:

a) plants, such as cotton plants which contain an altered form of cellulose synthase genes, b) plants, such as cotton plants which contain an altered form of rsw2 or rsw3 homologous nucleic acids;

c) plants, such as cotton plants, with an increased expression of sucrose phosphate synthase;

d) plants, such as cotton plants, with an increased expression of sucrose synthase;

e) plants, such as cotton plants, wherein the timing of the plasmodesmatal gating at the basis of the fibre cell is altered, e.g. through downregulation of fibre-selective β-1,3-glucanase;

f) plants, such as cotton plants, which have fibres with altered reactivity, e.g. through the expression of the N-acetylglucosaminetransferase gene including nodC and chitin synthase genes.

Plants or plant varieties (obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:

a) plants, such as oilseed rape plants, which produce oil having a high oleic acid content;

b) plants, such as oilseed rape plants, which produce oil having a low linolenic acid content;

c) plants, such as oilseed rape plants, which produce oil having a low level of saturated fatty acids.

Particularly useful transgenic plants which may be treated according to the invention are plants which comprise one or more genes which encode one or more toxins and are the following which are sold under the trade names YIELD GARD® (for example maize, cotton, soya beans), Knock-Out® (for example maize), BiteGard® (for example maize), BT-Xtra® (for example maize), StarLink® (for example maize), Bollgarde® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, that are listed for example in the databases for various national or regional regulatory agencies (see for example http://gmoinfo.jrc.it/gmp_browse.aspx and http://www.agbios.com/dbase.php).

The active compounds or compositions according to the invention may furthermore be employed in the protection of materials for protecting industrial materials against attack and destruction by undesired microorganisms such as, for example, fungi.

In the present context, industrial materials are understood as meaning nonliving materials which have been prepared for use in industry. Industrial materials which are intended to be protected by active compounds according to the invention from fungal change or destruction can be, for example, glues, sizes, paper, wall card and board, textiles, carpets, leather, wood, paints and plastic articles, cooling lubricants and other materials which are capable of being attacked or decomposed by microorganisms. Other materials to be protected and which can be adversely affected by the multiplication of microorganisms which may be mentioned within the scope are parts of production plants and buildings, for example cooling water circuits, cooling and heating systems and aeration and air-conditioning units. Industrial materials which may be mentioned by preference within the scope of the present invention are glues, sizes, paper and boards, leather, wood, paints, cooling lubricants and heat-transfer fluids, especially preferably wood. The active compounds or compositions according to the invention can prevent disadvantageous effects such as wilting, decay, discolouration, decolouration or mould development. Moreover, the compounds according to the invention can be employed for protecting objects against being covered with growth, in particular ships' hulls, sieves, nets, buildings, jetties and signal units, which come into contact with seawater or brackish water.

The method according to the invention for controlling unwanted fungi can also be employed for protecting storage goods. Here, storage goods are to be understood as meaning natural substances of vegetable or animal origin or processed products thereof of natural origin, for which long-term protection is desired. Storage goods of vegetable origin, such as, for example, plants or plant parts, such as stems, leaves, tubers, seeds, fruits, grains, can be protected in the freshly harvested state or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, pelts, leather, furs and hairs. The active compounds according to the invention can prevent disadvantageous effects, such as rotting, decay, discolouration, decolouration or the development of mould.

Some pathogens of fungal diseases which can be treated according to the invention may be mentioned, by way of example, but not by way of limitation:

Diseases caused by powdery mildew pathogens, such as, for example, *Blumeria* species, such as, for example, *Blumeria graminis*; *Podosphaera* species, such as, for example, *Podosphaera leucotricha*; *Sphaerotheca* species, such as, for example, *Sphaerotheca fuliginea*; *Uncinula* species, such as, for example, *Uncinula necator*;

Diseases caused by rust disease pathogens, such as, for example, *Gymnosporangium* species, such as, for example, *Gymnosporangium sabinae*; *Hemileia* species, such as, for example, *Hemileia vastatrix*; *Phakopsora* species, such as, for example, *Phakopsora pachyrhizi* and *Phakopsora meibomiae*; *Puccinia* species, such as, for example, *Puccinia recondita* or *Puccinia triticina*; *Uromyces* species, such as, for example, *Uromyces appendiculatus*;

Diseases caused by pathogens from the group of the Oomycetes, such as, for example, *Bremia* species, such as, for example, *Bremia lactucae*; *Peronospora* species, such as, for example, *Peronospora pisi* or *P. brassicae*; *Phytophthora* species, such as, for example, *Phytophthora infestans*; *Plasmopara* species, such as, for example, *Plasmopara viticola*; *Pseudoperonospora* species, such as, for example, *Pseudoperonospora humuli* or *Pseudoperonospora cubensis*; *Pythium* species, such as, for example, *Pythium ultimum*;

Leaf blotch diseases and leaf wilt diseases caused, for example, by *Alternaria* species, such as, for example, *Alternaria solani*; *Cercospora* species, such as, for example, *Cercospora beticola*; *Cladiosporum* species, such as, for example, *Cladiosporium cucumerinum*; *Cochliobolus* species, such as, for example, *Cochliobolus sativus* (conidia form: *Drechslera*, Syn: *Helminthosporium*); *Colletotrichum* species, such as, for example, *Colletotrichum lindemuthanium*; *Cycloconium* species, such as, for example, *Cycloconium oleaginum*; *Diaporthe* species, such as, for example, *Diaporthe citri*; *Elsinoe* species, such as, for example, *Elsinoe fawcettii*; *Gloeosporium* species, such as, for example, *Gloeosporium laeticolor*; *Glomerella* species, such as, for example, *Glomerella cingulata*; *Guignardia* species, such as, for example, *Guignardia bidwelli*; *Leptosphaeria* species, such as, for example, *Leptosphaeria maculans*; *Magnaporthe* species, such as, for example, *Magnaporthe grisea*; *Microdochium* species, such as, for example, *Microdochium nivale*; *Mycosphaerella* species, such as, for example, *Mycosphaerella graminicola* and *M. fijiensis*; *Phaeosphaeria* species, such as, for example, *Phaeosphaeria nodorum*; *Pyrenophora* species, such as, for example, *Pyrenophora teres*; *Ramularia* species, such as, for example, *Ramularia collo-cygni*; *Rhynchosporium* species, such as, for example, *Rhynchosporium secalis*; *Septoria* species, such as, for example, *Septoria apii*; *Typhula* species, such as, for example, *Typhula incarnata*; *Venturia* species, such as, for example, *Venturia inaequalis*;

Root and stem diseases caused, for example, by *Corticium* species, such as, for example, *Corticium graminearum*; *Fusarium* species, such as, for example, *Fusarium* oxysporum; *Gaeumannomyces* species, such as, for example, *Gaeumannomyces graminis*; *Rhizoctonia* species, such as, for example, *Rhizoctonia solani*; *Tapesia* species, such as, for example, *Tapesia acuformis*; *Thielaviopsis* species, such as, for example, *Thielaviopsis basicola*;

Ear and panicle diseases (including maize cobs) caused, for example, by *Alternaria* species, such as, for example, *Alternaria* spp.; *Aspergillus* species, such as, for example, *Aspergillus flavus*; *Cladosporium* species, such as, for example, *Cladosporium cladosporioides*; *Claviceps* species, such as, for example, *Claviceps purpurea*; *Fusarium* species, such as, for example, *Fusarium culmorum*; *Gibberella* species, such as, for example, *Gibberella zeae*; *Monographella* species, such as, for example, *Monographella nivalis*; *Septoria* species, such as, for example, *Septoria nodorum*;

Diseases caused by smut fungi, such as, for example, *Sphacelotheca* species, such as, for example, *Sphacelotheca reiliana*; *Tilletia* species, such as, for example, *Tilletia caries, T. controversa*; *Urocystis* species, such as, for example, *Urocystis occulta*; *Ustilago* species, such as, for example, *Ustilago nuda, U. nuda tritici*;

Fruit rot caused, for example, by *Aspergillus* species, such as, for example, *Aspergillus flavus*; *Botrytis* species, such as, for example, *Botrytis cinerea*; *Penicillium* species, such as, for example, *Penicillium expansum* and *P. purpurogenum*; *Sclerotinia* species, such as, for example, *Sclerotinia sclerotiorum*;

*Verticilium* species, such as, for example, *Verticilium alboatrum*;

Seed- and soil-borne rot and wilt diseases, and also diseases of seedlings, caused, for example, by *Fusarium* species, such as, for example, *Fusarium culmorum*; *Phytophthora* species, such as, for example, *Phytophthora cactorum*; *Pythium* species, such as, for example, *Pythium ultimum*; *Rhizoctonia* species, such as, for example, *Rhizoctonia solani*; *Sclerotium* species, such as, for example, *Sclerotium rolfsii*;

Cancerous diseases, galls and witches' broom caused, for example, by *Nectria* species, such as, for example, *Nectria galligena*;

Wilt diseases caused, for example, by *Monilinia* species, such as, for example, *Monilinia laxa*;

Deformations of leaves, flowers and fruits caused, for example, by *Taphrina* species, such as, for example, *Taphrina deformans*;

Degenerative diseases of woody plants caused, for example, by *Esca* species, such as, for example, *Phaemoniella clamydospora* and *Phaeoacremonium aleophilum* and *Fomitiporia mediterranea*;

Diseases of flowers and seeds caused, for example, by *Botrytis* species, such as, for example, *Botrytis cinerea*;

Diseases of plant tubers caused, for example, by *Rhizoctonia species*, such as, for example, *Rhizoctonia solani*; *Helminthosporium* species, such as, for example, *Helminthosporium solani*;

Diseases caused by bacteriopathogens, such as, for example, *Xanthomonas* species, such as, for example, *Xanthomonas campestris* pv. *oryzae*; *Pseudomonas* species, such as, for example, *Pseudomonas syringae* pv. *lachrymans*; *Erwinia* species, such as, for example, *Ervvinia amylovora*.

Preference is given to controlling the following diseases of soya beans:

Fungal diseases on leaves, stems, pods and seeds caused, for example, by *alternaria* leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmopspora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia Southern blight (*Sclerotinia rolfsii*), thielaviopsis root rot (*Thielaviopsis basicola*).

Organisms which can bring about degradation or modification of the industrial materials and which may be mentioned are fungi. The active compounds according to the invention are preferably active against fungi, in particular moulds, wood-discolouring and wood-destroying fungi (Basidiomycetes). Fungi of the following genera may be mentioned by way of example: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*.

When employing the active compounds according to the invention as fungicides and mycotoxin-reducing active compounds, the application rates may vary within a substantial range, depending on the type of application. The application rate of the active compounds according to the invention is
  when treating plant parts, for example leaves: from 0.1 to 10 000 g/ha, preferably from 10 to 1000 g/ha, particularly preferably from 50 to 300 g/ha (when the application is carried out by watering or dropwise, it may even be possible to reduce the application rate, in particular when inert substrates such as rock wool or perlite are used);
  when treating seed: from 2 to 200 g per 100 kg of seed, preferably from 3 to 150 g per 100 kg of seed, especially preferably from 2.5 to 25 g per 100 kg of seed, very especially preferably from 2.5 to 12.5 g per 100 kg of seed;
  when treating the soil: from 0.1 to 10 000 g/ha, preferably from 1 to 5000 g/ha.

These application rates are mentioned only by way of example and not by way of limitation in the sense of the invention.

The active compounds or compositions according to the invention can thus be employed for protecting plants for a certain period of time after treatment against attack by the pathogens mentioned. The period for which protection is provided extends generally for 1 to 28 days, preferably 1 to 14 days, particularly preferably 1 to 10 days, very particularly preferably 1 to 7 days after the treatment of the plants with the active compounds, or up to 200 days after the treatment of seed.

In addition, by the treatment according to the invention it is possible to reduce the mycotoxin content in the harvested material and the foodstuff and feedstuff prepared therefrom. Particular, but not exclusive, mention may be made here of the following mycotoxins: deoxynivalenol (DON), nivalenol, 15-Ac-DON, 3-Ac-DON, 4-acetylnivalenol (Fusarenon-X), 4,15-diacetylnivalenol, 4,7,15-acetynivalenol, T2- and HT2-toxin, isotrichodermol, 3-deacetylcalonectrin, 3,15-dideacetylcalonectrin, scirpentriol, neosolaniol, fumonisine, (for example FB1, FB2, FB3), zearalenon, moniliformin, fusarin, diaceotoxyscirpenol (DAS), beauvericin, enniatin, fusaroproliferin, fusarenol, ochratoxins, patulin, ergot alkaloids ochratoxins (for example ochratoxin A, B and C) and aflatoxins (for example aflatoxin B1, B2, G1 and G2, cyclopiazonic acid) produced, for example, by the following fungi: *Fusarium* spec., such as *Fusarium acuminatum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides,* inter alia, and also by *Aspergillus* spec. (for example *A. ochraceus, A. carbonarius, A. flavus*), *Penicillium* spec. (for example *P. viridicutum*), *Claviceps purpurea, Stachybotrys* spec. inter alia.

The abovementioned plants can be treated especially advantageously in accordance with the invention with the compounds of the general formula (I) the compositions according to the invention. The preferred ranges indicated above for the active compounds or compositions also apply to the treatment of these plants. The treatment of plants with the compounds or compositions mentioned specifically in the present text should be especially emphasized.

The preparation of the compounds of the general formula (Ia) according to the invention is illustrated by the examples below. However, the invention is not limited to these examples:

Synthesis Examples for Process A from Scheme A

Process Step [V1]: 1-(5-Chloro-2-thienyl)-2-(pyridin-4-yl)ethanone

At 0° C., 64.5 ml of a 1M solution of lithium bis(trimethylsilyl)amide in hexane are added dropwise to a solution of 3.00 g (32.3 mmol) of 4-methylpyridine and 6.77 g (35.5 mmol) of ethyl 5-chlorothiophene-2-carboxylate in 58 ml THF, and the reaction mixture is stirred at 5° C. for 3 h. The resulting precipitate was filtered off, acidified with 6M HCl, filtered again and dried. This gives 2.9 g (35%) of the desired product; $^1$H-NMR (DMSO-d6): δ=8.53 (d, 2H), 8.09 (d, 1H), 7.40 (d, 1H), 7.34 (d, 2H), 4.39 (s, 2H).

Process Step [V2]: 2-Bromo-1-(5-chloro-2-thienyl)-2-(pyridin-4-yl)ethanone

At room temperature, 26.9 g (167 mmol) of bromine are added dropwise to a solution of 40.0 g (167 mmol) of 1-(5-chloro-2-thienyl)-2-(pyridin-4-yl)ethanone in 200 ml of acetic acid, and the mixture is stirred for 90 min. The resulting precipitate is filtered off, washed with MTBE and dried. This gives 64.5 g (96%) of the desired product; log P (pH2.7): 2.18 with MS (ESI): 315.9 ([M+H]$^+$).

Process Step [V3]: 4-[2-Ethyl-4-(4-fluorophenyl)-1,3-thiazol-5-yl]pyridine (Ex. 41)

At room temperature, 1.31 g (14.7 mmol) propanethioamide are added to a solution of 5.00 g (13.3 mmol) of 2-bromo-1-(4-fluorophenyl)-2-(4-pyridyl)ethanone hydrobromide (described, for example, in *Chem. Pharm. Bull.* 2005, 53, 410-418) in 30 ml of DMF, and the mixture is stirred for 16 h. Subsequently, the reaction mixture is stirred into 100 ml of ice-water, 50 ml of a saturated aqueous Na—HCO$_3$ are added and the mixture is extracted with ethyl acetate (3×100 ml). The combined organic phases are washed with water (2×100 ml), dried over MgSO$_4$ and freed from the solvent under reduced pressure. The crude product is then purified by column chromatography on silica gel (cyclohexane/ethyl acetate). This gives 2.85 g (75%) of the desired product; $^1$H-NMR (DMSO-d6) δ: 8.53 (d, 2H), 7.47 (m, 2H), 7.26 (d, 2H), 7.17 (m, 2H), 3.05 (q, 2H), 1.37 (t, 3H).

Synthesis Examples for Process B from Scheme B

Process Step [V6]: 2-Ethyl-4-(4-fluorophenyl)-1,3-thiazole

A mixture of 2.40 g (11.0 mmol) of 2-bromo-1-(4-fluorophenyl)ethanone and 1.00 g (11.0 mmol) of thiopropanamide in 50 ml of ethanol is stirred under reflux for 2 h and at room temperature for 16 h. The reaction mixture is stirred into 200 ml of water and extracted with ethyl acetate (3×100 ml). The combined organic phases are washed with 50 ml of water, dried over MgSO$_4$ and freed from the solvent under reduced pressure. This gives 2.05 g (87%) of the desired product; $^1$H-NMR(DMSO-d6) δ: 7.99 (m, 2H), 7.92 (s, 1H), 7.26 (m, 2H), 3.04 (q, 2H), 1.34 (t, 3H).

Analogously, it is possible to prepare:

2-Isopropyl-4-(4-fluorophenyl)-1,3-thiazole $^1$H-NMR(DMSO-d6) δ: 7.99 (m, 2H), 7.94 (s, 1H), 7.26 (m, 2H), 3.33 (m, 1H), 1.37 (d, 6H).

Process Step [V8]: 5-Bromo-2-ethyl-4-(4-fluorophenyl)-1,3-thiazole

At room temperature, 1.72 g (9.64 mmol) of N-bromosuccinimide are added a little at a time to a solution of 2.00 g (9.64 mmol) of 2-ethyl-4-(4-fluorophenyl)-1,3-thiazole in 40 ml of dichloromethane. After 2 h, 50 ml of water are added to the reaction mixture, and the organic phase is separated off, washed with saturated NHCO$_3$ solution, dried over MgSO$_4$ and concentrated under reduced pressure. This gives 2.47 g (85%) of the desired product; $^1$H-NMR(DMSO-d6) δ: 7.92 (m, 2H), 7.32 (m, 2H), 3.02 (q, 2H), 1.31 (t, 3H).

Process Step [V7]: 4-[4-(4-Fluorophenyl)-2-isopropyl-1,3-thiazol-5-yl]-2-methylpyridine (Ex. 100)

Under argon, 200 mg (0.90 mmol) of 2-isopropyl-4-(4-fluorophenyl)-1,3-thiazole, 77 mg (0.45 mmol) of 4-bromo-2-methylpyridine, 133 mg (1.35 mmol) of potassium acetate and 0.4 mg (2 μmol) of palladium(II) acetate in 5 ml of DMA are heated to 150° C. After 3 h, 50 ml of ethyl acetate are added and the reaction mixture is filtered through a silica gel cartridge. 10 ml of water are added to the filtrate. The organic phase is separated off, washed once more with 10 ml of water, dried over MgSO$_4$ and concentrated under reduced pressure. The residue is purified by column chromatography on silica gel (cyclohexane/ethyl acetate). This gives 115 mg (41%) of the desired product; $^1$H-NMR(DMSO-(D6) δ: 8.39 (d, 1H), 7.48 (m, 2H), 7.22 (m, 2H), 7.17 (s, 1H), 7.03 (d, 1H), 3.35 (m, 1H), 2.43 (s, 3H), 1.39 (d, 6H).

Process Step [V9]: 4-[2-Ethyl-4-(4-fluorophenyl)-1,3-thiazol-5-yl]-2-methylpyridine (Ex. 96)

In a microwave reactor, 100 mg (0.35 mmol) of 5-bromo-2-ethyl-4-(4-fluorophenyl)-1,3-thiazole, 100 mg (0.45 mmol) of 2-methyl-4-(4,4,5,5-tetramethyl-1,3,2-dioxaborolan-2-yl)pyridine, 1 ml of a 1M caesium carbonate solution and 28.7 mg (0.04 mmol) of [1,1'-bis(diphenylphosphino)-ferrocene/palladium(II) dichloride dichloromethane complex] in 2.5 ml of THF are, under argon, heated at 90° C. for 25 min. The reaction mixture is then filtered, the filter cake is washed with ethyl acetate (3×5 ml) and the combined filtrate is concentrated under reduced pressure. The residue is purified by column chromatography on silica gel (cyclohexane/ethyl acetate). This gives 35 mg (24%) of the desired product; $^1$H-NMR(MeCN-d3) δ: 8.34 (d, 1H), 7.47 (m, 3H), 7.12 (s, 1H), 7.07 (m, 2H), 6.99 (d, 1H), 3.03 (q, 2H), 2.42 (s, 3H), 1.38 (t, 3H).

Synthesis Examples for Process C from Scheme C

Process Step [V12]: 4-[2-Ethyl-4-(4-fluorophenyl)-1,3-thiazol-5-yl]pyridine 1-oxide 3.9 ml (44 mmol) of a 30% strength hydrogen peroxide solution are added dropwise with cooling to a solution of 2.18 g (7.24 mmol) of 4-[2-ethyl-4-(4-fluorophenyl)-1,3-thiazol-5-yl]pyridine and 46.2 mg (0.19 mmol) of methyltrioxorhenium (VII) in 10 ml dichloromethane such that the temperature of the reaction mixture does not exceed 15° C., and the mixture is stirred at room temperature for 16 h. The reaction mixture is then diluted with 100 ml of dichloromethane, and the organic phase is washed successively with 30 ml of a saturated aqueous NaHCO$_3$ solution, 30 ml of a saturated Na$_2$SO$_3$ solution and 30 ml of water and dried over MgSO$_4$. Under reduced pressure, the product is freed from the solvent, giving 1.98 g (85%) of the desired product; $^1$H-NMR (DMSO-d6) δ: 8.12 (d, 2H), 7.53 (m, 2H), 7.25 (d, 2H), 7.21 (m, 2H), 3.03 (q, 2H), 1.36 (t, 3H).

Process Step [V13]: 2-Chloro-4-[2-ethyl-4-(4-fluorophenyl)-1,3-thiazol-5-yl]pyridine (Ex. 58)

A mixture of 1.90 g (6.33 mmol) of 4-[2-ethyl-4-(4-fluorophenyl)-1,3-thiazol-5-yl]pyridine 1-oxide and 40 ml of phosphoryl chloride is heated under reflux. After 8 h, the reaction mixture is concentrated under reduced pressure, the residue is taken up in 150 ml of dichloromethane and 50 ml of ice-water are added. The organic phase is separated off and once more washed with 50 ml of water, dried over MgSO$_4$ and freed from the solvent under reduced pressure. The residue is then purified by column chromatography on silica gel (cyclohexane/ethyl acetate). This gives 1.35 g (65%) of the desired product; $^1$H-NMR(DMSO-d6) δ: 8.35 (d, 1H), 7.49 (m, 2H), 7.35 (s, 1H), 7.25 (d, 1H), 7.19 (m, 2H), 3.06 (q, 2H), 1.37 (t, 3H).

Process Step [V14]: N-Benzyl-4-[2-ethyl-4-(4-fluorophenyl)-1,3-thiazol-5-yl]pyridine-2-amine (Ex. 59)

With stirring, a mixture of 5.24 g (16.4 mmol) of 2-chloro-4-[2-ethyl-4-(4-fluorophenyl)-1,3-thiazol-5-yl]pyridine and 25 ml benzylamine is heated at 180° C. After 16 h, the reaction mixture is concentrated under reduced pressure, the residue is taken up in 100 ml of MTBE, the resulting precipitate is filtered off and the filtrate is concentrated again. The residue is then purified by column chromatography on silica gel (cyclohexane/ethyl acetate). This gives 4.75 g (88%) of the desired product; $^1$H-NMR(MeCN-d3) δ: 7.91 (d, 1H), 7.49 (m, 2H), 7.29 (m, 5H), 7.07 (m, 2H), 6.45 (d, 1H), 6.39 (s, 1H), 5.83 (br.s, 1H), 4.43 (d, 2H), 3.02 (q, 2H), 1.38 (t, 3H).

Process Step [V15]: 4-[2-Ethyl-4-(4-fluorophenyl)-1,3-thiazol-5-yl]pyridine-2-amine (Ex. 35)

With ice cooling, 23 ml of conc. sulphuric acid are added to 4.75 g (10.9 mmol) of N-benzyl-4-[2-ethyl-4-(4-fluorophenyl)-1,3-thiazol-5-yl]pyridine-2-amine, and the reaction mixture is stirred at room temperature for 30 min. The reaction mixture is stirred into 100 ml of ice-water, the pH is adjusted to 10 using concentrated aqueous sodium hydroxide solution and the mixture is extracted with dichloromethane (3×100 ml). The combined organic phases are dried over MgSO$_4$ and freed from the solvent under reduced pressure. The residue is triturated with MTBE and filtered off. The product obtained is 2.80 g (82%) of a beige solid; log P (pH2.7): 1.29 with MS (ESI): 300.1 ([M+H]$^+$).

Process Step [V16]: N-{4-[2-Ethyl-4-(4-fluorophenyl)-1,3-thiazol-5-yl]pyridin-2-}butanamide (Ex. 83)

At room temperature, 82 mg (0.77) mmol of butyryl chloride are added dropwise to a solution of 200 mg (0.64 mmol) of 4-[2-ethyl-4-(4-fluorophenyl)-1,3-thiazol-5-yl]pyridine-2-amine and 125 mg (0.97 mmol) of diisopropylethylamine in 15 ml of THF. After 16 h, 50 ml of water are added, and the reaction mixture is extracted with ethyl acetate (3×50 ml). The combined organic phases are dried over MgSO$_4$ and freed from the solvent under reduced pressure. The residue is then purified by column chromatography on silica gel (cyclohexane/ethyl acetate). This gives 111 mg (45%) of the desired product; $^1$H-NMR(MeCN-d3) δ: 8.62 (br.s, 1H), 8.16 (m, 2H), 7.51 (m, 2H), 7.07 (m, 2H) 6.90 (d, 1H), 3.05 (q, 2H), 2.23 (t, 2H), 1.64 (m, 2H), 1.40 (t, 3H), 0.92 (t, 3H).

Process Step [V14]: N-Cyclopropyl-4-[2-ethyl-4-(4-fluorophenyl)-1,3-thiazol-5-yl]pyridine-2-amine (Ex. 72)

In a closed vessel, 600 mg (1.98 mmol) of 2-fluoro-4-[2-ethyl-4-(4-fluorophenyl)-1,3-thiazol-5-yl]pyridine (described, for example, in *J. Med. Chem*, 2005, 48, 5966-5979) in 10 ml cyclopropylamine are heated with stirring at 150° C. After 16 h, the reaction mixture is stirred into 100 ml of water and extracted with ethyl acetate (3×50 ml). The combined organic phases are dried over MgSO$_4$ and freed from the solvent under reduced pressure. The residue is then purified by column chromatography on silica gel (cyclohexane/ethyl acetate). This gives 520 mg (77%) of the desired product; $^1$H-NMR(DMSO-d6) δ: 7.96 (d, 1H), 7.52 (m, 2H), 7.17 (m, 2H), 6.65 (s, 1H), 6.49 (s 1H), 6.45 (d, 1H), 3.04 (q, 2H), 2.37 (m, 1H), 1.36 (t, 3H), 0.55 (m, 2H), 0.33 (m, 2H).

Process Step [V17]: N-Cyclopropyl-N-{4-[2-ethyl-4-(4-fluorophenyl)-1,3-thiazol-5-yl]pyridin-2-yl}acetamide (Ex. 80)

At 40° C., 35 mg (0.44) mmol of acetyl chloride are added dropwise to a solution of 100 mg (0.29 mmol) of N-cyclopropyl-4-[2-ethyl-4-(4-fluorophenyl)-1,3-thiazol-5-yl]pyridine-2-amine and 80 mg (0.58 mmol) of potassium carbonate in 5 ml acetonitrile. After 4 h, 30 ml of water are added, and the reaction mixture is extracted with ethyl acetate (3×25 ml). The combined organic phases are dried over MgSO$_4$ and freed from the solvent under reduced pressure. The residue is then purified by column chromatography on silica gel (cyclohexane/ethyl acetate). This gives 39 mg (31%) of the desired product; $^1$H-NMR(MeCN-d3) δ: 8.40 (d, 1H), 7.49 (m, 2H), 7.16 (d, 1H), 7.108 (m, 3H), 3.05 (q, 2H), 2.99 (m, 1H), 2.07 (s, 3H), 1.40 (t, 3H), 0.79 (m, 2H), 0.44 (m, 2H).

Process Step [V19]: N-Cyclopropyl-4-[2-ethyl-4-(4-fluorophenyl)-1,3-thiazol-5-yl]pryridine-2-carboxamide (Ex. 75)

Under argon, 250 mg (0.78 mmol) of 2-chloro-4-[2-ethyl-4-(4-fluorophenyl)-1,3-thiazol-5-yl]pyridine, 207 mg (0.78 mmol) of Mo(CO)$_6$, 134 mg (2.35 mmol) of cyclopropylamine, 358 mg (2.35 mmol) of DBU and 90 mg (0.08 mmol) of Pd(PPh$_3$)$_4$ in 5 ml DMF are heated at 90° C. After 16 h, the reaction mixture is concentrated under reduced pressure. The residue is then purified by column chromatography on silica gel (cyclohexane/ethyl acetate). This gives 140 mg (45%) of the desired product; $^1$H-NMR(DMSO-d6) δ: 8.73 (d, 1H), 8.56 (d, 1H), 7.87 (s, 1H), 7.48 (m, 3H), 7.21 (m, 2H), 3.09 (q, 2H), 2.89 (m, 1H), 1.36 (t, 3H), 0.67 (m, 4H).

The use of the active compounds of the formula (I) is illustrated by the examples below. However, the invention is not limited to these examples.

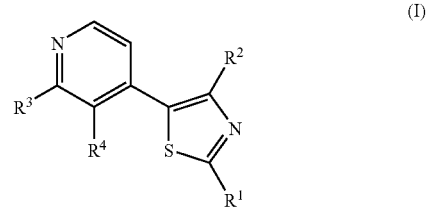

(I)

The following exemplary compounds of Table 1 are known, and their use is claimed according to Claims 7 to 11:

TABLE 1

| Ex. | R$^1$ | R$^2$ | R$^3$ | R$^4$ |
|---|---|---|---|---|
| 1 | amino | furan-2-yl | H | H |
| 2 | amino | 3-methylphenyl | H | H |
| 3 | ethyl | 3-methylphenyl | H | H |
| 4 | 4-methylphenyl | 3-methylphenyl | H | H |
| 5 | ethyl | 3-methylphenyl | (phenylcarbonyl)amino | H |
| 6 | amino | 4-fluorophenyl | H | H |
| 7 | 4-(methylsulphanyl)phenyl | 4-fluorophenyl | H | H |
| 8 | 4-hydroxyphenyl | 3-methylphenyl | H | H |
| 9 | 4-(methylsulphonyl)phenyl | 4-fluorophenyl | H | H |
| 10 | 4-(methylsulphinyl)phenyl | 4-fluorophenyl | H | H |
| 11 | 4-(methylsulphinyl)phenyl | 3-methylphenyl | H | H |
| 12 | ethyl | 3-methylphenyl | amino | H |
| 13 | acetylamino | 3-methylphenyl | H | H |
| 14 | methylamino | 3-methylphenyl | H | H |
| 15 | acetyl(methyl)amino | 3-methylphenyl | H | H |
| 16 | CH$_3$ | 3-methylphenyl | H | H |
| 17 | methylamino | 4-fluorophenyl | H | H |
| 18 | phenyl | 4-fluorophenyl | H | H |
| 19 | amino | phenyl | H | H |
| 20 | amino | 2-chlorophenyl | H | H |
| 21 | H | 4-fluorophenyl | H | H |
| 22 | amino | 3-ethylphenyl | H | H |
| 23 | amino | 2-methylphenyl | H | H |
| 24 | ethyl | 3-methylphenyl | acetylamino | H |
| 25 | amino | 4-methylphenyl | H | H |
| 26 | ethyl | 4-methylphenyl | H | H |
| 27 | ethyl | 4-chlorophenyl | H | H |
| 28 | ethyl | phenyl | H | H |
| 29 | amino | 3-methoxyphenyl | H | H |
| 30 | ethyl | 3-chlorophenyl | H | H |
| 31 | ethyl | 4-fluorophenyl | (phenylcarbonyl)amino | H |
| 32 | ethyl | 4-fluorophenyl | acetylamino | H |
| 33 | ethyl | 4-fluorophenyl | propanoylamino | H |
| 34 | ethyl | 3-methylphenyl | pyrrolidin-1-yl | H |
| 35 | ethyl | 4-fluorophenyl | amino | H |
| 36 | ethyl | 3-methylphenyl | propanoylamino | H |
| 37 | ethyl | 3-methylphenyl | (2,2-dimethylpropanoyl)amino | H |
| 38 | ethyl | 3-methylphenyl | (4-methoxybenzoyl)amino | H |
| 39 | ethyl | 3-methylphenyl | (thiophen-2-ylcarbonyl)amino | H |
| 40 | ethyl | 3-methylphenyl | (phenylacetyl)amino | H |

The following exemplary compounds of Table 2 are novel, and they are claimed according to any of Claims 1 to 3:

TABLE 2

| Ex. | R1 | R2 | R3 | R4 | NMR Data | log p |
|---|---|---|---|---|---|---|
| 41 | ethyl | 4-fluorophenyl | H | H | $^1$H-NMR (DMSO-d6) δ: 8.53 (d, 2H), 7.47 (m, 2H), 7.26 (d, 2H), 7.17 (m, 2H), 3.05 (q, 2H), 1.37 (t, 3H) | 2.01[a]; 2.89[c] |
| 42 | ethyl | 5-chlorothiophen-2-yl | H | H | $^1$H-NMR (DMSO-d6) δ: 8.69 (d, 2H), 7.56 (d, 2H), 6.98 (d, 1H), 6.86 (d, 1H), 3.05 (q, 2H), 1.35 (t, 3H). | 3.88[c]; 3.06[b] |

TABLE 2-continued

| Ex. | R1 | R2 | R3 | R4 | NMR Data | log p |
|---|---|---|---|---|---|---|
| 43 | propan-2-yl | 4-fluorophenyl | H | H | ¹H-NMR (DMSO-d6) δ: 8.55 (d, 2H), 7.48 (m, 2H), 7.30 (d, 2H), 7.20 (m, 2H), 3.37 (m, 1H), 1.40 (d, 6H). | 3.71[c]; 2.56[b] |
| 44 | CH₃ | 4-fluorophenyl | H | H | ¹H-NMR (DMSO-d6) δ: 8.55 (d, 2H), 7.46 (m, 2H), 7.27 (d, 2H), 7.20 (m, 2H), 2.73 (s, 3H). | 1.48[b] |
| 45 | benzyl | 4-fluorophenyl | H | H | ¹H-NMR (DMSO-d6) δ: 8.52 (d, 2H), 7.38 (m, 6H), 7.25 (m, 5H), 4.40 (s, 2H). | 2.94[b] |
| 46 | tert-butyl | 4-fluorophenyl | H | H | ¹H-NMR (DMSO-d6) δ: 8.55 (d, 2H), 7.47 (m, 2H), 7.30 (d, 2H), 7.21 (m, 2H), 1.45 (s, 9H). | 3.29[b] |
| 47 | butyl | 4-fluorophenyl | H | H | ¹H-NMR (DMSO-d6) δ: 8.55 (d, 2H), 7.49 (m, 2H), 7.28 (d, 2H), 7.21 (m, 2H), 3.04 (t, 2H), 1.76 (m, 2H), 1.43 (m, 2H), 0.94 (t, 3H). | 3.11[b] |
| 48 | ethyl | 3,4-dimethylphenyl | H | H | ¹H-NMR (DMSO-d6) δ: 8.52 (d, 2H), 7.28 (m, 3H), 7.08 (m, 2H), 3.05 (q, 2H), 2.23 (s, 3H), 2.19 (s, 3H), 1.36 (t, 3H). | 2.49[b] |
| 49 | ethyl | 3-(trifluoromethyl)-phenyl | H | H | ¹H-NMR (DMSO-d6) δ: 8.58 (d, 2H), 7.71 (m, 3H), 7.59 (m, 1H), 7.33 (d, 2H), 3.08 (q, 2H), 1.38 (t, 3H). | 3[b] |
| 50 | ethyl | 4-fluorophenyl | (4-methyl-benzoyl)amino | H | ¹H-NMR (DMSO-d6) δ: 10.80 (s, 1H), 8.32 (d, 1H), 8.26 (s, 1H), 7.91 (d, 2H), 7.53 (m, 2H), 7.31 (d, 2H), 7.21 (m, 2H), 6.98 (d, 1H), 3.07 (q, 2H), 2.38 (s, 3H), 1.38 (t, 3H). | 4.48[b] |
| 51 | ethyl | 4-fluorophenyl | (2,2-dimethyl-propanoyl)amino | H | ¹H-NMR (DMSO-d6) δ: 9.88 (s, 1H), 8.26 (s, 1H), 8.14 (s, 1H), 7.50 (m, 2H), 7.20 (m, 2H), 6.89 (d, 1H), 3.06 (q, 2H), 1.37 (t, 3H), 1.22 (s, 9H). | 4.18[b] |
| 52 | ethyl | 4-fluorophenyl | (4-fluorobenzoyl)-amino | H | ¹H-NMR (DMSO-d6) δ: 10.93 (s, 1H), 8.33 (d, 1H), 8.24 (s, 1H), 8.07 (m, 2H), 7.52 (m, 2H), 7.33 (m, 2H), 7.21 (m, 2H), 6.99 (d, 1H), 3.07 (q, 2H), 1.38 (t, 3H). | 4.18[b] |
| 53 | ethyl | 4-fluorophenyl | (4-methoxy-benzoyl)amino | H | ¹H-NMR (DMSO-d6) δ: 10.72 (s, 1H), 8.32 (d, 1H), 8.26 (s, 1H), 8.01 (d, 2H), 7.52 (m, 2H), 7.21 (m, 2H), 7.03 (d, 2H), 6.96 (d, 1H), 3.84 (s, 3H), 3.07 (q, 2H), 1.38 (t, 3H). | 4.04[b] |
| 54 | ethyl | 4-fluorophenyl | (cyclohexylcarbonyl)amino | H | ¹H-NMR (DMSO-d6) δ: 10.45 (s, 1H), 8.22 (d, 1H), 8.16 (s, 1H), 7.49 (m, 2H), 7.19 (m, 2H), 6.86 (d, 1H), 3.05 (q, 2H), 1.75 (m, 4H), 1.64 (m, 1H), 1.36 (t, 3H), 1.20 (m, 5H). | 4.54[b] |
| 55 | ethyl | 4-fluorophenyl | (3-phenyl-propanoyl)amino | H | ¹H-NMR (DMSO-d6) δ: 10.58 (s, 1H), 8.24 (d, 1H), 8.14 (s, 1H), 7.49 (m, 2H), 7.23 (m, 7H), 6.90 (d, 1H), 3.06 (q, 2H), 2.87 (t, 2H), 2.69 (t, 2H), 1.37 (t, 3H). | 4.23[b] |
| 56 | ethyl | 4-fluorophenyl | (thiophen-2-ylcarbonyl)amino | H | ¹H-NMR (DMSO-d6) δ: 11.00 (s, 1H), 8.33 (d, 1H), 8.23 (s, 1H), 8.20 (s, 1H), 7.88 (d, 1H), 7.51 (m, 2H), 7.21 (m, 3H), 6.99 (d, 1H), 3.07 (q, 2H), 1.37 (t, 3H). | 3.92[b] |
| 57 | ethyl | 4-fluorophenyl | (thiophen-3-ylcarbonyl)amino | H | ¹H-NMR (DMSO-d6) δ: 10.76 (s, 1H), 8.55 (s, 1H), 8.33 (d, 1H), 8.25 (s, 1H), 7.67 (d, 1H), 7.63 (d, 1H), 7.52 (m, 2H), 7.21 (m, 2H), 6.97 (d, 1H), 3.07 (q, 2H), 1.37 (t, 3H). | 3.83[b] |
| 58 | ethyl | 4-fluorophenyl | chlorine | H | ¹H-NMR (DMSO-d6) δ: 8.35 (d, 1H), 7.49 (m, 2H), 7.35 (s, 1H), 7.25 (d, 1H), 7.19 (m, 2H), 3.06 (q, 2H), 1.37 (t, 3H). | 4.1[c]; 4.07[b] |
| 59 | ethyl | 4-fluorophenyl | benzylamino | H | ¹H-NMR (MeCN-d3) δ: 7.91 (d, 1H), 7.49 (m, 2H), 7.29 (m, 5H), 7.07 (m, 2H), 6.45 (d, 1H), 6.39 (s, 1H), 5.83 (br.s, 1H), 4.43 (d, 2H), 3.02 (q, 2H), 1.38 (t, 3H). | 2.32[b] |
| 60 | ethyl | 4-fluorophenyl | phenylamino | H | ¹H-NMR (DMSO-d6) δ: 9.07 (s, 1H), 8.11 (d, 1H), 7.56 (m, 4H), 7.23 (m, 4H), 6.89 (t, 1H), 6.76 (s, 1H), 6.60 (d, 1H), 3.05 (q, 2H), 1.36 (t, 3H). | 3.1[b] |
| 61 | ethyl | 4-fluorophenyl | (1-phenyl-ethyl)amino | H | ¹H-NMR (DMSO-d6) δ: 7.86 (d, 1H), 7.48 (m, 2H), 7.29 (m, 4H), 7.18 (m, 3H), 7.11 (m, 2H), 6.43 (s, 1H), 6.28 (d, 1H), 4.95 (m, 1H), 3.02 (q, 2H), 1.34 (m, 6H). | 2.39[b] |
| 62 | ethyl | 4-fluorophenyl | (2-phenyl-ethyl)amino | H | ¹H-NMR (DMSO-d6) δ: 7.95 (d, 1H), 7.52 (m, 2H), 7.28 (m, 2H), 7.21 (m, 5H), 6.72 (m, 1H), 6.39 (s, 1H), 6.33 (d, 1H), 3.03 (q, 2H), 2.77 (t, 2H), 1.35 (t, 3H). | 2.17[b] |
| 63 | ethyl | 4-fluorophenyl | cyclopentylamino | H | ¹H-NMR (DMSO-d6) δ: 7.91 (d, 1H), 7.51 (m, 2H), 7.20 (m, 2H), 6.62 (d, 1H), 6.37 (s, 1H), 6.29 (d, 1H), 3.99 (m, 1H), 3.02 (q, 2H), 1.83 (m, 2H), 1.64 (m, 3H), 1.51 (m, 2H), 1.34 (m, 5H). | 1.94[b] |
| 64 | ethyl | 4-fluorophenyl | pyrrolidin-1-yl | H | ¹H-NMR (DMSO-d6) δ: 8.00 (d, 1H), 7.51 (m, 2H), 7.20 (m, 2H), 6.37 (d, 1H), 6.30 (s, 1H), 3.03 (q, 2H), 1.90 (m, 4H), 1.35 (t, 3H). | 2[b] |
| 65 | ethyl | 4-fluorophenyl | (tert-butoxy-carbonyl)amino | H | ¹H-NMR (DMSO-d6) δ: 9.85 (s, 1H), 8.18 (d, 1H), 7.81 (s, 1H), 7.49 (m, 2H), 7.20 (m, 2H), 6.83 (d, 1H), 3.05 (q, 2H), 1.44 (s, 9H), 1.36 (t, 3H). | 4.63[b] |
| 66 | butyl | 4-fluorophenyl | (phenylcarbonyl)-amino | H | ¹H-NMR (DMSO-d6) δ: 10.88 (s, 1H), 8.33 (d, 1H), 8.26 (s, 1H), 7.99 (d, 2H), 7.59 (m, 1H), 7.51 (m, 4H), 7.21 (m, 2H), 6.90 (d, 1H), 3.05 (t, 2H), 1.78 (m, 2H), 1.44 (m, 2H), 0.95 (t, 3H). | 5.07[b] |
| 67 | ethyl | 4-fluorophenyl | benzoyl(methyl)-amino | H | ¹H-NMR (DMSO-d6) δ: 8.29 (d, 1H), 7.32 (m, 5H), 7.26 (m, 4H), 7.08 (s, 1H), 6.95 (d, 1H), 3.02 (q, 2H), 1.32 (t, 3H). | 3.68[b] |
| 68 | ethyl | 4-fluorophenyl | acetyl(methyl)-amino | H | 1H-NMR (DMSO-d6) δ: 8.44 (d, 1H), 7.49 (m, 2H), 7.41 (s, 1H), 7.19 (m, 3H), 3.06 (q, 2H), 1.96 (s, 3H), 1.36 (t, 3H). | 2.71[b] |
| 69 | ethyl | phenyl | (phenylcarbonyl)amino | H | ¹H-NMR (DMSO-d6) δ: 10.87 (s, 1H), 8.31 (d, 1H), 8.28 (s, 1H), 7.99 (d, 2H), 7.60 (m, 1H), 7.50 (m, 4H), 7.48 (m, 3H), 6.97 (d, 1H), 3.07 (q, 2H), 1.38 (t, 3H). | 3.91[b] |

TABLE 2-continued

| Ex. | R1 | R2 | R3 | R4 | NMR Data | log p |
|---|---|---|---|---|---|---|
| 70 | ethyl | 4-fluorophenyl | (1-methoxy-propan-2-yl)amino | H | 1H-NMR (DMSO-d6) δ: 7.91 (d, 1H), 7.52 (m, 2H), 7.16 (m, 2H), 6.43 (s, 1H), 6.30 (d, 1H), 6.25 (d, 1H), 4.04 (m, 1H), 3.36 (m, 1H), 3.25 (s, 3H), 3.22 (m, 1H), 3.03 (q, 2H), 1.35 (t, 3H), 1.09 (d, 3H). | 1.78[b] |
| 71 | ethyl | 4-fluorophenyl | (1-hydroxy-propan-2-yl)amino | H | 1H-NMR (DMSO-d6) δ: 7.89 (d, 1H), 7.53 (m, 2H), 7.17 (m, 2H), 6.44 (s, 1H), 6.29 (d, 1H), 6.20 (d, 1H), 3.86 (m, 1H), 3.446 (m, 1H), 3.31 (m, 1H), 3.03 (q, 2H), 1.35 (t, 3H), 1.08 (d, 3H). | 1.44[b] |
| 72 | ethyl | 4-fluorophenyl | cyclopropylamino | H | 1H-NMR (DMSO-d6) δ: 7.96 (d, 1H), 7.52 (m, 2H), 7.17 (m, 2H), 6.65 (s, 1H), 6.49 (s 1H), 6.45 (d, 1H), 3.04 (q, 2H), 2.37 (m, 1H), 1.36 (t, 3H), 0.55 (m, 2H), 0.33 (m, 2H). | 3.61[c]; 1.74[b] |
| 73 | ethyl | 4-fluorophenyl | ethyl(methyl)-carbamoyl | H | 1H-NMR (DMSO-d6) δ: 8.54 (d, 1H), 7.49 (m, 2H), 7.36 (m, 2H), 7.21 (m, 2H), 3.44 and 3.21 (q, together 2H), 3.08 (q, 2H), 1.37 (t, 3H), 1.10 and 1.03 (t, together 3H). | 2.87[c]; 2.81[b] |
| 74 | ethyl | 4-fluorophenyl | prop-2-en-1-ylamino | H | 1H-NMR (DMSO-d6) δ: 7.92 (d, 1H), 7.51 (m, 2H), 7.20 (m, 2H), 6.79 (m, 1H), 6.41 (s, 1H), 6.34 (d, 1H), 5.85 (m, 1H), 5.13 (d, 1H), 5.03 (d, 1H), 3.83 (m, 2H), 3.03 (q, 2H), 1.34 (t, 3H). | 3.8[c]; 1.67[b] |
| 75 | ethyl | 4-fluorophenyl | cyclopropyl-carbamoyl | H | 1H-NMR (DMSO-d6) δ: 8.73 (d, 1H), 8.56 (d, 1H), 7.87 (s, 1H), 7.48 (m, 3H), 7.21 (m, 2H), 3.09 (q, 2H), 2.89 (m, 1H), 1.36 (t, 3H), 0.67 (m, 4H). | 3.5[c]; 3.46[b] |
| 76 | ethyl | 4-fluorophenyl | ethylamino | H | 1H-NMR (DMSO-d6) δ: 7.92 (d, 1H), 7.51 (m, 2H), 7.20 (m, 2H), 6.59 (m, 1H), 6.36 (s, 1H), 6.30 (d, 1H), 3.19 (m, 2H), 3.02 (q, 2H), 1.35 (t, 3H), 1.08 (t, 3H). | 3.64[c]; 1.54[b] |
| 77 | ethyl | 4-fluorophenyl | (2-hydroxy-propyl)amino | H | 1H-NMR (DMSO-d6) δ: 7.89 (d, 1H), 7.51 (m, 2H), 7.20 (m, 2H), 6.61 (m, 1H), 6.47 (s, 1H), 6.29 (d, 1H), 4.70 (d, 1H), 3.74 (m, 1H), 3.14 (m, 2H), 3.02 (q, 2H), 1.35 (t, 3H), 1.04 (d, 3H). | 2.74[c]; 1.44[b] |
| 78 | ethyl | 4-fluorophenyl | (2-methoxy-propyl)amino | H | 1H-NMR (DMSO-d6) δ: 7.87 (m, 2H), 7.54 (m, 2H), 7.22 (m, 2H), 6.83 (s, 1H), 6.46 (s, 1H), 3.45 (m, 1H), 3.25 (s, 3H), 3.05 (q, 2H), 2.90 (m, 1H), 2.73 (m, 1H), 1.36 (t, 3H), 1.11 (d, 3H). | 3.67[c]; 1.73[b] |
| 79 | ethyl | 4-fluorophenyl | (2,2-difluoro-ethyl)amino | H | 1H-NMR (DMSO-d6) δ: 7.96 (d, 1H), 7.51 (m, 2H), 7.20 (m, 2H), 7.05 (m, 1H), 6.54 (s, 1H), 6.40 (d, 1H), 6.07 (tt, 1H), 3.67 (m, 2H), 3.03 (q, 2H), 1.35 (t, 3H). | 3.76[c]; 2.39[b] |
| 80 | ethyl | 4-fluorophenyl | acetyl(cyclo-propyl)amino | H | 1H-NMR (MeCN-d3) δ: 8.40 (d, 1H), 7.49 (m, 2H), 7.16 (d, 1H), 7.108 (m, 3H), 3.05 (q, 2H), 2.99 (m, 1H), 2.07 (s, 3H), 1.40 (t, 3H), 0.79 (m, 2H), 0.44 (m, 2H). | 2.88[c]; 2.81[b] |
| 81 | ethyl | 4-fluorophenyl | (methoxyacetyl)-amino | H | 1H-NMR (MeCN-d3) δ: 8.77 (br.s, 1H), 8.20 (d, 1H), 8.15 (s, 1H), 7.51 (m, 2H), 7.08 (m, 2H), 6.97 (d, 1 H), 3.97 (s, 2H), 3.45 (s, 3H), 3.05 (q, 2H), 2.63 (m, 1H), 1.41 (t, 3H). | 3.21[c]; 3.17[b] |
| 82 | ethyl | 4-fluorophenyl | (2-methyl-propanoyl)amino | H | 1H-NMR (MeCN-d3) δ: 8.62 (br.s, 1H), 8.18 (s, 1H), 8.25 (d, 1H), 7.50 (m, 2H), 7.08 (m, 2H), 6.89 (d, 1 H), 3.05 (q, 2H), 2.63 (m, 1H), 1.41 (t, 3H), 1.12 (d, 6H). | 3.66[c]; 3.52[b] |
| 83 | ethyl | 4-fluorophenyl | butanoylamino | H | 1H-NMR (MeCN-d3) δ: 8.62 (br.s, 1H), 8.16 (m, 1H), 7.51 (m, 2H), 7.07 (m, 2H), 6.90 (d, 1 H), 3.05 (q, 2H), 2.23 (t, 2H), 1.64 (m, 2H), 1.40 (t, 3H), 0.92 (t, 3H). | 3.58[c]; 3.45[b] |
| 84 | ethyl | 4-fluorophenyl | (cyclobutylcarbonyl)amino | H | 1H-NMR (MeCN-d3) δ: 8.45 (br.s, 1H), 8.19 (s, 1H), 8.14 (d, 1H), 7.51 (m, 2H), 7.08 (m, 2H), 6.90 (d, 1 H), 3.28 (m, 1H), 3.05 (q, 2H), 1.44 (t, 3H). | 3.82[c]; 3.68[b] |
| 85 | ethyl | 4-fluorophenyl | (ethoxycarbonyl)-amino | H | 1H-NMR (MeCN-d3) δ: 8.13 (d, 1H), 8.09 (br.s, 1H), 7.90 (s, 1H), 7.51 (m, 2H), 7.08 (m, 2H), 6.89 (d, 1 H), 4.16 (q, 2H), 3.05 (q, 2H), 1.40 (t, 3H), 1.25 (t, 3H). | 3.69[c]; 3.61[b] |
| 86 | ethyl | 4-fluorophenyl | (cyclopropyl-carbonyl)amino | H | 1H-NMR (MeCN-d3) δ: 8.94 (br.s, 1H), 8.15 (m, 2H), 7.50 (m, 2H), 7.07 (m, 2H), 6.90 (d, 1 H), 3.04 (q, 2H), 1.78 (m, 1H), 1.39 (t, 3H), 0.88 (m, 4H). | 3.37[c]; 3.22[b] |
| 87 | ethyl | 4-fluorophenyl | (methoxycarbonyl)amino | H | 1H-NMR (MeCN-d3) δ: 8.13 (m, 2H), 7.90 (s, 1H), 7.51 (m, 2H), 7.08 (m, 2H), 6.88 (d, 1 H), 3.70 (s, 3H), 3.05 (q, 2H), 1.40 (t, 3H). | 3.22[c]; 3.14[b] |
| 88 | difluoro-methyl | 4-fluorophenyl | H | H | 1H-NMR (DMSO-d6) δ: 8.62 (d, 2H), 7.50 (m, 2H), 7.40 (m, 2H), 7.24 (m, 2H), 6.34 (s, 1H). | 3.01[c]; 2.48[b] |
| 89 | cyclo-propyl | 4-fluorophenyl | H | H | 1H-NMR (MeCN-d3) δ: 8.47 (d, 2H), 7.45 (m, 2H), 7.20 (d, 2H), 7.08 (m, 2H), 2.37 (m, 1H), 1.18 (m, 2H), 1.12 (m, 2H). | 3.32[c]; 2.16[b] |
| 90 | ethyl | 4-fluorophenyl | (2-methyl-acryloyl)amino | H | 1H-NMR (MeCN-d3) δ: 8.63 (br.s, 1H), 8.20 (m, 2H), 7.51 (m, 2H), 7.08 (m, 2H), 6.94 (d, 1 H), 5.84 (s, 1H), 5.54 (s, 1H), 3.05 (q, 2H), 1.99 (s, 3H), 1.42 (t, 3H), 1.14 (m, 2H), 0.70 (m, 2H). | 3.71[c]; 3.6[b] |
| 91 | ethyl | 4-fluorophenyl | (methylsulphonyl)amino | H | 1H-NMR (MeCN-d3) δ: 8.51 (br.s, 1H), 8.13 (d, 1H), 7.51 (m, 2H), 7.11 (m, 2H), 6.90 (d, 1H), 6.94 (s, 1 H), 3.14 (s, 3H), 3.05 (q, 2H), 1.40 (t, 3H). | 2.18[c]; 2.36[b] |
| 92 | ethyl | 4-fluorophenyl | bis(methylsulphonyl)amino | H | 1H-NMR (MeCN-d3) δ: 8.49 (d, 1H), 7.49 (m, 2H), 7.43 (d, 1H), 7.35 (s, 1 H), 7.10 (m, 2H), 3.44 (s, 6H), 3.07 (q, 2H), 1.41 (t, 3H). | 3.24[c]; 3.23[b] |
| 93 | ethyl | 4-fluorophenyl | bis[(propan-2-yloxy)carbonyl]-amino | H | 1H-NMR (MeCN-d3) δ: 8.35 (d, 1H), 7.48 (m, 2H), 7.29 (s, 1H), 7.20 (d, 1H), 7.10 (m, 2H), 4.95 (m, 2 H), 3.06 (q, 2H), 1.40 (t, 3H), 1.19 (d, 12H). | 4.49[c]; 4.5[b] |

TABLE 2-continued

| Ex. | R1 | R2 | R3 | R4 | NMR Data | log p |
|---|---|---|---|---|---|---|
| 94 | ethyl | 4-fluorophenyl | [(propan-2-yloxy)-carbonyl]amino | H | $^1$H-NMR (MeCN-d3) δ: 8.12 (d, 1H), 8.01 (br.s, 1H), 7.90 (s, 1H), 7.51 (m, 2H), 7.08 (m, 2H), 6.87 (d, 1 H), 4.91 (m, 1 H), 3.06 (q, 2H), 1.42 (t, 3H), 1.25 (d, 6H). | 4.18[c]; 4.08[b] |
| 95 | ethyl | 4-fluorophenyl | [(1-methylcyclo-propyl)carbonyl]-amino | H | 1H-NMR (MeCN-d3) δ: 8.34 (br.s, 1H), 8.16 (m, 2H), 7.50 (m, 2H), 7.07 (m, 2H), 6.91 (d, 1 H), 3.05 (q, 2H), 1.44 (s, 3H), 1.40 (t, 3H), 1.14 (m, 2H), 0.70 (m, 2H). | 4.03[c]; 3.89[b] |
| 96 | ethyl | 4-fluorophenyl | CH$_3$ | H | $^1$H-NMR (MeCN-d3) δ: 8.34 (d, 1H), 7.47 (m, 3H), 7.12 (s, 1H), 7.07 (m, 2H), 6.99 (d, 1H), 3.03 (q, 2H), 2.42 (s, 3H), 1.38 (t, 3H) | 1.68[b] |
| 97 | ethyl | 4-fluorophenyl | diacetylamino | H | 1H-NMR (DMSO-d6) δ: 8.55 (d, 1H), 7.49 (m, 2H), 7.41 (d, 1H), 7.39 (s, 1H), 7.19 (m, 2H), 6.27 (d, 1H), 3.08 (q, 2H), 2.14 (s, 6H), 1.36 (t, 3H). | 2.95[c]; 2.95[b] |
| 98 | ethyl | 4-fluorophenyl | (chloroacetyl)-amino | H | $^1$H-NMR (MeCN-d3) δ: 8.92 (br.s, 1H), 8.21 (d, 1H), 8.09 (s, 1H), 7.52 (m, 2H), 7.08 (m, 2H), 6.96 (d, 1H), 7.03 (d, 1H), 4.19 (s, 2H), 3.05 (q, 2H), 1.39 (t, 3H). | 3.32[c]; 3.29[b] |
| 99 | ethyl | 4-fluorophenyl | (3-methylbutanoyl)amino | H | 1H-NMR (MeCN-d3) δ: 8.63 (br.s, 1H), 8.16 (m, 2H), 7.50 (m, 2H), 7.08 (m, 2H), 6.90 (d, 1 H), 3.05 (q, 2H), 1.77 (m, 1 H), 1.41 (t, 3H), 0.95 (d, 6H). | 4.04[c]; 3.91[b] |
| 100 | propan-2-yl | 4-fluorophenyl | CH$_3$ | H | $^1$H-NMR (DMSO-d6) δ: 8.39 (d, 1H), 7.48 (m, 2H), 7.22 (m, 2H), 7.17 (s, 1H), 7.03 (d, 1H), 3.35 (m, 1H), 2.43 (s, 3H), 1.39 (d, 6H). | 4.06[c]; 2.1[b] |
| 101 | ethyl | 4-fluorophenyl | propan-2-ylamino | H | 1H-NMR (DMSO-d6) δ: 7.91 (d, 1H), 7.51 (m, 2H), 7.20 (m, 2H), 6.51 (br.s, 1H), 6.38 (s, 1H), 6.27 (d, 1H), 3.92 (m, 1H), 3.03 (q, 2H), 1.35 (t, 3H), 1.16 (d, 6H). | 4.11[c]; 1.73[b] |
| 102 | ethyl | 4-fluorophenyl | acetyl(prop-2-yn-1-yl)amino | H | $^1$H-NMR (MeCN-d3) δ: 8.42 (d, 1H), 7.51 (m, 2H), 7.30 (s, 1H), 7.23 (d, 1H), 7.10 (m, 2 H), 4.51 (s, 2H), 3.06 (q, 2H), 2.39 (s, 1H), 1.40 (s, 3H). | 3.02[c]; 3.03[b] |
| 103 | ethyl | thiophen-2-yl | H | H | 1H-NMR (DMSO-d6) δ: 8.65 (d, 2H), 7.53 (d, 1H), 7.48 (d, 2H), 7.01 (m, 2H), 3.03 (q, 2H), 1.35 (t, 3H). | 1.94[b] |

The log P values were determined in accordance with EEC Directive 79/831 Annex V.A8 by HPLC (High Performance Liquid Chromatography) on reversed-phase columns (C18), using the methods below:
[a]The determination is carried out in the acidic range at pH 2.3 using the mobile phases 0.1% aqueous phosphoric acid and acetonitrile; linear gradient from 10% acetonitrile to 95% acetonitrile.
[b]The determination by LC-MS in the acidic range is carried out at pH 2.7 using the mobile phases 0.1% aqueous formic acid and acetonitrile (contains 0.1% formic acid); linear gradient from 10% acetonitrile to 95% acetonitrile.
[c]The determination by LC-MS in the neutral range is carried out at pH 7.8 using the mobile phases 0.001 molar aqueous ammonium bicarbonate solution and acetonitrile; linear gradient from 10% acetonitrile to 95% acetonitrile.
Calibration is carried out using unbranched alkan-2-ones (having 3 to 16 carbon atoms) with known logP values (determination of the logP values by the retention times using linear interpolation between two successive alkanones).
The lambda-max values were determined in the maxima of the chromatographic signals using the UV spectra from 200 nm to 400 nm.

USE EXAMPLES

Example 1

*Alternaria* test (tomato)/protective

Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. One day after the treatment, the plants are inoculated with a spore suspension of *Alternaria solani* and then remain at 100% relative humidity and 22° C. for 24 h. The plants then remain at 96% relative atmospheric humidity and a temperature of 20° C.

Evaluation is carried out 7 days after the inoculation. 0% means an efficacy which corresponds to that of the control, whereas an efficacy of 100% means that no infection is observed.

In this test, the exemplary compounds according to the invention Nos. 2, 3, 5, 6, 9, 12, 14, 16, 17, 21, 22, 24, 26, 32, 33, 35, 36, 37, 38, 39, 40, 41, 42, 47, 51, 58, 71, 72, 74, 76, 79 and 104 of Tables 1 and 2 show, at an active compound concentration of 500 ppm, an efficacy of 70% or more.

Example 2

Production of Fumonisin FB1 by *Fusarium proliferatum*

The compounds were tested in microtitre plates at 5 concentrations of from 0.08 μM to 50 μM in a fumonisin-inducing liquid medium (0.5 g of malt extract, 1 g of yeast extract, 1 g of bactopeptone, 20 g of fructose, 1 g of KH$_2$PO$_4$, 0.3 g of MgSO$_4$×7H$_2$O, 0.3 g of KCl, 0.05 g of ZnSO$_4$×7H$_2$O and 0.01 g of CuSO$_4$×5H$_2$O per liter) with DMSO (0.5%). Inoculation was carried out using a concentrated spore suspension of *Fusarium proliferatum* at a final concentration of 2000 spores/ml.

The plate was incubated at high atmospheric humidity and 20° C. for 5 days.

At the beginning and after 5 days, an OD measurement at OD620 (multiple measurements: 3×3 measurements per well) was carried out to determine inhibition of growth.

After 5 days, a sample of the liquid medium was removed and diluted 1:1000 with 50% strength acetonitrile. The FB1 concentration of the diluted samples was analyzed by HPLC-MS/MS, and the measured values were used to calculate the inhibition of fumonisin FB1 production compared to an active compound-free control.

Examples of the Inhibition of Fumonisin FB1 Production

In this test, the exemplary compounds according to the invention Nos. 1, 2, 3, 4, 5, 6, 7, 8, 9, 10, 11, 16, 17, 18, 19 and 41 of Tables 1 and 2 show, at a concentration of 50 μM, an activity of >70% in the inhibition of FB1 production. The inhibition of the growth of *Fusarium proliferatum* of the examples mentioned below varied from 0 to 94% at 50 µM.

Example 3

Production of DON/Acetyl-DON by *Fusarium graminearum*

The compounds were tested in microtitre plates at 7 concentrations of 0.07 µM to 50 µM in a DON-inducing liquid medium (1 g of $(NH_4)_2HPO_4$, 0.2 g of $MgSO_4\times7$ $H_2O$, 3 g of $KH_2PO_4$, 10 g of glycerol, 5 g of NaCl and 40 g of sucrose per liter) with oat extract (10%) and DMSO (0.5%). The inoculation was carried out using a concentrated spore suspension of *Fusarium graminearum* at a final concentration of 2000 spores/ml.

The plate was incubated at high atmospheric humidity at 28° C. for 7 days.

At the beginning and after 3 days, an OD measurement was carried out at OD620 (repeated measurements: 3×3 measurements per well) to calculate the inhibition of growth.

After 7 days, 1 volume of a 84/16 acetonitrile/water mixture was added, and samples of the liquid medium from each of the wells were then removed and diluted 1:100 with 10% strength acetonitrile. The proportions of DON and acetyl-DON of the samples were analyzed by HPLC-MS/MS, and the measured values were used to calculate the inhibition of the DON/AcDON production compared to an active compound-free control.

Examples of the Inhibition of DON/AcDON Production:

In this test, the exemplary compounds according to the invention Nos. 1, 3, 5, 6, 16 and 41 of Tables 1 and 2 show, at a concentration of 50 μM, an activity of >70% in the inhibition of DON/AcDON production. The inhibition of the growth of *Fusarium graminearum* of the examples mentioned below varied from 56 to 100% at 50 μM.

Example 4

*Phytophthora* Test (Tomato)/Protective

Solvent: 49 parts by weight of N,N-dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. One day after the treatment, the plants are inoculated with a spore suspension of *Phytophthora infestans* and then remain at 100% relative humidity and 22° C. for 24 h. The plants are then placed in a climatized cell at about 96% relative atmospheric humidity and a temperature of about 20° C.

Evaluation is carried out 7 days after the inoculation. 0% means an efficacy which corresponds to that of the control, whereas an efficacy of 100% means that no infection is observed.

In this test, the exemplary compounds according to the invention Nos. 3, 6, 13, 14, 15, 22, 23, 25, 29, 32, 33, 34, 35, 36, 68, 71 and 72 of Tables 1 and 2 show, at an active compound concentration of 500 ppm, an efficacy of 70% or more Example 5

*Botrytis* Test (Bean)/Protective

Solvents: 24.5 parts by weight of acetone 24.5 parts by weight of dimethylacetamide Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, 2 small pieces of agar colonized by *Botrytis cinerea* are placed onto each leaf. The inoculated plants are placed in a dark chamber at about 20° C. and 100% relative atmospheric humidity.

Two days after the inoculation, the size of the infected areas on the leaves is evaluated. 0% means an efficacy which corresponds to that of the control, whereas an efficacy of 100% means that no infection is observed.

In this test, the exemplary compounds according to the invention Nos. 6, 14, 16, 17, 22, 24, 26, 28, 31, 32, 33, 36, 42, 43, 44, 51, 56, 76 and 103 of Tables 1 and 2 show, at an active compound concentration of 250 ppm, an efficacy of 70% or more.

Example 6

*Leptosphaeria nodorum* Test (Wheat)/Protective

Solvent: 49 parts by weight of N,N-dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young wheat plants are sprayed with the preparation of active compound at the stated application rate. One day after the treatment, the plants are inoculated with an aqueous spore suspension of *Leptosphaeria nodorum* and then remain at 100% relative atmospheric humidity and 22° C. for 48 h. The plants are then placed in a greenhouse at 90% relative atmospheric humidity and a temperature of 22° C.

Evaluation is carried out 7-9 days after the inoculation. 0% means an efficacy which corresponds to that of the control, whereas an efficacy of 100% means that no infection is observed.

In this test, the exemplary compounds according to the invention Nos. 17, 20, 26, 27, 28, 31, 32, 33, 34, 42, 43, 45, 48, 51, 56, 57, 76 and 79 of Tables 1 and 2 show, at an active compound concentration of 500 ppm, an efficacy of 70% or more.

Example 7

*Pyrenophora teres* Test (Barley)/Protective

Solvent: 49 parts by weight of N,N-dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young barley plants are sprayed with the preparation of active compound at the stated application rate. One day after the treatment, the plants are inoculated with an aqueous spore suspension of *Pyrenophora teres* and then remain at 100% relative atmospheric humidity and 22° C. for 48 h. The plants are then placed in a greenhouse at 80% relative atmospheric humidity and a temperature of 20° C.

Evaluation is carried out 7-9 days after the inoculation. 0% means an efficacy which corresponds to that of the control, whereas an efficacy of 100% means that no infection is observed.

In this test, the exemplary compounds according to the invention Nos. 3, 6, 16, 17, 19, 21, 24, 26, 27, 28, 30, 31, 32, 33, 35, 36, 37, 41, 42, 43, 44, 45, 48, 51, 53, 56, 57, 76, 78, 79 and 103 of Tables 1 and 2 show, at an active compound concentration of 500 ppm, an efficacy of 70% or more.

Example 8

*Septoria tritici* Test (Wheat)/Protective

Solvent: 50 parts by weight of N,N-dimethylacetamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a spore suspension of *Septoria tritici*. The plants remain in an incubation cabin at 20° C. and 100% relative atmospheric humidity for 48 hours. The plants are then placed under a translucent hood at 15° C. and 100% relative atmospheric humidity for a further 60 hours.

The plants are placed in a greenhouse at a temperature of about 15° C. and a relative atmospheric humidity of 80%.

Evaluation is carried out 21 days after the inoculation. 0% means an efficacy which corresponds to that of the control, whereas an efficacy of 100% means that no infection is observed.

In this test, the exemplary compounds according to the invention Nos. 26, 28, 31, 32, 33, 42, 43, 44, 45, 51 and 57 of Tables 1 and 2 show, at an active compound concentration of 500 ppm, an efficacy of 70% or more.

Example 9

*Alternaria* Test (Tomato)/Protective

Solvent: 49 parts by weight of N,N-dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. One day after the treatment, the plants are inoculated with a spore suspension of *Alternaria solani* and then remain at 100% relative humidity and 22° C. for 24 h. The plants then remain at 96% relative atmospheric humidity and a temperature of 20° C.

Evaluation is carried out 7 days after the inoculation. 0% means an efficacy which corresponds to that of the control, whereas an efficacy of 100% means that no infection is observed.

In this test, the Examples Nos. 2, 3, 6 and 9 of Table I show, at an active compound concentration of 500 ppm, an efficacy of 70% or more.

Example 10

Fumonisin FB1 Production by *Fusarium verticillioides*

The method of Lopez-Errasquin et al. (2007) Journal of Microbiological Methods 68, 312-317 was adapted for 96-well microtitre plates:

Fumonisin-inducing liquid medium (Jiménez et al. (2003) Int. J. Food Microbiol. 89, 185-193) was inoculated with a concentrated *Fusarium verticillioides* spore suspension of 350 000 spores/ml (stored at −160° C.). This gave a final concentration of 2000 spores/ml in the so-called inoculation medium.

The exemplary compounds were made up as a 10 mM stock solution in 100% DMSO and diluted with $H_2O$ to 1 mM. The substances were tested at a final concentration of 50 µM.

In a well of a 96-well microtitre plate, 5 µl of the 1 mM substance solution were mixed with 95 µl of inoculation medium. The plate was then closed with a lid and incubated at 20° C. for 6 days. A sample comprising 5 µl of the solvent of the substance solution and 95 µl of the inoculation medium served as a positive control.

At the beginning of the experiment and after 6 days, optical density measurements were carried out at $OD_{620}$ (3×3 measurements per well) to calculate the inhibition of growth in percent.

After 6 days, a sample of the liquid medium was removed and diluted with 10% acetonitrile (v/v). The samples were appropriately diluted with acetonitrile to determine the fumonisin FB1 concentrations by HPLC-MS/MS. The results were used to calculate the inhibition of mycotoxin biosynthesis in percent. 0% means an efficacy which corresponds to the fumonisin FB1 content of the positive control, whereas an efficacy of 100% means that the fumonisin FB1 concentration of the sample after dilution was below the analytical detection threshold of 0.1 ng/ml. The dynamic difference between positive control and sample detection limit was at least a factor of 200.

In this test, the Examples Nos. 1, 2, 3, 4, 5, 6, 7, 8, 9, 10 and 11 of Table I show, at an active compound concentration of 50 µM, an efficacy of 70% or more.

Example 11

DON/Acetyl-DON Production by *Fusarium graminearum*

The method is based on the method described by McCormick et al. (2004) Appl. Environmental Microbiology 70: 2044-2051, adapted to microtitre plates:

10% (w/v) oats extract dissolved in $H_2O$ was added to DON-inducing liquid medium (production medium—modified MYRO), and the medium was inoculated with a concentrated *Fusarium graminearum* spore suspension of 200 000 spores/ml (at −160° C.). This gave a final concentration of 2000 spores/ml in the so-called inoculation medium The substances were made up as a 10 mM stock solution in 100% DMSO and diluted with $H_2O$ to 1 mM. The substances were tested at a final concentration of 50 µM.

In a well of a 96-well microtitre plate, 5 µl of the 1 mM substance solution were mixed with 95 µl of inoculation medium. The plate was then closed with a lid and incubated at 28° C. for 7 days. A sample comprising 5 µl of the solvent of the substance solution and 95 µl of the inoculation medium served as positive control.

At the beginning of the experiment and after 3 days, optical density measurements were carried out at $OD_{620}$ (3×3 measurements per well) to calculate the inhibition of growth in percent.

After 7 days, 100 µl of acetonitrile:$H_2O$ in a ratio of 84:16 (v/v) were added to each cavity, and the mixture was incubated at room temperature for 30 minutes. 5 µl of sample were then removed and diluted with 10% (v/v) acetonitrile such that the DON and acetyl-DON concentrations could be determined by HPLC-MS/MS. The DON and acetyl-DON concentrations of the diluted samples were analyzed by HPLC-MS/MS and the results were used to calculate the inhibition of mycotoxin biosynthesis in percent. 0% means an efficacy which corresponds that of the positive control, whereas an efficacy of 100% means that the mycotoxin concentration of the sample after dilution was below the analytical detection threshold of 0.1 ng/ml. The dynamic difference between positive control and sample detection limit was at least a factor of 200. Both Don and Ac-Don were measured. For evaluation, both mycotoxin values were added and assessed together.

In this test, the Examples Nos. 3 and 5 of Table I show, at an active compound concentration of 50 μM, an efficacy of 70% or more.

The invention claimed is:

1. A method for controlling phytopathogenic fungi and for reducing mycotoxins in plants and parts of plants comprising contacting one or more 5-pyridin-4-yl-1,3-thiazoles of formula (I)

(I)

or an agrochemically active salt thereof,
in which
$R^1$ represents hydrogen, represents an optionally hydroxyl-, amino-, cyano-, $C_1$-$C_4$-alkoxy-, $R^5$-, $OR^5$-, ($C_1$-$C_4$-alkyl)sulphanyl-, ($C_1$-$C_4$-alkyl)sulphinyl-, ($C_1$-$C_4$-alkyl)sulphonyl-, ($C_1$-$C_4$-alkyl)amino-, bis($C_1$-$C_4$-alkyl)amino-, $C_1$-$C_4$-alkylcarbonyloxy-or $OCOR^5$-substituted $C_1$-$C_8$-alkyl, $C_1$-$C_6$-haloalkyl, represents an optionally $C_1$-$C_4$-alkyl- or halogen-substituted $C_3$-$C_8$-cycloalkyl, represents $COR^6$, $COOR^6$, $CON(R^6)_2$, $(CH_2)_mOR^6$, $(CH_2)_mSR^6$, $(CH_2)_mSOR^6$, $(CH_2)_mSO_2R^6$, $(CH_2)_mSON(R^6)_2$, $(CH_2)_mSO_2N(R^6)_2$, $(CH_2)_mN(R^6)_2$, $(CH_2)_mNR^6COR^6$, $(CH_2)_mCOOR^6$, $(CH_2)_mCON(R^6)_2$, $(CH_2)_mCOR^6$, or $(CH_2)_mC(NOR^6)R^6$, represents $N(R^6)_2$, $NR^6(CH_2)_mCOOR^6$, $N=CR^6N(R^6)_2$, $NR^6COR^6$, $NR^6CO(CH_2)_mOR^6$, $NR^6COCH(C_1$-$C_4$-alkyl)$OR^6$, $NR^6CO(CH_2)_mN(R^6)_2$, $NR^6CO(CH_2)_mCOOR^6$, $NR^6COOR^7$, $NR^6CON(R^6)_2$, $NR^6CO(CH_2)_mR^8$, or $NR^6(CH_2)_mR^8$,
or
$R^1$ represents a phenyl radical which is optionally mono- or polysubstituted by identical or different radicals selected from the group consisting of $C_1$-$C_4$-alkyl, halogen, cyano, $C_1$-$C_4$-haloalkyl, $OR^6$, $N(R^6)_2$, $SR^6$, $SOR^6$, $S(O)_2R^6$, $SO_2N(R^6)_2$, $COOR^6$, $COR^6$, $C(NOR^6)R^6$, $(CH_2)_mOR^6$, $CON(R^6)_2$, and $CH=CR^6COOR^6$,
$R^2$ represents an aryl radical which is optionally mono- or polysubstituted by identical or different radicals selected from the group consisting of halogen, cyano, hydroxyl, $SF_6$, nitro, $C_1$-$C_6$-alkyl, $C_3$-$C_8$-cycloalkyl, $C_1$-$C_4$-haloalkyl, $C_2$-$C_6$-alkenyl, $C_2$-$C_6$-alkynyl, $OR^6$, ($C_1$-$C_4$)alkoxy($C_1$-$C_4$)alkyl, ($C_1$-$C_2$)alkanediylbisoxy, ($C_1$-$C_2$)haloalkanediylbisoxy, $C_3$-$C_5$-alkanediyl, $N(R^6)_2$, $SR^6$, $COOR^6$, $COR^6$, $C(R^6)NOR^6$, $CON(R^6)_2$, $CH=CR^6COOR^6$, $O(CH_2)_mCOOR^6$, $NR^6COR^6$, $NR^6CON(R^6)_2$, $NR^6COO(R^7)$ and optionally halogen-, $C_1$-$C_4$-alkyl-, or $C_1$-$C_4$-alkoxy-substituted phenyl,
or
$R^2$ represents a five- or six-membered heteroaromatic which contains up to four heteroatoms selected from the group consisting of N, O and S, where two oxygen atoms are not adjacent, and which is optionally mono- or polysubstituted by identical or different radicals selected from the group consisting of halogen, cyano, $C_1$-$C_4$-alkyl, $C_1$-$C_4$-alkoxy, $C_1$-$C_4$-haloalkyl, phenyl and $C_3$-$C_8$-cycloalkyl;
$R^3$ represents hydrogen, cyano, hydroxyl, $OR^6$, cyano, amino, $C_1$-$C_6$-alkyl, $C_1$-$C_8$-haloalkyl, $(CH_2)_mOR^6$, $(CH_2)_mCN$, $(CH_2)_mN(R^6)_2$, $COOR^6$, $CON(R^6)_2$, $SR^6$, $SOR^6$, $S(O)_2R^6$, $NR^6COR^6$, $NR^6COOR^7$, $NR^6CON(R^6)_2$, $NR^6SO_2R^6$, $N=S(O)(R^6)_2$; $N=CR^6N(R^6)_2$, $NR^6CO(CH_2)_mR^9$ or $NR^6(CH_2)_mR^9$;
or
$R^3$ represents a heterocycle selected from the group consisting of pyrrolidine, piperidine, piperazine, and morpholine, each of which is unsubstituted or optionally substituted by oxo, halogen, or ($C_1$-$C_4$)alkyl;
$R^4$ represents hydrogen or $C_1$-$C_4$-alkyl;
$R^5$ represents a phenyl radical which is optionally substituted by halogen, hydroxyl, cyano, $C_1$-$C_4$-alkyl, $C_1$-$C_4$-alkoxy, $C_1$-$C_2$-haloalkoxy, $C_1$-$C_2$-haloalkyl, $C_1$-$C_4$-alkoxycarbonyl, or carboxyl;
$R^6$ independently of one another represent hydrogen, $C_1$-$C_6$-alkyl, optionally $C_1$-$C_4$-alkyl- or halogen-substituted $C_3$-$C_6$-cycloalkyl, $C_1$-$C_6$-haloalkyl, $C_2$-$C_6$-alkenyl, $C_2$-$C_6$-alkynyl, $C_1$-$C_4$-alkoxy($C_1$-$C_4$)alkyl, hydroxy($C_1$-$C_4$)alkyl,
represents aryl or aryl($C_1$-$C_4$)alkyl, each of which is optionally mono- or polysubstituted by identical or different radicals selected from the group consisting of halogen, cyano, hydroxyl, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylcarbonyl, carboxyl and $C_1$-$C_4$-alkoxycarbonyl,
or
represents a 3- to 7-membered saturated or unsaturated cycle which contains no or up to four heteroatoms selected from the group consisting of N, O and S, where two oxygen atoms are not adjacent, and which is unsubstituted or optionally mono- or polysubstituted by identical or different radicals selected from the group consisting of halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylcarbonyl and $C_1$-$C_4$-alkoxycarbonyl,
or
if two radicals $R^6$ are attached to a nitrogen atom, two radicals $R^6$ form a 3- to 7-membered saturated or unsaturated cycle which contains up to four further heteroatoms selected from the group consisting of N, O and S, where two oxygen atoms are not adjacent, and which is unsubstituted or optionally mono- or polysubstituted by identical or different radicals selected from the group consisting of halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylcarbonyl and $C_1$-$C_4$-alkoxycarbonyl,
or
if two radicals $R^6$ are present in adjacent positions in the grouping $NR^6COR^6$, two radicals $R^6$ form a 3- to 7-membered saturated or unsaturated cycle which contains up to four further heteroatoms selected from the group consisting of N, O and S, where two oxygen atoms are not adjacent, and which is unsubstituted or optionally mono- or polysubstituted by identical or different radicals selected from the group consisting of halogen, hydroxyl, $C_1$-$C_4$-alkyl, $C_1$-$C_4$-haloalkyl, $C_1$-$C_4$-alkoxy, $C_1$-$C_4$-haloalkoxy and phenyl,
or
if two radicals $R^6$ are attached to a sulphur atom, two radicals $R^6$ form a 5- to 7-membered cycle which contains up to two further heteroatoms selected from the group consisting of N, O and S, where two oxygen atoms are not adjacent, and which is unsubstituted or optionally $C_1$-$C_4$-alkyl-substituted;

$R^7$ independently of one another represent $C_1$-$C_6$-alkyl, optionally $C_1$-$C_4$-alkyl- or halogen-substituted $C_3$-$C_6$-cycloalkyl, $C_1$-$C_6$-haloalkyl, $C_2$-$C_6$-alkenyl, $C_2$-$C_6$-alkynyl, $C_1$-$C_4$-alkoxy($C_1$-$C_4$)alkyl, hydroxy($C_1$-$C_4$)alkyl, represent aryl or aryl($C_1$-$C_4$)alkyl, each of which is optionally mono- or polysubstituted by identical or different radicals selected from the group consisting of halogen, cyano, hydroxyl, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylcarbonyl, carboxyl and $C_1$-$C_4$-alkoxycarbonyl, or represent a 3- to 7-membered saturated or unsaturated cycle which contains no or up to four heteroatoms selected from the group consisting of N, O and S, where two oxygen atoms are not adjacent, and which is unsubstituted or optionally mono- or polysubstituted by identical or different radicals selected from the group consisting of halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylcarbonyl and $C_1$-$C_4$-alkoxycarbonyl;

$R^8$ represents a 3- to 7-membered saturated, unsaturated or aromatic mono- or bicycle which contains no or up to four heteroatoms selected from the group consisting of N, O and S, where two oxygen atoms are not adjacent, and which is optionally substituted by oxo, hydroxyl, halogen, cyano, $C_1$-$C_4$-alkyl, $C_1$-$C_4$-haloalkyl, $C_1$-$C_4$-alkoxy, haloalkoxy, phenyl, carboxyl, $C_1$-$C_6$-alkylcarbonyl or $C_1$-$C_6$-alkoxycarbonyl;

$R^9$ represents a 3- to 7-membered saturated, unsaturated or aromatic mono- or bicycle which contains no or up to four heteroatoms selected from the group consisting of N, O and S, where two oxygen atoms are not adjacent, and which is unsubstituted or optionally mono- or polysubstituted by identical or different radicals selected from the group consisting of $C_1$-$C_4$-alkyl, halogen, cyano, $C_1$-$C_4$-haloalkyl and $C_1$-$C_4$-alkoxy;

m represents a number from 1 to 6;

with the fungi, their habitat or both.

2. The method according to claim 1, wherein $R^1$ represents hydrogen, $C_1$-$C_6$-alkyl, $C_1$-$C_4$-haloalkyl, $C_3$-$C_8$-cycloalkyl, aryl($C_1$-$C_4$)alkyl, formyl, ($C_1$-$C_4$-alkyl)carbonyl, ($C_1$-$C_4$-haloalkyl)carbonyl, COOH, ($C_1$-$C_4$-alkoxy)carbonyl, ($C_3$-$C_6$-alkenyloxy)carbonyl, ($C_3$-$C_6$-alkynyloxy)carbonyl, ($C_1$-$C_4$-alkyl)carbamoyl, bis($C_1$-$C_4$-alkyl)carbamoyl, ($C_3$-$C_4$-alkenyl)carbamoyl, ($C_3$-$C_4$-alkynyl)carbamoyl, $CONHR^{10}$, $C_1$-$C_6$-hydroxyalkyl, $C_1$-$C_4$-alkoxy($C_1$-$C_4$)alkyl, phenyloxy($C_1$-$C_4$)alkyl, ($C_1$-$C_4$-alkyl)carbonyloxy($C_1$-$C_4$)alkyl, phenylcarbonyloxy($C_1$-$C_4$)alkyl, ($C_1$-$C_4$-alkyl)sulphanyl($C_1$-$C_4$)alkyl, amino($C_1$-$C_4$)alkyl, ($C_1$-$C_4$-alkyl)amino($C_1$-$C_4$)alkyl, bis($C_1$-$C_4$-alkyl)amino($C_1$-$C_4$)alkyl, piperidin-1-ylethyl, morpholin-1-ylethyl, phenylcarbonylamino($C_1$-$C_4$)alkyl, ($C_1$-$C_4$-alkyl)carbonylamino($C_1$-$C_4$)alkyl, $(CH_2)_m N(C_1$-$C_2$-alkyl)CO($C_1$-$C_4$-alkyl), $(CH_2)_m COOH$, $(CH_2)_m COO(C_1$-$C_4$)alkyl, $(CH_2)_m COO(C_3$-$C_5$)alkenyl, $(CH_2)_m COO(C_3$-$C_5$)alkynyl, $(CH_2)_m CONH(C_1$-$C_4$)alkyl, $(CH_2)_m CON((C_1$-$C_4$)alkyl)_2$, $(CH_2)_m NHCOR^{10}$, $(CH_2)_m OCOR^{10}$, $(CH_2)_m R^{10}$, amino, $NH(C_1$-$C_4$-alkyl), $N(C_1$-$C_4$-alkyl)_2$, $NH(C_3$-$C_5$-alkenyl), $NH(C_3$-$C_5$-alkynyl), $NH(C_3$-$C_6$-cycloalkyl), $NHR^{10}$, $NH(R^{11})$, $NH(CH_2)_m R^{10}$, $N=CHN(C_1$-$C_4$-alkyl)_2$ $N=C(C_1$-$C_2$-alkyl)N(C_1$-$C_4$-alkyl)_2$, $NH(CH_2)_m COO(C_1$-$C_4$-alkyl), NHCO($C_1$-$C_4$-alkyl), $NHCO(C_2$-$C_5$-alkenyl), $N(C_1$-$C_5$-alkyl)CO(C_1$-$C_4$-alkyl), $N(C_3$-$C_5$-alkenyl)CO(C_1$-$C_4$-alkyl), $N(C_3$-$C_5$-alkynyl)CO(C_1$-$C_4$-alkyl),)N($R^{10}$)CO($C_1$-$C_4$-alkyl), N(Bn)CO($C_1$-$C_4$-alkyl), $NHCO(C_3$-$C_6$-cycloalkyl), $NHCOCH_2(C_3$-$C_6$-cycloalkyl), $NHCO(C_1$-$C_5$-haloalkyl), $NHCO(C_1$-$C_4$-alkoxy), $NHCO(C_1$-$C_4$-haloalkoxy), $NHCO(CH_2)_m COO(C_1$-$C_4$-alkyl), $NHCOCH_2OH$, $NHCOCH_2OMe$, $NHCOCH(Me)OH$, $NHCOCH_2NMe_2$, $NHCO(CH_2)_m R^{10}$, $NHCOR^{10}$, $N(C_1$-$C_4$-alkyl)COR^{10}$, $N(C_3$-$C_5$-alkenyl)CO(R^{10})$, $N(C_3$-$C_5$-alkynyl)CO(R^{10})$, $NHCONH(C_1$-$C_4$alkyl), $NHCON(C_1$-$C_4$alkyl)_2$, $NHCONHR^{10}$, $NHCO(R^{11})$, or $N(C_1$-$C_4$-alkyl)CO(R^{11})$, or $R^1$ represents a phenyl radical which is optionally mono- or polysubstituted by identical or different radicals selected from the group consisting of halogen, cyano, hydroxyl, $C_1$-$C_4$-alkyl, $C_1$-$C_4$-alkoxy, $C_1$-$C_4$-haloalkoxy, $C_1$-$C_4$-haloalkyl, $C_1$-$C_4$-alkylsulphonyl, $C_1$-$C_4$-alkylsulphinyl, $C_1$-$C_4$-alkylsulphanyl, $C_1$-$C_4$-alkylcarbonyl, $C_1$-$C_4$-alkoxycarbonyl, carboxyl, carbamoyl, $C_1$-$C_4$-alkylcarbamoyl, bis($C_1$-$C_4$-alkyl)carbamoyl and ($C_3$-$C_4$)-alkenylcarbamoyl, $R^2$ represents a phenyl or naphthalenyl radical, each of which is optionally mono- or polysubstituted by identical or different radicals selected from the group consisting of halogen, cyano, hydroxyl, $C_1$-$C_6$-alkyl, $C_3$-$C_6$-cycloalkyl, $C_1$-$C_4$-alkoxy, ($C_1$-$C_4$)alkoxy($C_1$-$C_4$)alkyl, benzyloxy, $C_1$-$C_4$-haloalkyl, $C_1$-$C_4$-haloalkoxy, methanediylbisoxy, difluoromethanediylbisoxy, propane-1,3-diyl, $NH(C_1$-$C_4$-alkyl), $N(C_1$-$C_4$-alkyl)_2$, ($C_1$-$C_4$)alkylsulphanyl, ($C_1$-$C_4$)alkoxycarbonyl, and carboxyl, or represents a heteroaromatic selected from the group consisting of furan, thiophene, and pyridine, each of which is unsubstituted or optionally substituted by fluorine, chlorine, or $C_1$-$C_4$-alkyl;

$R^3$ represents hydrogen, hydroxyl, amino, cyano, ($C_1$-$C_4$)alkyl, ($C_1$-$C_4$)haloalkyl, ($C_1$-$C_4$)alkoxy, hydroxymethyl, cyanomethyl, pyrrolidin-1-ylmethyl, phenylsulphanyl, benzylsulphanyl, phenylsulphonyl, ($C_1$-$C_4$)alkoxycarbonyl, ($C_1$-$C_4$)alkylcarbamoyl, bis($C_1$-$C_4$)alkylcarbamoyl, $NH(C_1$-$C_4$-alkyl), $N(C_1$-$C_4$-alkyl)_2$, $NH(C_1$-$C_4$-haloalkyl), ($C_1$-$C_4$)alkoxy($C_1$-$C_4$)alkylamino, hydroxy($C_1$-$C_4$)alkylamino, $NH(C_3$-$C_5$-alkenyl), $NH(C_3$-$C_5$-alkynyl), $NH(C_3$-$C_6$-cycloalkyl), $N(C_1$-$C_4$-alkyl)(C_3$-$C_6$-cycloalkyl), $NHCO(C_1$-$C_6$-alkyl), $N(C_1$-$C_4$-alkyl)CO(C_1$-$C_6$-alkyl), $N(C_3$-$C_4$-alkenyl)CO(C_1$-$C_6$-alkyl), $N(C_3$-$C_4$-alkynyl)CO(C_1$-$C_6$-alkyl), $NHCO(C_1$-$C_6$-haloalkyl), $N(C_1$-$C_4$-alkyl)CO(C_1$-$C_6$-haloalkyl), $N(C_3$-$C_4$-alkenyl)CO(C_1$-$C_6$-haloalkyl), $N(C_3$-$C_4$-alkynyl)CO(C_1$-$C_6$-haloalkyl), $NHCO(C_3$-$C_6$-cycloalkyl), $N(C_1$-$C_4$-alkyl)CO(C_3$-$C_6$-cycloalkyl), $N(C_3$-$C_4$-alkenyl)CO(C_3$-$C_6$-cycloalkyl), $N(C_3$-$C_4$-alkynyl)CO(C_3$-$C_6$-cycloalkyl), (2-methylcyclopropyl)carbonylamino, (1-methylcyclohexyl)carbonylamino, $NHCO(C_2$-$C_4$-alkenyl), $NHCOR^{12}$, $N(C_1$-$C_4$-alkyl)CO(R^{12})$, $N(C_3$-$C_4$-alkenyl)CO(R^{12})$, $N(C_3$-$C_4$-alkynyl)CO(R^{12})$, $NHCO(CH_2)_m R^{12}$, $NMeCO(CH_2)_m R^{12}$, $NH(CH_2)_m R^{12}$, $NMe(CH_2)_m R^{12}$, $NHCO(CH_2)_m (C_3$-$C_6$-cycloalkyl), $NH(CH_2)_m (C_3$-$C_6$-cycloalkyl), $NHCOO(C_1$-$C_4$-alkyl), $NHCOO(C_1$-$C_4$-haloalkyl), $NHCONH(C_1$-$C_4$-alkyl), $NHCH(Me)R^{12}$, (thiophen-2-ylcarbonyl)amino, (thiophen-2-ylmethyl)amino, ($C_1$-$C_4$-alkyl)sulphonylamino, or ($C_3$-$C_6$-cycloalkyl)sulphonylamino, or $R^3$ represents a heterocycle selected from the group consisting of pyrrolidine, piperidine, piperazine, and morpholine, each of which is unsubstituted or optionally substituted by oxo, halogen, or $(C_1-C_4)$alkyl;

$R^4$ represents hydrogen or methyl;

$R^{10}$ represents a phenyl radical which is optionally substituted by halogen, hydroxyl, cyano, $C_1-C_4$-alkyl, $C_1-C_4$-alkoxy, $C_1-C_2$-haloalkoxy, $C_1-C_2$-haloalkyl, alkoxycarbonyl, or carboxyl;

$R^{11}$ represents a heteroaromatic selected from the group consisting of furan, thiophene, pyridine, and pyrazine which is optionally substituted by fluorine, chlorine, cyano, $C_1-C_4$-alkyl, $C_1-C_4$-alkoxy, $C_1-C_2$-haloalkyl, or $C_1-C_4$-alkoxycarbonyl;

$R^{12}$ represents a phenyl- or naphthalenyl radical which is optionally substituted by halogen, $(C_1-C_4)$alkyl $(C_1-C_4)$ alkoxy, or $(C_1-C_4)$haloalkyl;

and m represents a number from 1 to 6.

3. The method according to claim 1, wherein $R^1$ represents hydrogen, $C_1-C_6$-alkyl, $C_1-C_2$-haloalkyl, $C_3-C_6$-cycloalkyl, aryl$(C_1-C_4)$alkyl, formyl, $(C_1-C_4$-alkyl)carbonyl, $(C_1-C_2$-haloalkyl)carbonyl, COOH, $(C_1-C_4$-alkoxy)carbonyl, $(C_3-C_4$-alkenyloxy)carbonyl, $(C_3-C_4$-alkynyloxy)carbonyl, $C_1-C_6$-hydroxyalkyl, $C_1-C_4$-alkoxy$(C_1-C_4)$alkyl, phenoxy$(C_1-C_4)$alkyl, $(C_1-C_4$-alkyl)carbonyloxy$(C_1-C_2)$alkyl, phenylcarbonyloxy$(C_1-C_2)$alkyl, $(C_1-C_2$-alkyl)sulphanyl$(C_1-C_2)$alkyl, amino$(C_1-C_2)$alkyl, $(C_1-C_4$-alkyl)amino$(C_1-C_2)$alkyl, bis$(C_1-C_4$-alkyl)amino$(C_1-C_2)$alkyl, piperidin-1-ylethyl, morpholin-1-ylethyl, phenylcarbonylamino$(C_1-C_2)$alkyl, $(C_1-C_4$-alkyl)carbonylamino$(C_1-C_2)$alkyl, $(CH_2)_m$NMeCO$(C_1-C_4$-alkyl), $(CH_2)_m$COOH, $(CH_2)_m$COO$(C_1-C_4$-alkyl), $(CH_2)_m$COO$(C_3-C_4$-alkenyl), $(CH_2)_m$COO$(C_3-C_4$-alkynyl), $(CH_2)_m$CONH$(C_1-C_4)$alkyl, $(CH_2)_m$CON$((C_1-C_4)$alkyl$)_2$, amino, NH$(C_1-C_4$-alkyl), N$(C_1-C_4$-alkyl$)_2$, NH$(C_3-C_4$-alkenyl), NH$(C_3-C_4$-alkynyl), NH$(C_3-C_6$-cycloalkyl), NHR$^{10}$, NH$(CH_2)_m$R$^{10}$, NH$(R^{11})$, N=CHN$(C_1-C_4$-alkyl$)_2$, N=C$(C_1-C_2$-alkyl)N$(C_1-C_4$-alkyl$)_2$, NH$(CH_2)_m$COO$(C_1-C_4$-alkyl), NHCO$(C_1-C_4$-alkyl), NHCO$(C_2-C_4$-alkenyl), N$(C_1-C_5$-alkyl)CO$(C_1-C_4$-alkyl), N(Ph)CO$(C_1-C_4$-alkyl), N(Bn)CO$(C_1-C_4$-alkyl), NHCO$(C_3-C_6$-cycloalkyl), NHCOCH$_2(C_3-C_6$-cycloalkyl), NHCO$(C_1-C_5$-haloalkyl), NHCO$(C_1-C_4$-alkoxy), NHCO$(C_1-C_4$-haloalkoxy), NHCO$(CH_2)_m$COO$(C_1-C_4$-alkyl), NHCOCH$_2$OH, NHCOCH$_2$OMe, NHCOCH(Me)OH, NHCOCH$_2$NMe$_2$, NHCO$(CH_2)_m$R$^{10}$, NHCOR$^{10}$, N$(C_1-C_4$-alkyl)COR$^{10}$, NHCONH$(C_1-C_4$-alkyl), NHCON$(C_1-C_4$-alkyl$)_2$, NHCONHR$^{10}$, or NHCO$(R^{11})$, or $R^1$ represents a phenyl radical which is optionally mono- or polysubstituted by identical or different radicals selected from the group consisting of fluorine, chlorine, bromine, hydroxyl, $C_1-C_4$-alkyl, $C_1-C_4$-alkoxy, $C_1-C_2$-haloalkoxy, $C_1-C_2$-haloalkyl, $C_1-C_2$-alkylsulphonyl, $C_1-C_2$-alkylsulphinyl, $C_1-C_2$-alkylsulphanyl, $C_1-C_4$-alkoxycarbonyl, carboxyl, carbamoyl, $C_1-C_4$-alkylcarbamoyl, bis$(C_1-C_4$-alkyl)carbamoyl and $(C_3-C_4)$-alkenylcarbamoyl, $R^2$ represents a phenyl or naphthalenyl radical, each of which is optionally mono- or polysubstituted by identical or different radicals selected from the group consisting of halogen, cyano, hydroxyl, $C_1-C_6$-alkyl, $C_3-C_6$-cycloalkyl, $C_1-C_4$-alkoxy, benzyloxy, $C_1-C_4$-haloalkyl, $C_1-C_4$-haloalkoxy, methanediylbisoxy, difluoromethanediylbisoxy, propane-1,3-diyl, NH$(C_1-C_4$-alkyl), N$(C_1-C_4$-alkyl$)_2$, $(C_1-C_4)$alkylsulphanyl, $(C_1-C_4)$alkoxycarbonyl, and carboxyl, or $R^2$ represents a heteroaromatic selected from the group consisting of furan, thiophene, and pyridine, each of which is unsubstituted or optionally substituted by fluorine, chlorine, or $C_1-C_4$-alkyl;

$R^3$ represents hydrogen, hydroxyl, amino, cyano, $(C_1-C_2)$ alkyl, $(C_1-C_2)$haloalkyl, $(C_1-C_2)$alkoxy, hydroxymethyl, cyanomethyl, pyrrolidin-1-ylmethyl, phenylsulphanyl, benzylsulphanyl, phenylsulphonyl, $(C_1-C_4)$ alkoxycarbonyl, NH$(C_1-C_4$-alkyl), N$(C_1-C_4$-alkyl$)_2$, $(C_1-C_2)$alkoxy$(C_1-C_4)$alkylamino, NH$(C_3-C_4$-alkenyl), NH$(C_3-C_4$-alkynyl), NH$(C_3-C_6$-cycloalkyl), N(Me)$(C_3-C_6$-cycloalkyl), NHCO$(C_1-C_6$-alkyl), NHCO$(C_3-C_6$-cycloalkyl), (1-methylcyclohexyl)carbonylamino, NHCOR$^{12}$, NMeCOR$^{12}$, NHCO$(CH_2)_m$R$^{15}$, NMeCO$(CH_2)_m$R$^{12}$, NH$(CH_2)_m$R$^{12}$, NMe$(CH_2)_m$R$^{12}$, NHCO$(CH_2)_m(C_3-C_6$-cycloalkyl), NH$(CH_2)_m(C_3-C_6$-cycloalkyl), NHCOO$(C_1-C_4$-alkyl), NHCONH$(C_1-C_4$-alkyl), NHCH(Me)R$^{12}$, (thiophen-2-ylcarbonyl)amino, or (thiophen-2-ylmethyl)amino, or $R^3$ represents a heterocycle selected from the group consisting of pyrrolidine, piperidine, piperazine, and morpholine, each of which is unsubstituted or optionally substituted by methyl;

$R^4$ represents hydrogen, methyl;

$R^{10}$ represents a phenyl radical which is optionally substituted by fluorine, chlorine, hydroxyl, cyano, $C_1-C_4$-alkyl, $C_1-C_4$-alkoxy, $C_1-C_2$-haloalkoxy, $C_1-C_2$-haloalkyl, $C_1-C_4$-alkoxycarbonyl, or carboxyl;

$R^{11}$ represents a heteroaromatic selected from the group consisting of furan, thiophene, pyridine, and pyrazine, each of which is optionally substituted by chlorine, methyl, or methoxy;

$R^{12}$ represents a phenyl- or naphthalenyl radical which is optionally substituted by fluorine, chlorine, methyl, methoxy, or trifluoromethyl;

and m represents a number from 1 to 4.

4. The method according to claim 1, wherein $R^1$ represents hydrogen, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, cyclopropyl, cyclobutyl, cyclopentyl, cyclohexyl, $CF_3$, $CHF_2$, $CH_2CF_3$, $CF_2CH_3$, benzyl, 2-phenylethyl, 1-phenylethyl, 3-phenylpropyl, formyl, acetyl, propanoyl, 2-methylpropanoyl, trifluoroacetyl, COOH, COOMe, COOEt, COOiPr, COOPr, COOCH$_2$CH=CH$_2$, COOCH$_2$CCH, CHMeOH, CMe$_2$OH CH$_2$OH, CH$_2$OMe, CH$_2$OEt, CH$_2$OPh, CH$_2$CH$_2$OH, CH$_2$CH$_2$OMe, $(CH_2)_4$OH, $(CH_2)_6$OH, CH$_2$OCOCH$_3$, CH$_2$OCOC(CH$_3)_3$, CH$_2$OCOPh, CHMeOCOPh, CH$_2$SMe, CH$_2$CH$_2$SMe, CH$_2$NH$_2$, CH$_2$NHMe, CH$_2$NHEt, CH$_2$NMe$_2$, CH$_2$NHiPr, CH$_2$CH$_2$NHMe, CH$_2$CH$_2$NMe$_2$, CH$_2$CH$_2$NEt$_2$, piperidin-1-ylethyl, morpholin-1-yl-ethyl, CH$_2$NHCOPh, CH$_2$NHCOMe, CH$_2$N(Me)COMe, CH$_2$NHCOEt, CH$_2$NHCOCH(CH$_3)_2$, CH$_2$CH$_2$NHCOMe, CH$_2$COOH, CH$_2$COOMe, CH₂COOEt, CH₂COOiPr, CH₂COOBu, CH₂COOtBu, CH₂COOCH₂CH=CH₂, CH₂COOCH₂CCH, (CH₂)₃COOH, (CH₂)₃COOMe, CH₂CONMe₂, CH₂CONHMe, CH₂CONHtBu, phenyl, 4-methylphenyl, 3-methylphenyl, 2-methylphenyl, 3,5-dimethylphenyl, 2,4-dimethylphenyl, 3,4-dimethylphenyl, 4-ethylphenyl, 4-ipropylphenyl, 4-tbutylphenyl, 4-methoxyphenyl, 2-methoxyphenyl, 3-methoxyphenyl, 3,4-dimethoxyphenyl, 3,5-dimethoxyphenyl, 3,4,5-trimethoxyphenyl, 4-ethoxyphenyl, 4-ipropoxyphenyl, 4-trifluoromethoxyphenyl, 4-hydroxyphenyl, 4-fluorophenyl, 2,4-difluorophenyl, 2,6-difluorophenyl, 2-fluorophenyl, 3-fluorophenyl, 2-chlorophenyl, 3-chlorophenyl, 4-chlorophenyl, 3,5-chlorophenyl, 4-bromophenyl, 4-chloro-2-fluorophenyl, 4-trifluoromethylphenyl, 3-trifluoromethylphenyl, 2-fluoro-4-trifluoromethylphenyl, 2-chloro-4-trifluoromethylphenyl, 4-chloro-2-methylphenyl, 2-chloro-6-methylphenyl, 3-fluoro-4-methylphenyl, 3,5-difluoro-4-methylphenyl, 4-methylsulphanylphenyl, 4-methylsulphinylphenyl, 4-methylsulphonylphenyl, 4-carboxyphenyl, 4-methoxycarbonylphenyl, 3-methoxycarbonylphenyl, 4-ethoxycarbonylphenyl, 4-carbamoylphenyl, 4-methylcarbamoylphenyl, 4-ethylcarbamoylphenyl, 4-dimethylcarbamoylphenyl, 4-(prop-2-en-1-ylcarbamoyl)phenyl, NH₂, NHMe, NHEt, NHPr, NHiPr, NHBu, NHtBu, NHCH₂CH=CH₂, NHCH₂CCH, cyclopentylamino, cyclohexylamino, NHBn, 4-chlorobenzylamino, 4-methoxybenzylamino, NHPh, 4-fluorophenylamino, 2-fluorophenylamino, 3,5-dichlorophenylamino, 2-methylphenylamino, 4-methylphenylamino, 3-cyanophenylamino, 3-trifluoromethylphenylamino, 4-methoxyphenylamino, 4-trifluoromethoxyphenylamino, pyridin-3-ylamino, pyridin-2-ylamino, NMe₂, N(Me)Et, NEt₂, NHCH₂COOEt, NHCH₂COOMe, NH(CH₂)₂COOEt, N=CHNMe₂, N=C(Me)NMe₂, NHCOMe, NHCOEt, NHCOPr, NHCOBu, NHCOtBu, NHCOCHMe₂, NHCOCH₂CHMe₂, NHCOCH=CH₂, acetyl(methyl)amino, acetyl(ethyl)amino, acetyl(propyl)amino, acetyl(ipropyl)amino, acetyl(butyl)amino, acetyl(phenyl)amino, acetyl(pentyl)amino, acetyl(benzyl)amino, cyclopropylcarbonylamino, cyclobutylcarbonylamino, cyclopentylcarbonylamino, cyclohexylcarbonylamino, cyclopentylacetylamino, phenylacetylamino, 3-phenylpropanoylamino, phenylcarbonylamino, methyl(phenylcarbonyl)amino, ethyl(phenylcarbonyl)amino, propyl(phenylcarbonyl)amino, (4-ethylphenylcarbonyl)amino, (2-chlorophenylcarbonyl)amino, (3-chlorophenylcarbonyl)amino, (4-chlorophenylcarbonyl)amino, (3-methoxycarbonylphenylcarbonyl)amino, (3-carboxyphenylcarbonyl)amino, (2-hydroxyphenylcarbonyl)amino, (4-methoxyphenylcarbonyl)amino, (2,6-dimethylphenylcarbonyl)amino, (4-cyanophenylcarbonyl)amino, (4-methoxycarbonylphenylcarbonyl)amino, (4-methoxycarbonylphenyl)carbonyl(methyl)amino, (4-carboxyphenylcarbonyl)amino, (pyridin-2-ylcarbonyl)amino, (pyridin-3-ylcarbonyl)amino, (pyridin-4-ylcarbonyl)amino, (thiophen-2-ylcarbonyl)amino, (furan-2-ylcarbonyl)amino, (6-chloropyridin-3-ylcarbonyl)amino, (6-methylpyridin-3-ylcarbonyl)amino, (6-methoxypyridin-3-ylcarbonyl)amino, (2-methoxypyridin-3-ylcarbonyl)amino, (pyrazin-2-ylcarbonyl)amino, NHCOCF₃, NHCOCH₂Cl, NHCO(CH₂)₃Cl, NHCO(CH₂)₄Cl, NHCO(CH₂)₅Cl, NHCOCH₂OH, NHCOCH₂OMe, NHCOCH(Me)OH, NHCOCH₂NMe₂, NHCOCH₂COOEt, NHCOCH₂COOMe, NHCO(CH₂)₂COOEt; NH(CH₂)₂Ph, NHCOOMe, NHCOOEt, NHCOOCH₂CH₂Cl, NHCONMe₂, NHCONHEt, NHCONHPr, NHCONHPh, (2-chlorophenyl)carbamoylamino, (3-chlorophenyl)carbamoylamino, (4-chlorophenyl)carbamoylamino, (2-fluorophenyl)carbamoylamino, (3-fluorophenyl)carbamoylamino, (4-fluorophenyl)carbamoylamino, (2-methylphenyl)carbamoylamino, (3-methylphenyl)carbamoylamino, (4-methylphenyl)carbamoylamino, (3-methoxyphenyl)carbamoylamino, or (4-methoxyphenyl)carbamoylamino;

$R^2$ represents phenyl, naphthalen-1-yl, naphthalen-2-yl, 2,3-dihydro-1H-inden-5-yl, 4-chlorophenyl, 3-chlorophenyl, 2-chlorophenyl, 4-fluorophenyl, 3-fluorophenyl, 2-fluorophenyl, 4-bromophenyl, 3-bromophenyl, 3,5-dichlorophenyl, 2,4-difluorophenyl, 2,6-difluorophenyl, 2,4,6-trifluorophenyl, 3,4-dichlorophenyl, 2-chloro-4-fluorophenyl, 3-cyanophenyl, 4-cyanophenyl, 4-hydroxyphenyl, 4-methylphenyl, 3-methylphenyl, 2-methylphenyl, 3,5-dimethylphenyl, 3,4-dimethylphenyl, 4-ethylphenyl, 3-ethylphenyl, 4-propylphenyl, 3-propylphenyl, 4-isopropylphenyl, 4-butylphenyl, 4-t-butylphenyl, 4-hexylphenyl, 4-fluoro-3-methylphenyl, 4-cyclohexylphenyl, 4-methoxyphenyl, 3-methoxyphenyl, 2-methoxyphenyl, 3,4-dimethoxyphenyl, 3,4,5-trimethoxyphenyl, 4-ethoxyphenyl, 4-butoxyphenyl, 4-benzyloxyphenyl, 4-(trifluoromethyl)phenyl, 3-(trifluoromethyl)phenyl, 4-(trifluoromethoxy)phenyl, 1,3-benzodioxol-5-yl, 2,2-difluoro-1,3-benzodioxol-5-yl, 4-(dimethylamino)phenyl, 3-bromo-4-dimethylaminophenyl, 4-(methylsulphanyl)phenyl, 4-methoxycarbonylphenyl, 4-ethoxycarbonylphenyl, 3-methoxycarbonylphenyl, 3-carboxyphenyl, furan-2-yl, 5-methylfuran-2-yl, 3-methylfuran-2-yl, furan-3-yl, thiophen-2-yl, pyridin-2-yl, 5-methylpyridin-2-yl, 6-methylpyridin-2-yl, 5-chloropyridin-2-yl, pyridin-3-yl, or pyridin-4-yl;

$R^3$ represents hydrogen, hydroxyl, methoxy, cyano, methyl, chloromethyl, hydroxymethyl, cyanomethyl, pyrrolidin-1-ylmethyl, COOMe, COOEt, phenylsulphanyl, benzylsulphanyl, phenylsulphonyl, amino, NHMe, NHEt, NHPr, NHBu, NHCH₂CH=CH₂, NHCH₂CCH, cyclopropylamino, cyclobutylamino, cyclohexylamino, cyclopentylamino, cyclohexyl(methyl)amino, 4-methylpiperazin-1-yl, piperidin-1-yl, pyrrolidin-1-yl, morpholin-1-yl, NMe₂, NEt₂, NHCH₂CH₂OCH₃, NHCH(Me)CH₂OCH₃, NHCOPh, (thiophen-2-ylcarbonyl)amino, (naphthalen-1-ylcarbonyl)amino, NHCOMe, NHCOEt, NHCOtBu, cyclopentylcarbonylamino, cyclohexylcarbonylamino, NHCO(CH₂)₂CH₃, NHCO(CH₂)₃CH₃, NHCO(CH₂)₄CH₃, (1-methylcyclohexyl)carbonylamino, NHCOOtBu, NHCONHCH₂CH₃, phenylacetylamino, 3-phenylpropanoylamino, 4-phenylbutanoylamino, 5-phenylpentanoylamino, methyl(phenylacetyl)amino, methyl(3-phenylpropanoyl)amino, (3-(4-fluorophenyl)propanoyl)amino, (3-(4-methoxyphenyl)propanoyl)amino, cyclopentylacetylamino, (cyclohexylmethyl)amino, (cyclopentylmethyl)amino, benzylamino, 2-phenylethylamino, 3-phenylpropylamino, benzyl(methyl)amino, methyl(2-phenylethyl)amino, (R)—NHCH(Me)Ph, (S)—NHCH(Me)Ph, (thiophen-2-ylmethyl)amino, 4-fluorobenzylamino, 4-chlorobenzylamino, 3-chlorobenzylamino, 2-chlorobenzylamino, 4-methoxybenzylamino, 3-methoxybenzylamino, 2-methoxybenzylamino, or (naphthalen-2-ylmethyl)amino;
and
$R^4$ represents hydrogen or methyl.

5. The method according to claim 1, wherein
$R^1$ represents hydrogen,
methyl, ethyl, propyl, 1-methylethyl, butyl, 1,1-dimethylethyl, pentyl, cyclohexyl, $CH_2CF_3$, $CF_2CH_3$, benzyl, 2-phenylethyl, 3-phenylpropyl, acetyl, COOH, COOEt, CHMeOH, $(CH_2)_4OH$, $(CH_2)_6OH$, CHMeOCOPh, $CH_2SMe$, $CH_2CH_2SMe$, $CH_2NH_2$, $CH_2NHMe$, $CH_2NHCOPh$, $CH_2COOH$, $CH_2COOEt$, $(CH_2)_3COOH$, $CH_2CONHMe$, phenyl, 4-methylphenyl, 3-methylphenyl, 2-methylphenyl, 4-methoxyphenyl, 2-methoxyphenyl, 4-hydroxyphenyl, 4-fluorophenyl, 2,4-difluorophenyl, 2,6-difluorophenyl, 2-fluorophenyl, 3-fluorophenyl, 2-chlorophenyl, 3-chlorophenyl, 4-chlorophenyl, 4-methylsulphanylphenyl, 4-methylsulphinylphenyl, 4-methylsulphonylphenyl, 4-carboxyphenyl, 4-methoxycarbonylphenyl, 4-carbamoylphenyl, $NH_2$, NHMe, NHEt, NHPr, NHiPr, NHBu, NHBn, NHPh, pyridin-3-ylamino, pyridin-2-ylamino, $NMe_2$, $NEt_2$, $NHCH_2COOEt$, $NH(CH_2)_2COOEt$, N=CHNMe$_2$, N=C(Me)NMe$_2$, NHCOMe, NHCOEt, NHCOPr, NHCOBu, NHCOtBu, NHCOCHMe$_2$, NHCOCH$_2$CHMe$_2$, NHCOCH=CH$_2$, acetyl(methyl)amino, acetyl(ethyl)amino, acetyl(propyl)amino, acetyl(ipropyl)amino, acetyl(butyl)amino, acetyl(phenyl)amino, acetyl(pentyl)amino, acetyl(benzyl)amino, cyclopentylcarbonylamino, cyclohexylcarbonylamino, cyclopentylacetylamino, phenylacetylamino, 3-phenylpropanoylamino, phenylcarbonylamino, methyl(phenylcarbonyl)amino, ethyl(phenylcarbonyl)amino, propyl(phenylcarbonyl)amino, (4-ethylphenylcarbonyl)amino, (2-chlorophenylcarbonyl)amino, (3-chlorophenylcarbonyl)amino, (4-chlorophenylcarbonyl)amino, (3-methoxycarbonylphenylcarbonyl)amino, (3-carboxyphenylcarbonyl)amino, (2-hydroxyphenylcarbonyl)amino, (4-methoxyphenylcarbonyl)amino, (2,6-dimethylphenylcarbonyl)amino, (4-cyano-phenylcarbonyl)amino, (4-methoxycarbonylphenylcarbonyl)amino, (4-methoxycarbonylphenyl)carbonyl(methyl)amino, (4-carboxyphenylcarbonyl)amino, (pyridin-2-ylcarbonyl)amino, (pyridin-3-ylcarbonyl)amino, (pyridin-4-ylcarbonylamino, (thiophen-2-ylcarbonyl)amino, (furan-2-ylcarbonyl)amino, (6-chloropyridin-3-ylcarbonyl)amino, (6-methylpyridin-3-ylcarbonyl)amino, (6-methoxypyridin-3-ylcarbonyl)amino, (2-methoxypyridin-3-ylcarbonyl)amino, (pyrazin-2-ylcarbonyl)amino, $NHCOCF_3$, $NHCOCH_2Cl$, $NHCO(CH_2)_3Cl$, $NHCO(CH_2)_4Cl$, $NHCO(CH_2)_5Cl$, $NHCOCH_2OH$, $NHCOCH_2OMe$, NHCOCH(Me)OH, $NHCOCH_2NMe_2$, $NHCOCH_2COOEt$, $NHCOCH_2COOMe$, $NHCO(CH_2)_2COOEt$, or $NHCOOCH_2CH_2Cl$, $NH(CH_2)_2Ph$;
$R^2$ represents phenyl, naphthalen-1-yl, 4-chlorophenyl, 3-chlorophenyl, 2-chlorophenyl, 4-fluorophenyl, 3-fluorophenyl, 4-bromophenyl, 3-bromophenyl, 3,5-dichlorophenyl, 3,4-dichlorophenyl, 3-cyanophenyl, 4-hydroxyphenyl, 4-methylphenyl, 3-methylphenyl, 2-methylphenyl, 3,5-dimethylphenyl, 3,4-dimethylphenyl, 4-ethylphenyl, 3-ethylphenyl, 4-propylphenyl, 3-propylphenyl, 4-isopropylphenyl, 4-butylphenyl, 4-t-butylphenyl, 4-hexylphenyl, 4-fluoro-3-methylphenyl, 4-methoxyphenyl, 3-methoxyphenyl, 2-methoxyphenyl, 3,4-dimethoxyphenyl, 3,4,5-trimethoxyphenyl, 4-ethoxyphenyl, 4-butoxyphenyl, 4-benzyloxyphenyl, 4-(trifluoromethyl)phenyl, 3-(trifluoromethyl)phenyl, 4-(trifluoromethoxy)phenyl, 1,3-benzodioxol-5-yl, 4-(dimethylamino)phenyl, 4-(methylsulphanyl)phenyl, or furan-2-yl, or thiophen-2-yl;
$R^3$ represents hydrogen, hydroxyl, methyl, chloromethyl, hydroxymethyl, cyanomethyl, pyrrolidin-1-ylmethyl, COOMe, phenylsulphanyl, benzylsulphanyl, phenylsulphonyl, amino, cyclohexylamino, cyclopentylamino, cyclohexyl(methyl)amino, 4-methylpiperazin-1-yl, piperidin-1-yl, pyrrolidin-1-yl, morpholin-1-yl, NHCOPh, (thiophen-2-ylcarbonyl)amino, (naphthalen-1-ylcarbonyl)amino, NHCOMe, NHCOEt, NHCOtBu, cyclopentylcarbonylamino, cyclohexylcarbonylamino, NHCOPr, NHCOBu, $NHCO(CH_2)_4CH_3$, (1-methylcyclohexyl)carbonylamino, NHCOOtBu, NHCONHEt, phenylacetylamino, 3-phenylpropanoylamino, 4-phenylbutanoylamino, 5-phenylpentanoylamino, methyl(phenylacetyl)amino, methyl(3-phenylpropanoyl)amino, (3-(4-fluorophenyl)propanoyl)amino, (3-(4-methoxyphenyl)propanoyl)amino, cyclopentylacetylamino, (cyclohexylmethyl)amino, (cyclopentylmethyl)amino, benzylamino, 2-phenylethylamino, 3-phenylpropylamino, benzyl(methyl)amino, methyl(2-phenylethyl)amino, (R)—NHCH(Me)Ph, (S)—NHCH(Me)Ph, (thiophen-2-ylmethyl)amino, 4-fluorobenzylamino, 4-chlorobenzylamino, 3-chlorobenzylamino, 2-chlorobenzylamino, 4-methoxybenzylamino, 3-methoxybenzylamino, 2-methoxybenzylamino, or (naphthalen-2-ylmethyl)amino;
and
$R^4$ represents hydrogen.

6. A crop protection composition for controlling phytopathogenic and mycotoxin-producing fungi, comprising at least one 5-pyridin-4-yl-1,3-thiazole of the formula (I) or an agrochemically active salt thereof, and at least one extender, at least one surfactant, or a combination thereof

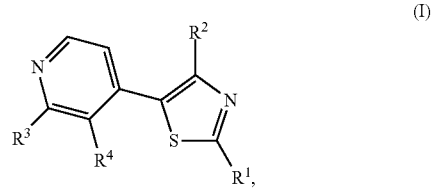

(I)

in which
$R^1$ represents hydrogen, represents an optionally hydroxyl-, amino-, cyano-, $C_1$-$C_4$-alkoxy-, $R^5$-, $OR^5$-, ($C_1$-$C_4$-alkyl)sulphanyl-, ($C_1$-$C_4$-alkyl)sulphinyl-, ($C_1$-$C_4$-alkyl)sulphonyl-, ($C_1$-$C_4$-alkyl)amino-, bis($C_1$-$C_4$-alkyl)amino-, $C_1$-$C_4$-alkylcarbonyloxy- or $OCOR^5$-substituted $C_1$-$C_8$-alkyl, $C_1$-$C_6$-haloalkyl,
represents an optionally $C_1$-$C_4$-alkyl- or halogen-substituted $C_3$-$C_8$-cycloalkyl,
represents $COR^6$, $COOR^6$, $CON(R^6)_2$, $(CH_2)_mOR^6$, $(CH_2)_mSR^6$, $(CH_2)_mSOR^6$, $(CH_2)_mSO_2R^6$, $(CH_2)_mSON(R^6)_2$, $(CH_2)_mSO_2N(R^6)_2$, $(CH_2)_mN(R^6)_2$, $(CH_2)_mNR^6COR^6$, $(CH_2)_mCOOR^6$, $(CH_2)_mCON(R^6)_2$, $(CH_2)_mCOR^6$, or $(CH_2)_mC(NOR^6)R^6$, represents $N(R^6)_2$, $NR^6(CH_2)_mCOOR^6$, $N{=}CR^6N(R^6)_2$, $NR^6COR^6$, $NR^6CO(CH_2)_mOR^6$, $NR^6COCH(C_1\text{-}C_4\text{-alkyl})OR^6$, $NR^6CO(CH_2)_mN(R^6)_2$, $NR^6CO(CH_2)_mCOOR^6$, $NR^6COOR^7$, $NR^6CON(R^6)_2$, $NR^6CO(CH_2)_mR^8$, or $NR^6(CH_2)_mR^8$, or $R^1$ represents a phenyl radical which is optionally mono- or polysubstituted by identical or different radicals selected from the group consisting of $C_1\text{-}C_4$-alkyl, halogen, cyano, $C_1\text{-}C_4$-haloalkyl, $OR^6$, $N(R^6)_2$, $SR^6$, $SOR^6$, $S(O)_2R^6$, $SO_2N(R^6)_2$, $COOR^6$, $COR^6$, $C(NOR^6)R^6$, $(CH_2)_mOR^6$, $CON(R^6)_2$, and $CH{=}CR^6COOR^6$, $R^2$ represents an aryl radical which is optionally mono- or polysubstituted by identical or different radicals selected from the group consisting of halogen, cyano, hydroxyl, $SF_6$, nitro, $C_1\text{-}C_6$-alkyl, $C_3\text{-}C_8$-cycloalkyl, $C_1\text{-}C_4$-haloalkyl, $C_2\text{-}C_6$-alkenyl, $C_2\text{-}C_6$-alkynyl, $OR^6$, $(C_1\text{-}C_4)\text{alkoxy}(C_1\text{-}C_4)\text{alkyl}$, $(C_1\text{-}C_2)\text{alkanediylbisoxy}$, $(C_1\text{-}C_2)\text{haloalkanediylbisoxy}$, $C_3\text{-}C_5$-alkanediyl, $N(R^6)_2$, $SR^6$, $COOR^6$, $COR^6$, $C(R^6)NOR^6$, $CON(R^6)_2$, $CH{=}CR^6COOR^6$, $O(CH_2)_mCOOR^6$, $NR^6COR^6$, $NR^6CON(R^6)_2$, $NR^6COO(R^7)$ and optionally halogen-, $C_1\text{-}C_4$-alkyl-, or $C_1\text{-}C_4$-alkoxy-substituted phenyl, or $R^2$ represents a five- or six-membered heteroaromatic which contains up to four heteroatoms selected from the group consisting of N, O and S, where two oxygen atoms are not adjacent, and which is optionally mono- or polysubstituted by identical or different radicals selected from the group consisting of halogen, cyano, $C_1\text{-}C_4$-alkyl, $C_1\text{-}C_4$-alkoxy, $C_1\text{-}C_4$-haloalkyl, phenyl and $C_3\text{-}C_8$-cycloalkyl;

$R^3$ represents hydrogen, cyano, hydroxyl, $OR^6$, cyano, amino, $C_1\text{-}C_6$-alkyl, $C_1\text{-}C_8$-haloalkyl, $(CH_2)_mOR^6$, $(CH_2)_mCN$, $(CH_2)_mN(R^6)_2$, $COOR^6$, $CON(R^6)_2$, $SR^6$, $SOR^6$, $S(O)_2R^6$, $NR^6COR^6$, $NR^6COOR^7$, $NR^6CON(R^6)_2$, $NR^6SO_2R^6$, $N{=}S(O)(R^6)_2$; $N{=}CR^6N(R^6)_2$, $NR^6CO(CH_2)_mR^9$ or $NR^6(CH_2)_mR^9$;

or $R^3$ represents a heterocycle selected from the group consisting of pyrrolidine, piperidine, piperazine, and morpholine, each of which is unsubstituted or optionally substituted by oxo, halogen, or $(C_1\text{-}C_4)$alkyl;

$R^4$ represents hydrogen or $C_1\text{-}C_4$-alkyl;

$R^5$ represents a phenyl radical which is optionally substituted by halogen, hydroxyl, cyano, $C_1\text{-}C_4$-alkoxy, $C_1\text{-}C_2$-haloalkoxy, $C_1\text{-}C_2$-haloalkyl, $C_1\text{-}C_4$-alkoxycarbonyl, or carboxyl;

$R^6$ independently of one another represent hydrogen, $C_1\text{-}C_6$-alkyl, optionally $C_1\text{-}C_1$-alkyl- or halogen-substituted $C_3\text{-}C_6$-cycloalkyl, $C_1\text{-}C_6$-haloalkyl, $C_2\text{-}C_6$-alkenyl, $C_2\text{-}C_6$-alkynyl, $C_1\text{-}C_4$-alkoxy$(C_1\text{-}C_4)$alkyl, hydroxy$(C_1\text{-}C_4)$alkyl, represents aryl or aryl$(C_1\text{-}C_4)$alkyl, each of which is optionally mono- or polysubstituted by identical or different radicals selected from the group consisting of halogen, cyano, hydroxyl, $C_1\text{-}C_1$-alkyl, $C_1\text{-}C_4$-alkoxy, $C_1\text{-}C_4$-haloalkoxy, $C_1\text{-}C_4$-alkylcarbonyl, carboxyl and $C_1\text{-}C_4$-alkoxycarbonyl, or represents a 3- to 7-membered saturated or unsaturated cycle which contains no or up to four heteroatoms selected from the group consisting of N, O and S, where two oxygen atoms are not adjacent, and which is unsubstituted or optionally mono- or polysubstituted by identical or different radicals selected from the group consisting of halogen, cyano, $C_1\text{-}C_4$-haloalkyl, $C_1\text{-}C_4$-alkoxy, $C_1\text{-}C_4$-haloalkoxy, $C_1\text{-}C_4$-alkylcarbonyl and $C_1\text{-}C_4$-alkoxycarbonyl, or if two radicals $R^6$ are attached to a nitrogen atom, two radicals $R^6$ form a 3- to 7-membered saturated or unsaturated cycle which contains up to four further heteroatoms selected from the group consisting of N, O and S, where two oxygen atoms are not adjacent, and which is unsubstituted or optionally mono- or polysubstituted by identical or different radicals selected from the group consisting of halogen, cyano, $C_1\text{-}C_4$-alkyl, $C_1\text{-}C_4$-haloalkyl, $C_1\text{-}C_4$-alkoxy, $C_1\text{-}C_4$-haloalkoxy, $C_1\text{-}C_4$-alkylcarbonyl and $C_1\text{-}C_4$-alkoxycarbonyl, or if two radicals $R^6$ are present in adjacent positions in the grouping $NR^6COR^6$, two radicals $R^6$ form a 3- to 7-membered saturated or unsaturated cycle which contains up to four further heteroatoms selected from the group consisting of N, O and S, where two oxygen atoms are not adjacent, and which is unsubstituted or optionally mono- or polysubstituted by identical or different radicals selected from the group consisting of halogen, hydroxyl, $C_1\text{-}C_4$-alkyl, $C_1\text{-}C_4$-haloalkyl, $C_1\text{-}C_4$-alkoxy, $C_1\text{-}C_4$-haloalkoxy and phenyl, or if two radicals $R^6$ are attached to a sulphur atom, two radicals $R^6$ form a 5- to 7-membered cycle which contains up to two further heteroatoms selected from the group consisting of N, O and S, where two oxygen atoms are not adjacent, and which is unsubstituted or optionally $C_1\text{-}C_4$-alkyl-substituted;

$R^7$ independently of one another represent $C_1\text{-}C_6$-alkyl, optionally $C_1\text{-}C_4$-alkyl- or halogen-substituted $C_3\text{-}C_6$-cycloalkyl, $C_1\text{-}C_6$-haloalkyl, $C_2\text{-}C_6$-alkenyl, $C_2\text{-}C_6$-alkynyl, $C_1\text{-}C_4$-alkoxy$(C_1\text{-}C_4)$alkyl, hydroxy$(C_1\text{-}C_4)$alkyl, represent aryl or aryl$(C_1\text{-}C_4)$alkyl, each of which is optionally mono- or polysubstituted by identical or different radicals selected from the group consisting of halogen, cyano, hydroxyl, $C_1\text{-}C_4$-alkyl, $C_1\text{-}C_4$-haloalkyl, $C_1\text{-}C_4$-alkoxy, $C_1\text{-}C_4$-haloalkoxy, alkylcarbonyl, carboxyl and $C_1\text{-}C_4$-alkoxycarbonyl, or represent a 3- to 7-membered saturated or unsaturated cycle which contains no or up to four heteroatoms selected from the group consisting of N, O and S, where two oxygen atoms are not adjacent, and which is unsubstituted or optionally mono- or polysubstituted by identical or different radicals selected from the group consisting of halogen, cyano, $C_1\text{-}C_4$-haloalkyl, $C_1\text{-}C_4$-alkoxy, $C_1\text{-}C_4$-haloalkoxy, $C_1\text{-}C_4$-alkylcarbonyl and $C_1\text{-}C_4$-alkoxycarbonyl;

$R^8$ represents a 3- to 7-membered saturated, unsaturated or aromatic mono- or bicycle which contains no or up to four heteroatoms selected from the group consisting of N, O and S, where two oxygen atoms are not adjacent, and which is optionally substituted by oxo, hydroxyl, halogen, cyano, $C_1\text{-}C_4$-alkoxy, $C_1\text{-}C_4$-haloalkoxy, phenyl, carboxyl, $C_1\text{-}C_6$-alkylcarbonyl or $C_1\text{-}C_6$-alkoxycarbonyl;

$R^9$ represents a 3- to 7-membered saturated, unsaturated or aromatic mono- or bicycle which contains no or up to four heteroatoms selected from the group consisting of N, O and S, where two oxygen atoms are not adjacent, and which is unsubstituted or optionally mono- or polysubstituted by identical or different radicals selected from the group consisting of $C_1$-$C_4$-alkyl, halogen, cyano, $C_1$-$C_4$-haloalkyl and $C_1$-$C_4$-alkoxy; and m represents a number from 1 to 6.

7. A method for controlling phytopathogenic and mycotoxin-producing fungi, comprising contacting one or more 5-pyridin-4-yl-1,3-thiazoles of the formula (I) according to claim 1, or an agrochemically active salt thereof, with the fungi and/or their habitat.

8. The crop protection composition according to claim 6, wherein $R^1$ represents hydrogen, $C_1$-$C_6$-alkyl, $C_1$-$C_4$-haloalkyl, $C_3$-$C_8$-cycloalkyl, aryl($C_1$-$C_4$)alkyl, formyl, ($C_1$-$C_4$-alkyl)carbonyl, ($C_1$-$C_4$-haloalkyl)carbonyl, COOH, ($C_1$-$C_4$-alkoxy)carbonyl, ($C_3$-$C_6$-alkenyloxy)carbonyl, ($C_3$-$C_6$-alkynyloxy)carbonyl, ($C_1$-$C_4$-alkyl)carbamoyl, bis($C_1$-$C_4$-alkyl)carbamoyl, ($C_3$-$C_4$-alkenyl)carbamoyl, ($C_3$-$C_4$-alkynyl)carbamoyl, $CONHR^{10}$, $C_1$-$C_6$-hydroxyalkyl, $C_1$-$C_4$-alkoxy($C_1$-$C_4$)alkyl, phenyloxy($C_1$-$C_4$)alkyl, ($C_1$-$C_4$-alkyl)carbonyloxy($C_1$-$C_4$)alkyl, phenylcarbonyloxy($C_1$-$C_4$)alkyl, ($C_1$-$C_4$-alkyl)sulphanyl($C_1$-$C_4$)alkyl, amino($C_1$-$C_4$)alkyl, ($C_1$-$C_4$-alkyl)amino($C_1$-$C_4$)alkyl, bis($C_1$-$C_4$-alkyl)amino($C_1$-$C_4$)alkyl, piperidin-1-ylethyl, morpholin-1-ylethyl, phenylcarbonylamino($C_1$-$C_4$)alkyl, ($C_1$-$C_4$-alkyl)carbonylamino($C_1$-$C_4$)alkyl, $(CH_2)_m N(C_1$-$C_2$-alkyl)CO($C_1$-$C_4$-alkyl), $(CH_2)_m COOH$, $(CH_2)_m COO(C_1$-$C_4$)alkyl, $(CH_2)_m COO(C_3$-$C_5$)alkenyl, $(CH_2)_m COO(C_3$-$C_5$)alkynyl, $(CH_2)_m CONH(C_1$-$C_4$)alkyl, $(CH_2)_m CON((C_1$-$C_4$)alkyl)_2$, $(CH_2)_m NHCOR^{10}$, $(CH_2)_m OCOR^{10}$, $(CH_2)_m R^{10}$, amino, $NH(C_1$-$C_4$-alkyl), $N(C_1$-$C_4$-alkyl)_2$, $NH(C_3$-$C_5$-alkenyl), $NH(C_3$-$C_5$-alkynyl), $NH(C_3$-$C_6$-cycloalkyl), $NHR^{10}$, $NH(R^{11})$, $NH(CH_2)_m R^{10}$, $N=CHN(C_1$-$C_4$-alkyl)_2$ $N=C(C_1$-$C_2$-alkyl)N(C_1$-$C_4$-alkyl)_2$, $NH(CH_2)_m COO(C_1$-$C_4$-alkyl), NHCO($C_1$-$C_4$-alkyl), $NHCO(C_2$-$C_5$-alkenyl), $N(C_1$-$C_5$-alkyl)CO($C_1$-$C_4$-alkyl), $N(C_3$-$C_5$-alkenyl)CO($C_1$-$C_4$-alkyl), $N(C_3$-$C_5$-alkynyl)CO($C_1$-$C_4$-alkyl),)N($R^{10}$)CO($C_1$-$C_4$-alkyl), N(Bn)CO($C_1$-$C_4$-alkyl), $NHCO(C_3$-$C_6$-cycloalkyl), $NHCOCH_2(C_3$-$C_6$-cycloalkyl), $NHCO(C_1$-$C_5$-haloalkyl), $NHCO(C_1$-$C_4$-alkoxy), $NHCO(C_1$-$C_4$-haloalkoxy), $NHCO(CH_2)_m COO(C_1$-$C_4$-alkyl), $NHCOCH_2OH$, $NHCOCH_2OMe$, $NHCOCH(Me)OH$, $NHCOCH_2NMe_2$, $NHCO(CH_2)_m R^{10}$, $NHCOR^{10}$, $N(C_1$-$C_4$-alkyl)$COR^{10}$, $N(C_3$-$C_5$-alkenyl)CO($R^{10}$), $N(C_3$-$C_5$-alkynyl)CO($R^{10}$), $NHCONH(C_1$-$C_4$alkyl), $NHCON(C_1$-$C_4$alkyl)_2$, $NHCONHR^{10}$, $NHCO(R^{11})$, or $N(C_1$-$C_4$-alkyl)CO($R^{11}$), or $R^1$ represents a phenyl radical which is optionally mono- or polysubstituted by identical or different radicals selected from the group consisting of halogen, cyano, hydroxyl, $C_1$-$C_4$-alkyl, $C_1$-$C_4$-alkoxy, $C_1$-$C_4$-haloalkoxy, $C_1$-$C_4$-haloalkyl, $C_1$-$C_4$-alkylsulphonyl, $C_1$-$C_4$-alkylsulphinyl, $C_1$-$C_4$-alkylsulphanyl, $C_1$-$C_4$-alkylcarbonyl, $C_1$-$C_4$-alkoxycarbonyl, carboxyl, carbamoyl, $C_1$-$C_4$-alkylcarbamoyl, bis($C_1$-$C_4$-alkyl)carbamoyl and ($C_3$-$C_4$)-alkenylcarbamoyl, $R^2$ represents a phenyl or naphthalenyl radical, each of which is optionally mono- or polysubstituted by identical or different radicals selected from the group consisting of halogen, cyano, hydroxyl, $C_1$-$C_6$-alkyl, $C_3$-$C_6$-cycloalkyl, $C_1$-$C_4$-alkoxy, ($C_1$-$C_4$)alkoxy($C_1$-$C_4$)alkyl, benzyloxy, $C_1$-$C_4$-haloalkyl, $C_1$-$C_4$-haloalkoxy, methanediylbisoxy, difluoromethanediylbisoxy, propane-1,3-diyl, $NH(C_1$-$C_4$-alkyl), $N(C_1$-$C_4$-alkyl)_2$, ($C_1$-$C_4$)alkylsulphanyl, ($C_1$-$C_4$)alkoxycarbonyl, and carboxyl, or represents a heteroaromatic selected from the group consisting of furan, thiophene, and pyridine, each of which is unsubstituted or optionally substituted by fluorine, chlorine, or $C_1$-$C_4$-alkyl;

$R^3$ represents hydrogen, hydroxyl, amino, cyano, ($C_1$-$C_4$) alkyl, ($C_1$-$C_4$)haloalkyl, ($C_1$-$C_4$)alkoxy, hydroxymethyl, cyanomethyl, pyrrolidin-1-ylmethyl, phenylsulphanyl, benzylsulphanyl, phenylsulphonyl, ($C_1$-$C_4$)alkoxycarbonyl, ($C_1$-$C_4$)alkylcarbamoyl, bis($C_1$-$C_4$)alkylcarbamoyl, $NH(C_1$-$C_4$-alkyl), $N(C_1$-$C_4$-alkyl)_2$, $NH(C_1$-$C_4$-haloalkyl), ($C_1$-$C_2$)alkoxy($C_1$-$C_4$)alkylamino, hydroxy($C_1$-$C_4$)alkylamino, $NH(C_3$-$C_5$-alkenyl), $NH(C_3$-$C_5$-alkynyl), $NH(C_3$-$C_6$-cycloalkyl), $N(C_1$-$C_4$-alkyl)($C_3$-$C_6$-cycloalkyl), $NHCO(C_1$-$C_6$-alkyl), $N(C_1$-$C_4$-alkyl)CO($C_1$-$C_6$-alkyl), $N(C_3$-$C_4$-alkenyl)CO($C_1$-$C_6$-alkyl), $N(C_3$-$C_4$-alkynyl)CO($C_1$-$C_6$-alkyl), $NHCO(C_1$-$C_6$-haloalkyl), $N(C_1$-$C_4$-alkyl)CO($C_1$-$C_6$-haloalkyl), $N(C_3$-$C_4$-alkenyl)CO($C_1$-$C_6$-haloalkyl), $N(C_3$-$C_4$-alkynyl)CO($C_1$-$C_6$-haloalkyl), $NHCO(C_3$-$C_6$-cycloalkyl), $N(C_1$-$C_4$-alkyl)CO($C_3$-$C_6$-cycloalkyl), $N(C_3$-$C_4$-alkenyl)CO($C_3$-$C_6$-cycloalkyl), $N(C_3$-$C_4$-alkynyl)CO($C_3$-$C_6$-cycloalkyl), (2-methylcyclopropyl)carbonylamino, (1-methylcyclohexyl)carbonylamino, $NHCO(C_2$-$C_4$-alkenyl), $NHCOR^{12}$, $N(C_1$-$C_4$-alkyl)CO($R^{12}$), $N(C_3$-$C_4$-alkenyl)CO($R^{12}$), $N(C_3$-$C_4$-alkynyl)CO($R^{12}$), $NHCO(CH_2)_m R^{12}$, $NMeCO(CH_2)_m R^{12}$, $NH(CH_2)_m R^{12}$, $NMe(CH_2)_m R^{12}$, $NHCO(CH_2)_m(C_3$-$C_6$-cycloalkyl), $NH(CH_2)_m(C_3$-$C_6$-cycloalkyl), $NHCOO(C_1$-$C_4$-alkyl), $NHCOO(C_1$-$C_4$-haloalkyl), $NHCONH(C_1$-$C_4$-alkyl), $NHCH(Me)R^{12}$, (thiophen-2-ylcarbonyl)amino, (thiophen-2-ylmethyl)amino, ($C_1$-$C_4$-alkyl)sulphonylamino, or ($C_3$-$C_6$-cycloalkyl)sulphonylamino, or $R^3$ represents a heterocycle selected from the group consisting of pyrrolidine, piperidine, piperazine, and morpholine, each of which is unsubstituted or optionally substituted by oxo, halogen, or ($C_1$-$C_4$)alkyl;

$R^4$ represents hydrogen or methyl;

$R^{10}$ represents a phenyl radical which is optionally substituted by halogen, hydroxyl, cyano, $C_1$-$C_4$-alkyl, $C_1$-$C_4$-alkoxy, $C_1$-$C_2$-haloalkoxy, $C_1$-$C_2$-haloalkyl, $C_1$-$C_4$-alkoxycarbonyl, or carboxyl;

$R^{11}$ represents a heteroaromatic selected from the group consisting of furan, thiophene, pyridine, and pyrazine which is optionally substituted by fluorine, chlorine, cyano, $C_1$-$C_4$-alkyl, $C_1$-$C_4$-alkoxy, $C_1$-$C_2$-haloalkyl, or $C_1$-$C_4$-alkoxycarbonyl;

$R^{12}$ represents a phenyl- or naphthalenyl radical which is optionally substituted by halogen, ($C_1$-$C_4$)alkyl ($C_1$-$C_4$)alkoxy, or ($C_1$-$C_4$)haloalkyl;

and m represents a number from 1 to 6.

9. The crop protection composition according to claim 6, wherein $R^1$ represents hydrogen, $C_1$-$C_6$-alkyl, $C_1$-$C_2$-haloalkyl, $C_3$-$C_6$-cycloalkyl, aryl($C_1$-$C_4$)alkyl, formyl, ($C_1$-$C_4$-alkyl)carbonyl, ($C_1$-$C_2$-haloalkyl)carbonyl, COOH, ($C_1$-$C_4$-alkoxy)carbonyl, ($C_3$-$C_4$-alkenyloxy)carbonyl, ($C_3$-$C_4$-alkynyloxy)carbonyl, $C_1$-$C_6$-hydroxyalkyl, $C_1$-$C_4$-alkoxy($C_1$-$C_4$)alkyl, phenoxy($C_1$-$C_4$)alkyl, ($C_1$-$C_4$-alkyl)carbonyloxy($C_1$-$C_2$)alkyl, phenylcarbonyloxy($C_1$-$C_2$)alkyl, ($C_1$-$C_4$-alkyl)sulphanyl($C_1$-$C_2$)alkyl, amino($C_1$-$C_2$)alkyl, ($C_1$-$C_4$-alkyl)amino($C_1$-$C_2$)alkyl, bis($C_1$-$C_4$-alkyl)amino($C_1$-$C_2$)alkyl, piperidin-1-yl-ethyl, morpholin-1-ylethyl, phenylcarbonylamino($C_1$-$C_2$)alkyl, ($C_1$-$C_4$-alkyl)carbonylamino($C_1$-$C_2$)alkyl, $(CH_2)_m$NMeCO($C_1$-$C_4$-alkyl), $(CH_2)_m$COOH, $(CH_2)_m$COO($C_1$-$C_4$-alkyl), $(CH_2)_m$COO($C_3$-$C_4$-alkenyl), $(CH_2)_m$COO($C_3$-$C_4$-alkynyl), $(CH_2)_m$CONH($C_1$-$C_4$) alkyl, $(CH_2)_m$CON(($C_1$-$C_4$)alkyl)$_2$, amino, NH($C_1$-$C_4$-alkyl), N($C_1$-$C_4$-alkyl)$_2$, NH($C_3$-$C_4$-alkenyl), NH($C_3$-$C_4$-alkynyl), NH($C_3$-$C_6$-cycloalkyl), NHR$^{10}$, NH$(CH_2)_m$R$^{10}$, NH(R$^{11}$), N=CHN($C_1$-$C_4$-alkyl)$_2$, N=C($C_1$-$C_2$-alkyl)N($C_1$-$C_4$-alkyl)$_2$, NH$(CH_2)_m$COO($C_1$-$C_4$-alkyl), NHCO($C_1$-$C_4$-alkyl), NHCO($C_2$-$C_4$-alkenyl), N($C_1$-$C_5$-alkyl)CO($C_1$-$C_4$-alkyl), N(Ph)CO($C_1$-$C_4$-alkyl), N(Bn)CO($C_1$-$C_4$-alkyl), NHCO($C_3$-$C_6$-cycloalkyl), NHCOCH$_2$($C_3$-$C_6$-cycloalkyl), NHCO($C_1$-$C_5$-haloalkyl), NHCO($C_1$-$C_4$-alkoxy), NHCO($C_1$-$C_4$-haloalkoxy), NHCO$(CH_2)_m$COO($C_1$-$C_4$-alkyl), NHCOCH$_2$OH, NHCOCH$_2$OMe, NHCOCH(Me)OH, NHCOCH$_2$NMe$_2$, NHCO$(CH_2)_m$R$^{10}$, NHCOR$^{10}$, N($C_1$-$C_4$-alkyl)COR$^{10}$, NHCONH($C_1$-$C_4$-alkyl), NHCON($C_1$-$C_4$-alkyl)$_2$, NHCONHR$^{10}$, or NHCO(R$^{11}$), or R$^1$ represents a phenyl radical which is optionally mono- or polysubstituted by identical or different radicals selected from the group consisting of fluorine, chlorine, bromine, hydroxyl, $C_1$-$C_4$-alkyl, $C_1$-$C_4$-alkoxy, $C_1$-$C_2$-haloalkoxy, $C_1$-$C_2$-haloalkyl, $C_1$-$C_2$-alkylsulphonyl, $C_1$-$C_2$-alkylsulphinyl, $C_1$-$C_2$-alkylsulphanyl, $C_1$-$C_4$-alkoxycarbonyl, carboxyl, carbamoyl, $C_1$-$C_4$-alkylcarbamoyl, bis($C_1$-$C_4$-alkyl)carbamoyl and ($C_3$-$C_4$)-alkenylcarbamoyl, R$^2$ represents a phenyl or naphthalenyl radical, each of which is optionally mono- or polysubstituted by identical or different radicals selected from the group consisting of halogen, cyano, hydroxyl, $C_1$-$C_6$-alkyl, $C_3$-$C_6$-cycloalkyl, $C_1$-$C_4$-alkoxy, benzyloxy, $C_1$-$C_4$-haloalkyl, $C_1$-$C_4$-haloalkoxy, methanediylbisoxy, difluoromethanediylbisoxy, propane-1,3-diyl, NH($C_1$-$C_4$-alkyl), N($C_1$-$C_4$-alkyl)$_2$, ($C_1$-$C_4$)alkylsulphanyl, ($C_1$-$C_4$)alkoxycarbonyl, and carboxyl, or R$^2$ represents a heteroaromatic selected from the group consisting of furan, thiophene, and pyridine, each of which is unsubstituted or optionally substituted by fluorine, chlorine, or $C_1$-$C_4$-alkyl;

R$^3$ represents hydrogen, hydroxyl, amino, cyano, ($C_1$-$C_2$) alkyl, ($C_1$-$C_2$)haloalkyl, ($C_1$-$C_2$)alkoxy, hydroxymethyl, cyanomethyl, pyrrolidin-1-ylmethyl, phenylsulphanyl, benzylsulphanyl, phenylsulphonyl, ($C_1$-$C_4$) alkoxycarbonyl, NH($C_1$-$C_4$-alkyl), N($C_1$-$C_4$-alkyl)$_2$, ($C_1$-$C_2$)alkoxy($C_1$-$C_4$)alkylamino, NH($C_3$-$C_4$-alkenyl), NH($C_3$-$C_4$-alkynyl), NH($C_3$-$C_6$-cycloalkyl), N(Me)($C_3$-$C_6$-cycloalkyl), NHCO($C_1$-$C_6$-alkyl), NHCO($C_3$-$C_6$-cycloalkyl), (1-methylcyclohexyl)carbonylamino, NHCOR$^{12}$, NMeCOR$^{12}$, NHCO$(CH_2)_m$R$^{15}$, NMeCO$(CH_2)_m$R$^{12}$, NH$(CH_2)_m$R$^{12}$, NMe$(CH_2)_m$R$^{12}$, NHCO$(CH_2)_m$($C_3$-$C_6$-cycloalkyl), NH$(CH_2)_m$($C_3$-$C_6$-cycloalkyl), NHCOO($C_1$-$C_4$-alkyl), NHCONH($C_1$-$C_4$-alkyl), NHCH(Me)R$^{12}$, (thiophen-2-ylcarbonyl)amino, or (thiophen-2-ylmethyl)amino, or R$^3$ represents a heterocycle selected from the group consisting of pyrrolidine, piperidine, piperazine, and morpholine, each of which is unsubstituted or optionally substituted by methyl;

R$^4$ represents hydrogen, methyl;

R$^{10}$ represents a phenyl radical which is optionally substituted by fluorine, chlorine, hydroxyl, cyano, $C_1$-$C_4$-alkyl, $C_1$-$C_4$-alkoxy, $C_1$-$C_2$-haloalkoxy, $C_1$-$C_2$-haloalkyl, $C_1$-$C_4$-alkoxycarbonyl, or carboxyl;

R$^{11}$ represents a heteroaromatic selected from the group consisting of furan, thiophene, pyridine, and pyrazine, each of which is optionally substituted by chlorine, methyl, or methoxy;

R$^{12}$ represents a phenyl- or naphthalenyl radical which is optionally substituted by fluorine, chlorine, methyl, methoxy, or trifluoromethyl;

and m represents a number from 1 to 4.

10. The crop protection composition according to claim 6, wherein

R$^1$ represents hydrogen,
methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, cyclopropyl, cyclobutyl, cyclopentyl, cyclohexyl, $CF_3$, $CHF_2$, $CH_2CF_3$, $CF_2CH_3$, benzyl, 2-phenylethyl, 1-phenylethyl, 3-phenylpropyl, formyl, acetyl, propanoyl, 2-methylpropanoyl, trifluoroacetyl, COOH, COOMe, COOEt, COOiPr, COOPr, COOCH$_2$CH=CH$_2$, COOCH$_2$CCH, CHMeOH, CMe$_2$OH CH$_2$OH, CH$_2$OMe, CH$_2$OEt, CH$_2$OPh, CH$_2$CH$_2$OH, CH$_2$CH$_2$OMe, $(CH_2)_4$OH, $(CH_2)_6$OH, CH$_2$OCOCH$_3$, CH$_2$OCOC(CH$_3$)$_3$, CH$_2$OCOPh, CHMeOCOPh, CH$_2$SMe, CH$_2$CH$_2$SMe, CH$_2$NH$_2$, CH$_2$NHMe, CH$_2$NHEt, CH$_2$NMe$_2$, CH$_2$NHiPr, CH$_2$CH$_2$NHMe, CH$_2$CH$_2$NMe$_2$, CH$_2$CH$_2$NEt$_2$, piperidin-1-ylethyl, morpholin-1-yl-ethyl, CH$_2$NHCOPh, CH$_2$NHCOMe, CH$_2$N(Me)COMe, CH$_2$NHCOEt, CH$_2$NHCOCH(CH$_3$)$_2$, CH$_2$CH$_2$NHCOMe, CH$_2$COOH, CH$_2$COOMe, CH$_2$COOEt, CH$_2$COOiPr, CH$_2$COOBu, CH$_2$COOtBu, CH$_2$COOCH$_2$CH=CH$_2$, CH$_2$COOCH$_2$CCH, $(CH_2)_3$COOH, $(CH_2)_3$COOMe, CH$_2$CONHMe, CH$_2$CONMe$_2$, CH$_2$CONHtBu, phenyl, 4-methylphenyl, 3-methylphenyl, 2-methylphenyl, 3,5-dimethylphenyl, 2,4-dimethylphenyl, 3,4-dimethylphenyl, 4-ethylphenyl, 4-ipropylphenyl, 4-tbutylphenyl, 4-methoxyphenyl, 2-methoxyphenyl, 3-methoxyphenyl, 3,4-dimethoxyphenyl, 3,5-dimethoxyphenyl, 3,4,5-trimethoxyphenyl, 4-ethoxyphenyl, 4-ipropoxyphenyl, 4-trifluoromethoxyphenyl, 4-hydroxyphenyl, 4-fluorophenyl, 2,4-difluorophenyl, 2,6-difluorophenyl, 2-fluorophenyl, 3-fluorophenyl, 2-chlorophenyl, 3-chlorophenyl, 4-chlorophenyl, 3,5-chlorophenyl, 4-bromophenyl, 4-chloro-2-fluorophenyl, 4-trifluoromethylphenyl, 3-trifluoromethylphenyl, 2-fluoro-4-trifluoromethylphenyl, 2-chloro-4-trifluoromethylphenyl, 4-chloro-2-methylphenyl, 2-chloro-6-methylphenyl, 3-fluoro-4-methylphenyl, 3,5-difluoro-4-methylphenyl, 4-methylsulphanylphenyl, 4-methylsulphinylphenyl, 4-methylsulphonylphenyl, 4-carboxyphenyl, 4-methoxycarbonylphenyl, 3-methoxycarbonylphenyl, 4-ethoxycarbonylphenyl, 4-carbamoylphenyl, 4-methylcarbamoylphenyl, 4-ethylcarbamoylphenyl, 4-dimethylcarbamoylphenyl, 4-(prop-2-en-1-ylcarbamoyl)phenyl, NH$_2$, NHMe, NHEt, NHPr, NHiPr, NHBu, NHtBu, NHCH$_2$CH=CH$_2$, NHCH$_2$CCH, cyclopentylamino, cyclohexylamino, NHBn, 4-chlorobenzylamino, 4-methoxybenzylamino, NHPh, 4-fluorophenylamino, 2-fluorophenylamino, 3,5-dichlorophenylamino, 2-methylphenylamino, 4-methylphenylamino, 3-cyanophenylamino, 3-trifluoromethylphenylamino, 4-methoxyphenylamino, 4-trifluoromethoxyphenylamino, pyridin-3-ylamino, pyridin-2-ylamino, $NMe_2$, $N(Me)Et$, $NEt_2$, $NHCH_2COOEt$, $NHCH_2COOMe$, $NH(CH_2)_2COOEt$, $N=CHNMe_2$, $N=C(Me)NMe_2$, NHCOMe, NHCOEt, NHCOPr, NHCOBu, NHCOtBu, $NHCOCHMe_2$, $NHCOCH_2CHMe_2$, $NHCOCH=CH_2$, acetyl(methyl)amino, acetyl(ethyl)amino, acetyl(propyl)amino, acetyl(ipropyl)amino, acetyl(butyl)amino, acetyl(phenyl)amino, acetyl(pentyl)amino, acetyl(benzyl)amino, cyclopropylcarbonylamino, cyclobutylcarbonylamino, cyclopentylcarbonylamino, cyclohexylcarbonylamino, cyclopentylacetylamino, phenylacetylamino, 3-phenylpropanoylamino, phenylcarbonylamino, methyl(phenylcarbonyl)amino, ethyl(phenylcarbonyl)amino, propyl(phenylcarbonyl)amino, (4-ethylphenylcarbonyl)amino, (2-chlorophenylcarbonyl)amino, (3-chlorophenylcarbonyl)amino, (4-chlorophenylcarbonyl)amino, (3-methoxycarbonylphenylcarbonyl)amino, (3-carboxyphenylcarbonyl)amino, (2-hydroxyphenylcarbonyl)amino, (4-methoxyphenylcarbonyl)amino, (2,6-dimethylphenylcarbonyl)amino, (4-cyanophenylcarbonyl)amino, (4-methoxycarbonylphenylcarbonyl)amino, (4-methoxycarbonylphenyl)carbonyl(methyl)amino, (4-carboxyphenylcarbonyl)amino, (pyridin-2-ylcarbonyl)amino, (pyridin-3-ylcarbonyl)amino, (pyridin-4-ylcarbonyl)amino, (thiophen-2-ylcarbonyl)amino, (furan-2-ylcarbonyl)amino, (6-chloropyridin-3-ylcarbonyl)amino, (6-methylpyridin-3-ylcarbonyl)amino, (6-methoxypyridin-3-ylcarbonyl)amino, (2-methoxypyridin-3-ylcarbonyl)amino, (pyrazin-2-ylcarbonyl)amino, $NHCOCF_3$, $NHCOCH_2Cl$, $NHCO(CH_2)_3Cl$, $NHCO(CH_2)_4Cl$, $NHCO(CH_2)_5Cl$, $NHCOCH_2OH$, $NHCOCH_2OMe$, $NHCOCH(Me)OH$, $NHCOCH_2NMe_2$, $NHCOCH_2COOEt$, $NHCOCH_2COOMe$, $NHCO(CH_2)_2COOEt$; $NH(CH_2)_2Ph$, NHCOOEt, NHCOOMe, $NHCOOCH_2CH_2Cl$, $NHCONMe_2$, NHCONHEt, NHCONHPr, NHCONHPh, (2-chlorophenyl)carbamoylamino, (3-chlorophenyl)carbamoylamino, (4-chlorophenyl)carbamoylamino, (2-fluorophenyl)carbamoylamino, (3-fluorophenyl)carbamoylamino, (4-fluorophenyl)carbamoylamino, (2-methylphenyl)carbamoylamino, (3-methylphenyl)carbamoylamino, (4-methylphenyl)carbamoylamino, (3-methoxyphenyl)carbamoylamino, or (4-methoxyphenyl)carbamoylamino;

$R^2$ represents phenyl, naphthalen-1-yl, naphthalen-2-yl, 2,3-dihydro-1H-inden-5-yl, 4-chlorophenyl, 3-chlorophenyl, 2-chlorophenyl, 4-fluorophenyl, 3-fluorophenyl, 2-fluorophenyl, 4-bromophenyl, 3-bromophenyl, 3,5-dichlorophenyl, 2,4-difluorophenyl, 2,6-difluorophenyl, 2,4,6-trifluorophenyl, 3,4-dichlorophenyl, 2-chloro-4-fluorophenyl, 3-cyanophenyl, 4-cyanophenyl, 4-hydroxyphenyl, 4-methylphenyl, 3-methylphenyl, 2-methylphenyl, 3,5-dimethylphenyl, 3,4-dimethylphenyl, 4-ethylphenyl, 3-ethylphenyl, 4-propylphenyl, 3-propylphenyl, 4-isopropylphenyl, 4-butylphenyl, 4-t-butylphenyl, 4-hexylphenyl, 4-fluoro-3-methylphenyl, 4-cyclohexylphenyl, 4-methoxyphenyl, 3-methoxyphenyl, 2-methoxyphenyl, 3,4-dimethoxyphenyl, 3,4,5-trimethoxyphenyl, 4-ethoxyphenyl, 4-butoxyphenyl, 4-benzyloxyphenyl, 4-(trifluoromethyl)phenyl, 3-(trifluoromethyl)phenyl, 4-(trifluoromethoxy)phenyl, 1,3-benzodioxol-5-yl, 2,2-difluoro-1,3-benzodioxol-5-yl, 4-(dimethylamino)phenyl, 3-bromo-4-dimethylaminophenyl, 4-(methylsulphanyl)phenyl, 4-methoxycarbonylphenyl, 4-ethoxycarbonylphenyl, 3-methoxycarbonylphenyl, 3-carboxyphenyl, furan-2-yl, 5-methylfuran-2-yl, 3-methylfuran-2-yl, furan-3-yl, thiophen-2-yl, pyridin-2-yl, 5-methylpyridin-2-yl, 6-methylpyridin-2-yl, 5-chloropyridin-2-yl, pyridin-3-yl, or pyridin-4-yl;

$R^3$ represents hydrogen, hydroxyl, methoxy, cyano, methyl, chloromethyl, hydroxymethyl, cyanomethyl, pyrrolidin-1-ylmethyl, COOMe, COOEt, phenylsulphanyl, benzylsulphanyl, phenylsulphonyl, amino, NHMe, NHEt, NHPr, NHBu, $NHCH_2CH=CH_2$, $NHCH_2CCH$, cyclopropylamino, cyclobutylamino, cyclohexylamino, cyclopentylamino, cyclohexyl(methyl)amino, 4-methylpiperazin-1-yl, piperidin-1-yl, pyrrolidin-1-yl, morpholin-1-yl, $NMe_2$, $NEt_2$, $NHCH_2CH_2OCH_3$, $NHCH(Me)CH_2OCH_3$, NHCOPh, (thiophen-2-ylcarbonyl)amino, (naphthalen-1-ylcarbonyl)amino, NHCOMe, NHCOEt, NHCOtBu, cyclopentylcarbonylamino, cyclohexylcarbonylamino, $NHCO(CH_2)_2CH_3$, $NHCO(CH_2)_3CH_3$, $NHCO(CH_2)_4CH_3$, (1-methylcyclohexyl)carbonylamino, NHCOOtBu, $NHCONHCH_2CH_3$, phenylacetylamino, 3-phenylpropanoylamino, 4-phenylbutanoylamino, 5-phenylpentanoylamino, methyl(phenylacetyl)amino, methyl(3-phenylpropanoyl)amino, (3-(4-fluorophenyl)propanoyl)amino, (3-(4-methoxyphenyl)propanoyl)amino, cyclopentylacetylamino, (cyclohexylmethyl)amino, (cyclopentylmethyl)amino, benzylamino, 2-phenylethylamino, 3-phenylpropylamino, benzyl(methyl)amino, methyl(2-phenylethyl)amino, (R)—NHCH(Me)Ph, (S)—NHCH(Me)Ph, (thiophen-2-ylmethyl)amino, 4-fluorobenzylamino, 4-chlorobenzylamino, 3-chlorobenzylamino, 2-chlorobenzylamino, 4-methoxybenzylamino, 3-methoxybenzylamino, 2-methoxybenzylamino, or (naphthalen-2-ylmethyl)amino;

and $R^4$ represents hydrogen or methyl or together with $R^3$ and the pyridine ring to which both are attached forms a bicycle selected from the group consisting of quinolin-4-yl, 1,8-naphthyridin-4-yl, 1H-pyrrolo[2,3-b]pyridin-4-yl.

11. The crop protection composition according to claim 6, wherein $R^1$ represents hydrogen, methyl, ethyl, propyl, 1-methylethyl, butyl, 1,1-dimethylethyl, pentyl, cyclohexyl, $CH_2CF_3$, $CF_2CH_3$, benzyl, 2-phenylethyl, 3-phenylpropyl, acetyl, COOH, COOEt, CHMeOH, $(CH_2)_4OH$, $(CH_2)_6OH$, $CHMeOCOPh$, $CH_2SMe$, $CH_2CH_2SMe$, $CH_2NH_2$, $CH_2NHMe$, $CH_2NHCOPh$, $CH_2COOH$, $CH_2COOEt$, $(CH_2)_3COOH$, $CH_2CONHMe$, phenyl, 4-methylphenyl, 3-methylphenyl, 2-methylphenyl, 4-methoxyphenyl, 2-methoxyphenyl, 4-hydroxyphenyl, 4-fluorophenyl, 2,4-difluorophenyl, 2,6-difluorophenyl, 2-fluorophenyl, 3-fluorophenyl, 2-chlorophenyl, 3-chlorophenyl, 4-chlorophenyl, 4-methylsulphanylphenyl, 4-methylsulphinylphenyl, 4-methylsulphonylphenyl, 4-carboxyphenyl, 4-methoxycarbonylphenyl, 4-carbamoylphenyl, $NH_2$, NHMe, NHEt, NHPr, NHiPr, NHBu, NHBn, NHPh, pyridin-3-ylamino, pyridin-2-ylamino, $NMe_2$, $NEt_2$, NHCH$_2$COOEt, NH(CH$_2$)$_2$COOEt, N=CHNMe$_2$, N=C(Me)NMe$_2$, NHCOMe, NHCOEt, NHCOPr, NHCOBu, NHCOtBu, NHCOCHMe$_2$, NHCOCH$_2$CHMe$_2$, NHCOCH=CH$_2$, acetyl(methyl)amino, acetyl(ethyl)amino, acetyl(propyl)amino, acetyl(ipropyl)amino, acetyl(butyl)amino, acetyl(phenyl)amino, acetyl(pentyl)amino, acetyl(benzyl)amino, cyclopentylcarbonylamino, cyclohexylcarbonylamino, cyclopentylacetylamino, phenylacetylamino, 3-phenylpropanoylamino, phenylcarbonylamino, methyl(phenylcarbonyl)amino, ethyl(phenylcarbonyl)amino, propyl(phenylcarbonyl)amino, (4-ethylphenylcarbonyl)amino, (2-chlorophenylcarbonyl)amino, (3-chlorophenylcarbonyl)amino, (4-chlorophenylcarbonyl)amino, (3-methoxycarbonylphenylcarbonyl)amino, (3-carboxyphenylcarbonyl)amino, (2-hydroxyphenylcarbonyl)amino, (4-methoxyphenylcarbonyl)amino, (2,6-dimethylphenylcarbonyl)amino, (4-cyano-phenylcarbonyl)amino, (4-methoxycarbonylphenylcarbonyl)amino, (4-methoxycarbonylphenyl)carbonyl(methyl)amino, (4-carboxyphenylcarbonyl)amino, (pyridin-2-ylcarbonyl)amino, (pyridin-3-ylcarbonyl)amino, (pyridin-4-ylcarbonyl)amino, (thiophen-2-ylcarbonyl)amino, (furan-2-ylcarbonyl)amino, (6-chloropyridin-3-ylcarbonyl)amino, (6-methylpyridin-3-ylcarbonyl)amino, (6-methoxypyridin-3-ylcarbonyl)amino, (2-methoxypyridin-3-ylcarbonyl)amino, (pyrazin-2-ylcarbonyl)amino, NHCOCF$_3$, NHCOCH$_2$Cl, NHCO(CH$_2$)$_3$Cl, NHCO(CH$_2$)$_4$Cl, NHCO(CH$_2$)$_5$Cl, NHCOCH$_2$OH, NHCOCH$_2$OMe, NHCOCH(Me)OH, NHCOCH$_2$NMe$_2$, NHCOCH$_2$COOEt, NHCOCH$_2$COOMe, NHCO(CH$_2$)$_2$COOEt, or NHCOOCH$_2$CH$_2$Cl, NH(CH$_2$)$_2$Ph;

R$^2$ represents phenyl, naphthalen-1-yl, 4-chlorophenyl, 3-chlorophenyl, 2-chlorophenyl, 4-fluorophenyl, 3-fluorophenyl, 4-bromophenyl, 3-bromophenyl, 3,5-dichlorophenyl, 3,4-dichlorophenyl, 3-cyanophenyl, 4-hydroxyphenyl, 4-methylphenyl, 3-methylphenyl, 2-methylphenyl, 3,5-dimethylphenyl, 3,4-dimethylphenyl, 4-ethylphenyl, 3-ethylphenyl, 4-propylphenyl, 3-propylphenyl, 4-isopropylphenyl, 4-butylphenyl, 4-t-butylphenyl, 4-hexylphenyl, 4-fluoro-3-methylphenyl, 4-methoxyphenyl, 3-methoxyphenyl, 2-methoxyphenyl, 3,4-dimethoxyphenyl, 3,4,5-trimethoxyphenyl, 4-ethoxyphenyl, 4-butoxyphenyl, 4-benzyloxyphenyl, 4-(trifluoromethyl)phenyl, 3-(trifluoromethyl)phenyl, 4-(trifluoromethoxy)phenyl, 1,3-benzodioxol-5-yl, 4-(dimethylamino)phenyl, 4-(methylsulphanyl)phenyl, or furan-2-yl, or thiophen-2-yl;

R$^3$ represents hydrogen, hydroxyl, methyl, chloromethyl, hydroxymethyl, cyanomethyl, pyrrolidin-1-ylmethyl, COOMe, phenylsulphanyl, benzylsulphanyl, phenylsulphonyl, amino, cyclohexylamino, cyclopentylamino, cyclohexyl(methyl)amino, 4-methylpiperazin-1-yl, piperidin-1-yl, pyrrolidin-1-yl, morpholin-1-yl, NHCOPh, (thiophen-2-ylcarbonyl)amino, (naphthalen-1-ylcarbonyl)amino, NHCOMe, NHCOEt, NHCOtBu, cyclopentylcarbonylamino, cyclohexylcarbonylamino, NHCOPr, NHCOBu, NHCO(CH$_2$)$_4$CH$_3$, (1-methylcyclohexyl)carbonylamino, NHCOOtBu, NHCONHEt, phenylacetylamino, 3-phenylpropanoylamino, 4-phenylbutanoylamino, 5-phenylpentanoylamino, methyl(phenylacetyl)amino, methyl(3-phenylpropanoyl)amino, (3-(4-fluorophenyl)propanoyl)amino, (3-(4-methoxyphenyl)propanoyl)amino, cyclopentylacetylamino, (cyclohexylmethyl)amino, (cyclopentylmethyl)amino, benzylamino, 2-phenylethylamino, 3-phenylpropylamino, benzyl(methyl)amino, methyl(2-phenylethyl)amino, (R)—NHCH(Me)Ph, (S)—NHCH(Me)Ph, (thiophen-2-ylmethyl)amino, 4-fluorobenzylamino, 4-chlorobenzylamino, 3-chlorobenzylamino, 2-chlorobenzylamino, 4-methoxybenzylamino, 3-methoxybenzylamino, 2-methoxybenzylamino, or (naphthalen-2-ylmethyl)amino;

and

R$^4$ represents hydrogen.

* * * * *